(12) United States Patent
Barbosa

(10) Patent No.: US 10,723,726 B2
(45) Date of Patent: Jul. 28, 2020

(54) SOLID FORMS OF (Z)-4-(5-((3-BENZYL-4-OXO-2-THIOXOTHIAZOLIDIN-5-YLIDENE)METHYL)FURAN-2-YL)BENZOIC ACID

(71) Applicant: GB006, INC., San Diego, CA (US)

(72) Inventor: Antonio J. Barbosa, Ave Maria, FL (US)

(73) Assignee: GB006, INC., San Diego, CA (US)

( * ) Notice: Subject to any disclaimer, the term of this patent is extended or adjusted under 35 U.S.C. 154(b) by 0 days.

(21) Appl. No.: 15/735,560

(22) PCT Filed: Jun. 10, 2016

(86) PCT No.: PCT/US2016/037067
§ 371 (c)(1),
(2) Date: Dec. 11, 2017

(87) PCT Pub. No.: WO2016/201356
PCT Pub. Date: Dec. 15, 2016

(65) Prior Publication Data
US 2018/0354938 A1    Dec. 13, 2018

Related U.S. Application Data

(60) Provisional application No. 62/275,655, filed on Jan. 6, 2016, provisional application No. 62/175,066, filed on Jun. 12, 2015.

(51) Int. Cl.
| | | |
|---|---|---|
| C07D 417/06 | (2006.01) |
| A61P 35/00 | (2006.01) |
| C07D 215/08 | (2006.01) |
| C07C 215/08 | (2006.01) |

(52) U.S. Cl.
CPC ............ *C07D 417/06* (2013.01); *A61P 35/00* (2018.01); *C07C 215/08* (2013.01); *C07B 2200/13* (2013.01)

(58) Field of Classification Search
None
See application file for complete search history.

(56) References Cited

U.S. PATENT DOCUMENTS

| | | | |
|---|---|---|---|
| 7,718,680 B2 * | 5/2010 | Pellecchia | A61K 31/427 514/369 |
| 8,268,816 B2 | 9/2012 | Gupta et al. | |
| 8,846,667 B2 | 9/2014 | Gupta et al. | |
| 9,023,876 B2 | 5/2015 | Gupta | |
| 9,328,105 B2 | 5/2016 | Gupta | |
| 2004/0002526 A1 | 1/2004 | Klein et al. | |
| 2005/0042213 A1 | 2/2005 | Gelder et al. | |
| 2007/0072922 A1 | 3/2007 | Brook et al. | |
| 2012/0010255 A1 | 1/2012 | Gupta | |
| 2014/0303026 A1 | 10/2014 | Gupta et al. | |
| 2016/0151336 A1 | 6/2016 | Gupta et al. | |

FOREIGN PATENT DOCUMENTS

| | | |
|---|---|---|
| WO | 2005016227 A2 | 2/2005 |
| WO | 2006024699 A1 | 3/2006 |
| WO | 2006066846 A1 | 6/2006 |
| WO | 2008005651 A2 | 1/2008 |
| WO | 2008082537 A2 | 7/2008 |
| WO | 2012005800 A1 | 1/2012 |
| WO | 2013159082 A1 | 10/2013 |
| WO | WO2013159082 | * 10/2013 |
| WO | 2016201356 A1 | 12/2016 |

OTHER PUBLICATIONS

Schafer, S., Kolkhof, P. Failure is an option: learning from unsuccessful proof-of-concept trials. Drug Discovery Today. Nov. 2008, 13, 913-916.*
Honig, H., Pullman, W. From bench to clinic and back: Perspective on the 1st IQPC Translational Research conference. Journal of Translational Medicine. Dec. 2004, 2, 44.*
"Table II—FDA-Approved Commercially Marketed Salts", Rennington's Pharmaceutical Science, (17th Edition), Gennaro, A. R., Editor, Mack Publishing Company, Easton, PA 18042, (1985), p. 1418.*
Raseback et al. "Micron-Size Drug Particles: Common and Novel Micronization Techniques". PHarmaceutical Development and Technology, 2004, 9, 1-13.*
Berge et al., "Pharmaceutical Salts". Journal of Pharmaceutical Sciences, 1977, 66, 1-19.*
PCT/US2016/037067, "International Search Report" dated Sep. 8, 2016, 2 pages.
Björklund, "Stabilization of the Activated $\alpha_M\beta_2$ Integrin by a Small Molecule Inhibits Leukocyte Migration and Recruitment," Biochemistry, 2006, 45, 2862-2871.
Celik et al., "Agonist Leukadherin-1 Increases CD11b/CD18-Dependent Adhesion Via Membrane Tethers," Biophysical Journal, Dec. 3, 2013, vol. 105, Issue 11, pp. 2517-2527.
Faridi et al., "Identification of novel agonists of the integrin CD11b/CD18," Bioorg. Med. Chem. Lett., 2009, vol. 19, pp. 6902-6906.
Faridi et al., "High-Throughput Screening based Identification of Small Molecule Antagonists of Integrin CD11b/CD18 Ligand Binding," Biochem. Biophys. Res. Commun., Mar. 26, 2010, vol. 394(1), pp. 194-199.
Faridi et al., "Small molecule agonists of integrin CD11b/CD18 do not induce global conformational changes and are significantly better than activating antibodies in reducing vascular injury," Biochimica et Biophysica Acta 1830, 2013, pp. 3696-3710.
Jagarapu et al., "Efficacy of Leukadherin-1 in the Prevention of Hyperoxia-Induced Lung Injury in Neonatal Rats," American Journal of Respiratory Cell and Molecular Biology, Dec. 2015, vol. 53, No. 6, pp. 793-801.

(Continued)

*Primary Examiner* — Po-Chih Chen
(74) *Attorney, Agent, or Firm* — Seed IP Law Group LLP

(57) ABSTRACT

The present invention provides new salts and crystalline forms of leukadherin LA1 [(Z)-4-(5-((3-benzyl-4-oxo-2-thioxothiazolidin-5-ylidene)methyl)furan-2-yl)benzoic acid] according to Formula I. Methods for preparation of the salts and crystalline forms are also described, as well as methods for treating 2 integrin-mediated diseases and conditions using the salts and crystalline forms.

26 Claims, 23 Drawing Sheets

(56) References Cited

OTHER PUBLICATIONS

Khan et al., "A small molecule β2 integrin agonist improves chronic kidney allograft survival by reducing leukocyte recruitment and accompanying vasculopathy," Original Research in Medicine, Nov. 2014, vol. 1, Article 45, 11 pages.
Maiguel et al., "Small Molecule-Mediated Activation of the Integrin CD11b/CD18 Reduces Inflammatory Disease", Sci Signal., Sep. 6, 2011, vol. 4, Issue 189, pp. 1-32.
Park et al., "A Simple, No-Wash Cell Adhesion-Based High-Throughput Assay for the Discovery of Small-Molecule Regulators of the Integrin CD11b/CD18," Journal of Biomolecular Screening, 2007, 12(3), pp. 406-417.
Reed et al., "Complement Receptor 3 Influences Toll-like Receptor 7/8-Dependent Inflammation," The Journal of Biological Chemistry, Mar. 29, 2013, vol. 288, No. 13, pp. 9077-9083.
Caira, "Crystalline Polymorphism of Organic Compounds" Topics in Current Chemistry, vol. 198, 1998, pp. 163-208.

\* cited by examiner

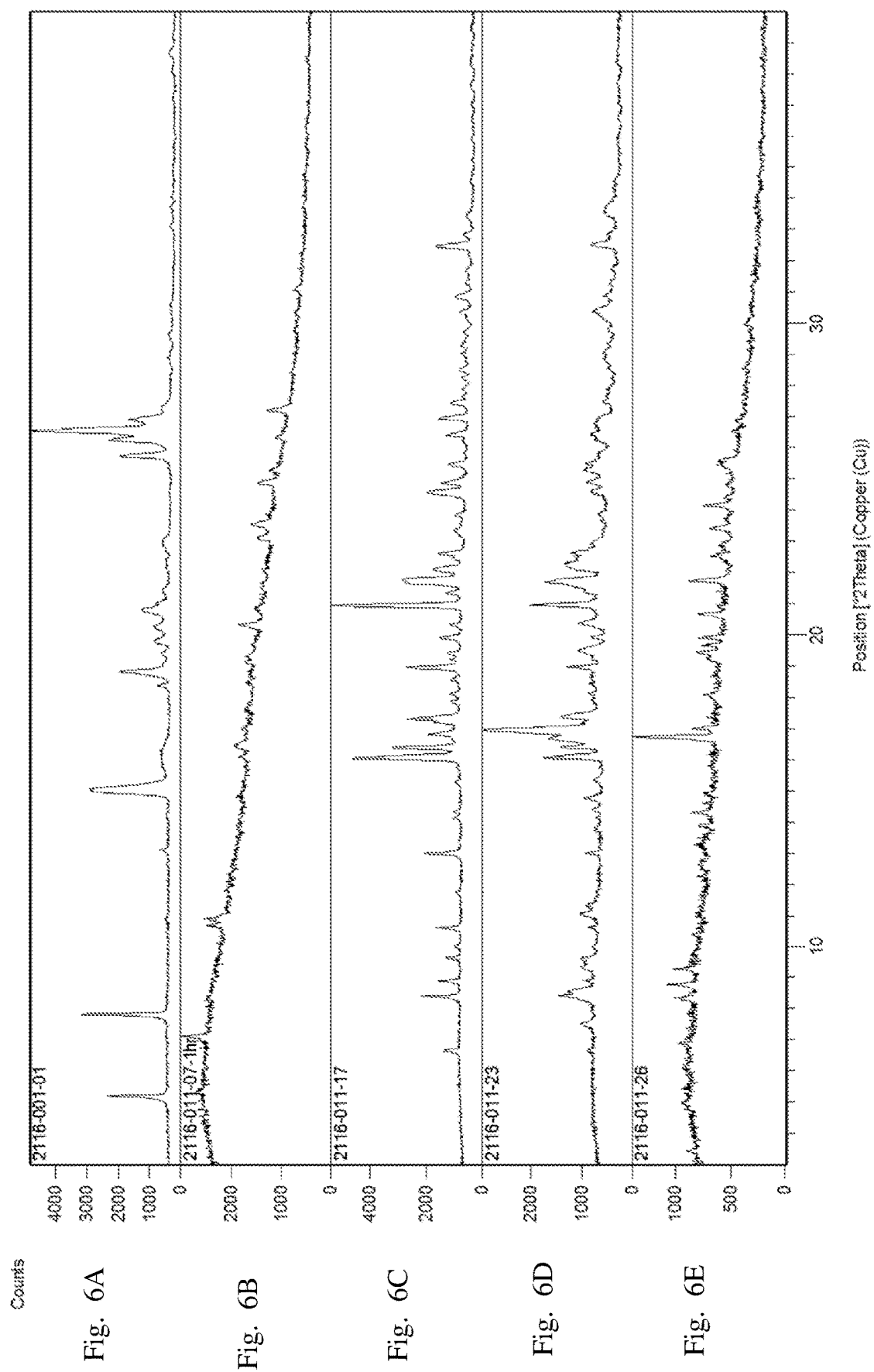

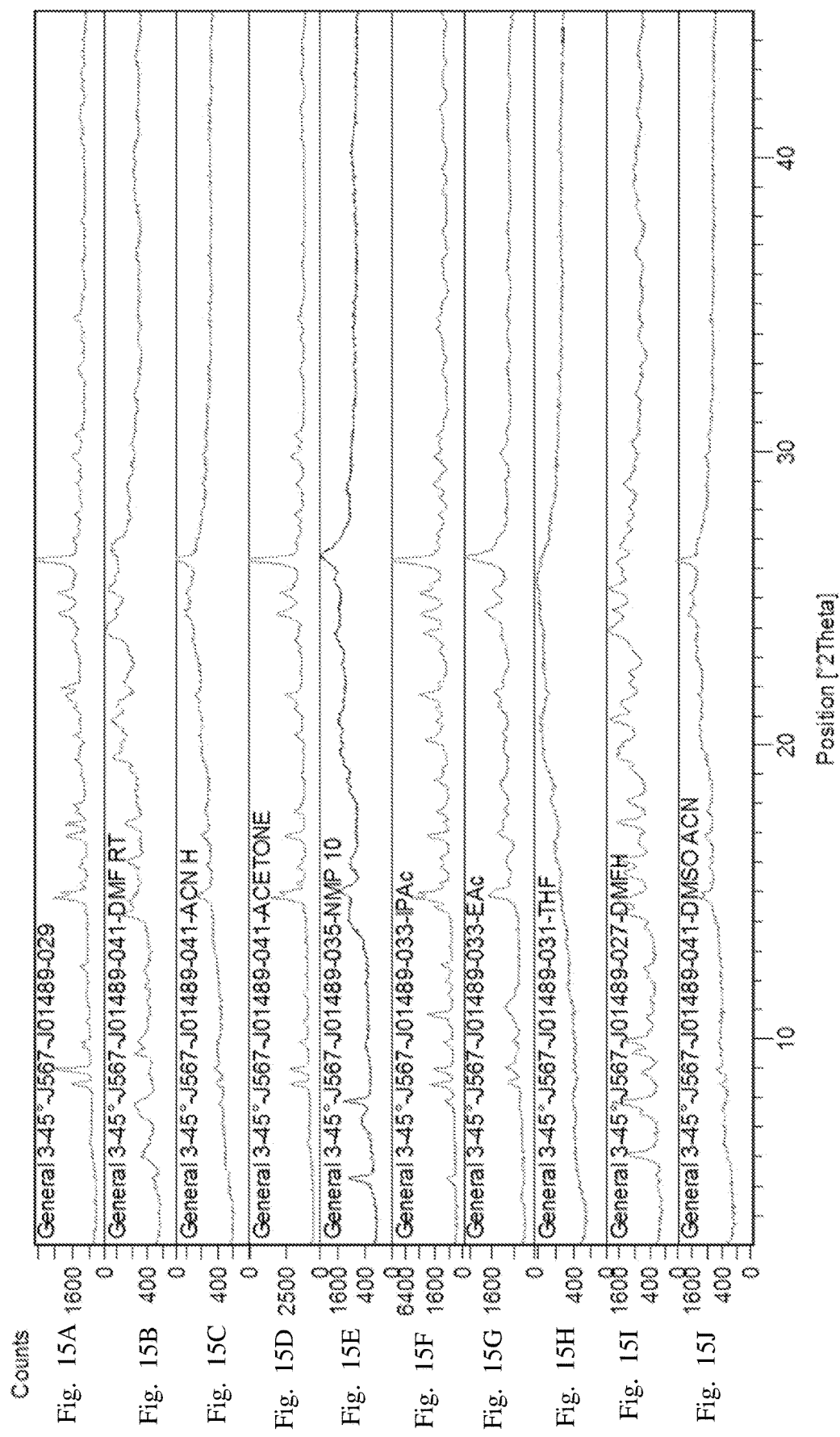

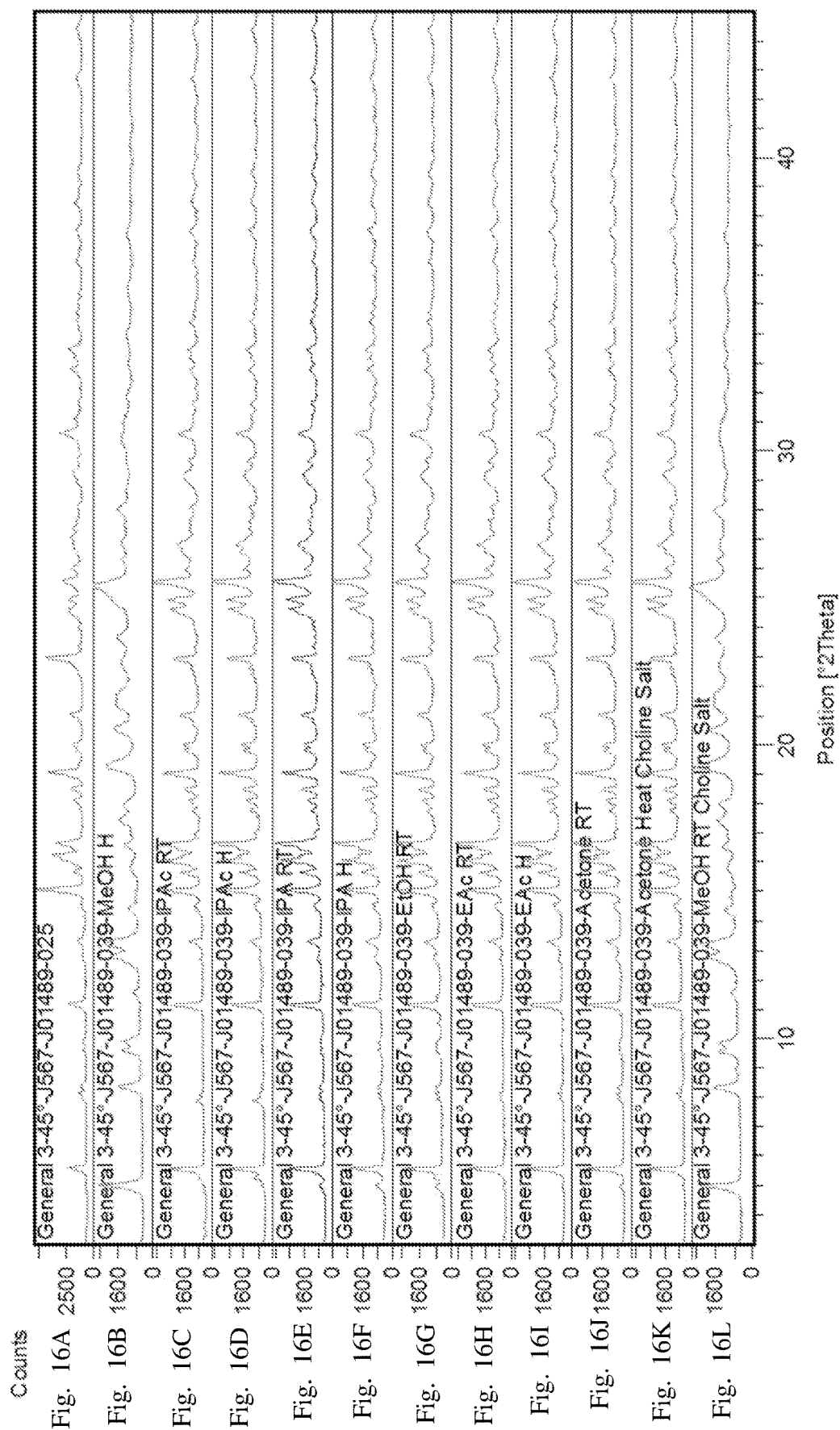

SOLID FORMS OF (Z)-4-(5-((3-BENZYL-4-OXO-2-THIOXOTHIAZOLIDIN-5-YLIDENE)METHYL) FURAN-2-YL)BENZOIC ACID

CROSS-REFERENCES TO RELATED APPLICATIONS

The present application is a U.S. national stage entry of International Pat. Appl. No. PCT/US2016/037067, filed Jun. 10, 2016, which claims priority to U.S. Provisional Pat. Appl. No. 62/175,066, filed Jun. 12, 2015, and U.S. Provisional Pat. Appl. No. 62/275,655, filed Jan. 6, 2016, which applications are incorporated herein by reference in their entirety.

STATEMENT AS TO RIGHTS TO INVENTIONS MADE UNDER FEDERALLY SPONSORED RESEARCH AND DEVELOPMENT

The present invention was made with funds provided by NIAID Advanced Technology SBIR (NIAID-AT-SBIR [R43/R44]) Grant #1 R43 AI100499-01A1. The United States government has certain rights in the invention.

BACKGROUND OF THE INVENTION

Leukocyte (i.e., white blood cell) activation, migration and recruitment are essential for the immune response to injury and infection, as well as in various inflammatory and autoimmune disorders. The β2 integrins, a sub-family of α/β heterodimeric integrin receptors including highly expressed integrin CD11b/CD18, are leukocyte-specific receptors that modulate leukocyte functions including cell adhesion, migration, recruitment and activation. CD11b/CD18 recognizes the complement fragment iC3b, Fibrinogen, and ICAM-1 as ligands, among various others. CD11b/CD18 has been implicated in many inflammatory and autoimmune diseases, such as ischemia-reperfusion injury (including acute renal failure and atherosclerosis), lupus, inflammatory bowel disease, Crohn's disease, rheumatoid arthritis, multiple sclerosis, lupus nephritis, focal segmental glomerulosclerosis, renal injury, tissue damage, glaucoma, ophthalmic conditions, allograft rejection (such as nephropathy), transplantation, graft versus host disease, stroke, neointimal thickening in response to vascular injury, and the resolution of inflammatory processes.

Leukocytic β2 integrins also contribute to processes including tumor growth, tumor re-growth, tumor metastases, tumor infiltration, potentiation of inflammatory and autoimmune diseases, production of reactive oxygen species, and modulation of a number of pro- and anti-inflammatory genes in inflammatory cells. Blocking of β2 integrins, including CD11b/CD18, and their ligands has been shown to decrease the severity of inflammatory response in vivo in certain experimental models. However, such blocking agents have had little success in treating inflammatory/autoimmune diseases in humans.

More recently, new anti-inflammatory compositions and methods have been developed using compounds that activate integrins and reduce recruitment of inflammatory immune cells into tissues by increasing integrin CD11b/CD18-dependent cell adhesion to immobilized ligands. Leukadherins are a group of such small molecule agonists targeting integrin CD11b/CD18 (Maiguel, et al. 2011. *Sci. Signal.* 4:1-14; Park, et al. 2007. *J. Biomol. Screen.* 12:406-417; Faridi, et al. 2009. *Bioorg. Med. Chem. Lett.* 19:6902-6906.). Leukadherins also reduce leukocyte activation and pro-inflammatory signaling pathways. Among them, leukadherin 1 ("LA1;" (Z)-4-(5-((3-benzyl-4-oxo-2-thioxothiazolidin-5-ylidene)methyl)furan-2-yl)benzoic acid; Formula I below) has demonstrated particular anti-inflammatory efficacy. LA1 has been shown to reduce recruitment of leukocytes during acute peritonitis in mice, reduce neointimal thickening upon vascular injury in rats, and reduce renal ischemia/reperfusion injury in mice. LA1 and uses thereof have been described in U.S. Pat. No. 9,023,876 as well as in International Pat. Appl. Nos. PCT/US2011/034753 and PCT/US2013/037548, which applications are incorporated herein by reference in their entirety.

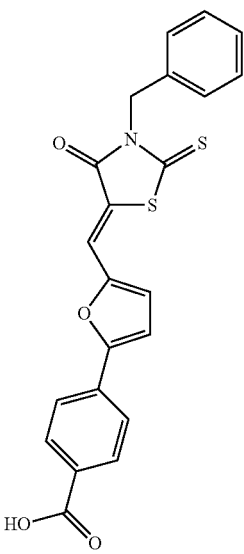

Formula I

Improved formulations of LA1 are needed to further leverage the utility that LA1 has exhibited in the studies outlined above. Improved dissolution profiles, pharmacokinetic profiles, and/or stability profiles provided by new formulations are expected to enhance efficacy and enable advantageous dosage forms. The present invention provides new salts and crystalline forms that meet the need for improved LA1 formulations.

BRIEF SUMMARY OF THE INVENTION

In one aspect, the present invention provides salts of LA1 [(Z)-4-(5-((3-benzyl-4-oxo-2-thioxothiazolidin-5-ylidene)methyl)furan-2-yl)benzoic acid] and crystalline forms thereof. The crystalline forms of LA1 salts include: a crystalline form G of a choline salt of a compound of Formula I as described herein; a crystalline form O of a choline salt of a compound of Formula I as described herein; a crystalline form Q of a choline salt of a compound of Formula I as described herein; a crystalline form H of a meglumine salt of a compound of Formula I as described herein; and a crystalline form T of a meglumine salt of a compound of Formula I as described herein. In related aspects, the invention provides methods for making the salts and crystalline forms as described herein, as well as pharmaceutical formulations containing at least one salt or crystalline form as described herein and a pharmaceutically acceptable excipient.

In another aspect, the invention provides methods for treating a condition mediated by β2 integrins. The methods include administering a therapeutically effective amount of a salt or crystalline form as described herein to a patient in need thereof.

The salts and crystalline forms of the invention, as well as other aspects, objects, and advantages associated with them, will become more apparent when read with the detailed description and figures which follow.

BRIEF DESCRIPTION OF THE DRAWINGS

FIGS. 6A-E show XRPD patterns for: LA1 bicarbonate salt (FIG. 6 A); LA1 meglumine salt, Form H (FIG. 6 B); LA1 tromethamine salts (FIG. 6 C and FIG. 6 D); and LA1 choline salt, Form O (FIG. 6E).

FIGS. 15A-J show an XRPD pattern obtained for LA1 meglumine salts in various solvents.

FIGS. 16A-L show an XRPD pattern obtained for LA1 choline salts in various solvents.

DETAILED DESCRIPTION OF THE INVENTION

I. General

Figure 1:
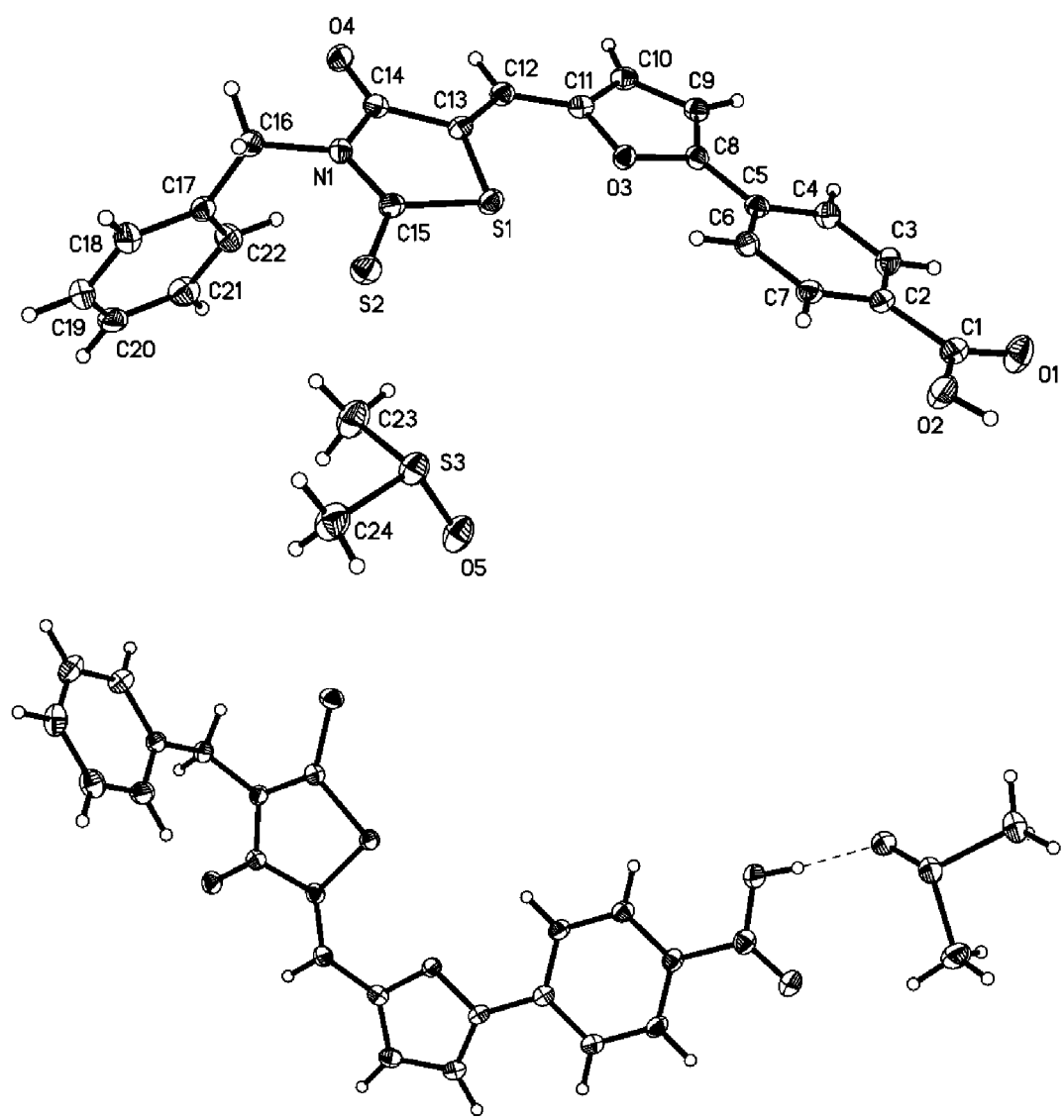
FIG. 1 shows the X-ray crystal structure for LA1 DMSO solvate, Form B.

The present invention provides novel salts and crystalline forms of leukadherin 1 (LA1; (Z)-4-(5-((3-benzyl-4-oxo-2-thioxothiazolidin-5-ylidene)methyl)furan-2-yl)benzoic acid). These new forms of LA1 provide a number of advantages, including increased bioavailability for orally administered pharmaceutical formulations. Accordingly, the invention enables improved methods for treating β2 integrin-mediated conditions.

II. Definitions

"LA1" refers to the compound (Z)-4-(5-((3-benzyl-4-oxo-2-thioxothiazolidin-5-ylidene)methyl)furan-2-yl)benzoic acid as shown in Formula I.

"Salt" refers to a base addition salt prepared by combining LA1 free acid with a pharmaceutically acceptable base.

"Pharmaceutically acceptable" is art-recognized and, as used herein to refer to a composition, excipient, adjuvant, or other material and/or dosage form, refers to a substance which, within the scope of sound medical judgment, is suitable for use in contact with the tissues of human beings and animals without excessive toxicity, irritation, allergic response, or other problems or complications, commensurate with a reasonable benefit/risk ratio. Examples of pharmaceutically acceptable bases include, but are not limited to ammonia, L-arginine, calcium hydroxide, choline, meglumine, lysine, magnesium hydroxide, potassium hydroxide, sodium hydroxide.

"Choline" refers to 2-hydroxy-N,N,N-trimethylethanamonium. A "choline salt" is salt containing at least one 2-hydroxy-N,N,N-trimethylethanamonium cation.

"Meglumine" refers to (2R,3R,4R,5S)-6-(methylamino) hexane-1,2,3,4,5-pentol. A "meglumine salt" is a salt containing at least one (2S,3R,4R,5R)-2,3,4,5,6-pentahydroxy-N-methylhexan-1-aminium cation.

"Crystalline form" refers to a solid form of a compound wherein the constituent molecules are packed in a regularly ordered, repeating pattern. A crystalline form can be triclinic, monoclinic, orthorhombic, tetragonal, trigonal, hexagonal, or cubic. A crystalline form can contain one or more regions, i.e., grains, with distinct crystal boundaries. A crystalline solid can contain two or more crystal geometries.

"Integrin" refers to a non-covalently linked α/β-heterodimeric cell surface receptor that mediates cell adhesion, migration and signaling. Integrins are expressed in a wide range of organisms, including *C. elegans, Drosophila* sp., amphibians, reptiles, birds, and mammals, including humans. A number of α subunits, designated, for example, αV, α5 and the like, and a number of β subunits, designated, for example, β1, β2, β3, β5 and the like, have been identified, and various combinations of these subunits are represented in the integrin superfamily, including α5β1, αVβ3 and αVβ5. The superfamily of integrins can be subdivided into families, for example, as αV-containing integrins, including αVβ3 and αVβ5, or the β1-containing integrins, including α5β1 and αVβ1.

"β2 integrin" refers to a leukocyte-specific integrin having a β2-subunit (also referred to as CD18). β2 integrins have distinct α-subunits selected from CD11a, CD11b, CD11c and CD11d. β2 integrins, including highly expressed integrin CD11b/CD18 (also known as Mac-1, CR3 and αMβ2), modulate leukocyte functions, including cell adhesion, migration, recruitment and activation.

"β2-mediated," as used herein to refer to diseases and/or conditions in a patient, means that the disease or condition results (in whole or in part) from a chemical or physical process involving a β2 integrin. β2-mediated diseases and conditions include inflammatory and autoimmune diseases. Examples of β2-mediated diseases and conditions include, but are not limited to, ischemia-reperfusion injury (including acute renal failure and atherosclerosis), lupus, inflammatory bowel disease, Crohn's disease, rheumatoid arthritis, multiple sclerosis, lupus nephritis, focal segmental glomerulosclerosis, renal injury, glaucoma, ophthalmic conditions, allograft rejection (such as nephropathy), transplantation, graft versus host disease, neurological disorders, Alzheimer's disease, Parkinson's disease, dermatitis, tissue damage, stroke, neointimal thickening in response to vascular injury, anti-GBM nephritis, pain (including chronic pain), and cancers, including primary tumors and metastatic tumors, such as breast cancer, melanoma, prostate cancer, lung cancer, pancreatic cancer, and others.

"Cancer" refers to an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. In general, a cancer will be associated with the presence of one or more tumors, i.e., abnormal cell masses. The term "tumor" is meant to include all types of cancerous growths or oncogenic processes, metastatic tissues or malignantly transformed cells, tissues, or organs, irrespective of histopathologic type or stage of invasiveness.

Examples of cancer include malignancies of various organ systems, such as lung cancers, breast cancers, thyroid cancers, lymphoid cancers, gastrointestinal cancers, and genito-urinary tract cancers. Cancer can also refer to adenocarcinomas, which include malignancies such as colon cancers, renal-cell carcinoma, prostate cancer and/or testicular tumors, non-small cell carcinoma of the lung, cancer of the small intestine, and cancer of the esophagus. Carcinomas are malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. An "adenocarcinoma" refers to a carcinoma derived from glandular tissue or in which the tumor cells form recognizable glandular structures. A "sarcoma" refers to a malignant tumor of mesenchymal derivation.

"Melanoma" refers to a tumor arising from a melanocyte. Melanomas occur most commonly in the skin and are frequently observed to metastasize widely.

"Immune checkpoint" refers to a regulatory pathway that contributes to co-stimulatory or inhibitory control of T-cell activity in an organism. Interaction of "immune checkpoint proteins," including proteins on the surfaces of antigen-presenting cells and T-cells, contribute to regulation and maintenance of self-tolerance and the duration and amplitude of physiological immune responses in the organism. See, e.g., D. M. Pardol. *Nature Reviews Cancer* 12, 252-264 (2012). Examples of immune checkpoint proteins include, but are not limited to, A2aR (adenosine A2a receptor); BTLA, B, and T (lymphocyte attenuator); ICOS (inducible T cell co-stimulator); KIR (killer cell immunoglobulinlike receptor); LAG3 (lymphocyte activation gene 3); PD1 (programmed cell death protein 1); CTLA-4 (cytotoxic T-lymphocyte-associated antigen 4); and TIM3 (T cell membrane protein 3).

"Immune checkpoint inhibitor" refers to a molecule that totally or partially reduces, inhibits, interfere with, or otherwise modulates the activity of one or more checkpoint proteins. Immune checkpoint inhibitors can, for example, include antibodies or peptide-like compounds derived from antibodies.

"PD1" refers to programmed cell death protein 1, also known as CD279, expressed by T-cells, B-cells, and monocytes. PD-1 is a type I surface glycoprotein characterized by a V-set immunoglobulin superfamily (IgSF) domain attached to a transmembrane domain and a cytoplasmic domain containing two tyrosine-based signaling motifs. PD1 binds at least two ligands: PD-L1 (expressed by cells including T-cells, B-cells, dendritic cells, macrophages, and mesenchymal stem cells) and PD-L2 (expressed by cells including dendritic cells, macrophages, and mast cells).

"CTLA-4" refers to cytotoxic T-lymphocyte-associated antigen 4, also known as CD152, which is expressed exclusively on T-cells. CTLA-4 includes a single Ig-fold extracellular domain with three CDR-like loops, and binds to ligands CD80 (B7.1) and CD86 (B7.2), among others, that are differentially expressed in antigen presenting cells.

"Leukocyte marker" refers to a biomolecule (e.g., a polypeptide) found on the cell surface of a leukocyte. Leukocyte markers include, but are not limited to, T-cell antigen receptors; CD1; NK cell receptors; IDO1/2; TDO; CSF1R; VEGFR; SIRPa; cell adhesion molecules (e.g., CD2, CD58 (LFA-3), CD3, CD4, CD5, CD7, CD8); β2 integrins (e.g., LeuCAM, CD11a (LFA-1), CD11b (MAC-1 (CR3)), CD11c (CR4), CD18, CD16 (FcR111), CD21 (CR2), CD23, CD25, CD30, CD35 (CR1)); β3 integrins (e.g., CD41, CDS1); homing receptors (e.g., CD44, Mel-14); β1 integrins (e.g., CD49a-f (VLA-1), VLA-2, VLA-3, VLA-4); CD14; CD56; CD68; CD71; and CD163.

"Integrin" refers to a non-covalently linked α/β-heterodimeric cell surface receptor that mediates cell adhesion, migration and signaling. Integrins are expressed in a wide range of organisms, including *C. elegans, Drosophila* sp., amphibians, reptiles, birds, and mammals, including humans. A number of α subunits, designated, for example, αV, α5 and the like, and a number of β subunits, designated, for example, β1, β2, β3, β5 and the like, have been identified, and various combinations of these subunits are represented in the integrin superfamily, including α5β1, αVβ3 and αVβ5. The superfamily of integrins can be subdivided into families, for example, as αV-containing integrins, including αVβ3 and αVβ5, or the β1-containing integrins, including α5β1 and αVβ1.

"β2 integrin" refers to a leukocyte-specific integrin having a β2-subunit (also referred to as CD18). β2 integrins have distinct α-subunits selected from CD11a, CD11b, CD11c and CD11d. β2 integrins, including highly expressed integrin CD11b/CD18 (also known as Mac-1, CR3 and αMβ2), modulate leukocyte functions, including cell adhesion, migration, recruitment and activation.

"Myeloid cell" generally refers to any white blood cell (i.e., leukocyte) which is not a lymphocyte (e.g., not a natural killer cell, T cell, or B cell). Myeloid cells include macrophages, dendritic cells, and granulocytic cells.

The term "treating," as used herein, unless otherwise indicated, means reversing, alleviating, inhibiting the progress of, or preventing the disorder or condition to which such term applies, or one or more symptoms of such disorder or condition. The term "treatment," as used herein, refers to the act of treating, as "treating" is defined immediately above.

A "therapeutically effective amount" is the amount of an LA1 salt or crystalline form is needed to provide a desired level of drug in the tissues, bloodstream, or other physical compartment of a patient, the desired level giving rise to an anticipated physiological response or biological effect when the LA1 salt or crystalline form is administered by the chosen route of administration. The precise amount will depend upon numerous factors including, for example, the particular LA1 salt or crystalline form; the specific pharmaceutical formulation or delivery device employed; the severity of the disease state; and patient adherence to a treatment regimen. Therapeutically effective amounts of LA1 salts and crystalline forms can be readily determined by one skilled in the art based upon the information provided herein.

"About" and "around," as used herein to modify a numerical value, indicate a defined range around that value. If "X" were the value, "about X" or "around X" would generally indicate a value from 0.95X to 1.05X including, for example, from 0.98X to 1.02X or from 0.99X to 1.01X. Any reference to "about X" or "around X" specifically indicates at least the values X, 0.95X, 0.96X, 0.97X, 0.98X, 0.99X, 1.01X, 1.02X, 1.03X, 1.04X, and 1.05X. Thus, "about X" and "around X" are intended to teach and provide written description support for a claim limitation of, e.g., "0.98X." When the quantity "X" only includes whole-integer values (e.g., "X carbons"), "about X" or "around X" indicates from (X-1) to (X+1). In such cases, "about X" or "around X" specifically indicates at least the values X, X-1, and X+1.

III. LA1 Salts

One of skill in the art will appreciate that a number of pharmaceutically acceptable bases can be used to prepare LA1 salts. Pharmaceutically acceptable bases include, but are not limited to, ammonia, L-arginine, calcium hydroxide, choline, meglumine, magnesium hydroxide, benethamine, benzathine, betaine, deanol, diethylamine, 2-diethylaminoethanol, hydrabamine, 1-(2-hydroxyethyl)-pyrrolidine, t-butylamine, tromethamine, piperazine, imidazole, ethylenediamine, ethanolamine, diethanolamine, and triethanolamine. In certain embodiments, the LA1 salt comprises a cation derived from a pharmaceutically acceptable base selected from ammonia, L-arginine, calcium hydroxide, choline, meglumine, and magnesium hydroxide.

In one aspect, the invention provides a choline salt of a compound of Formula I:

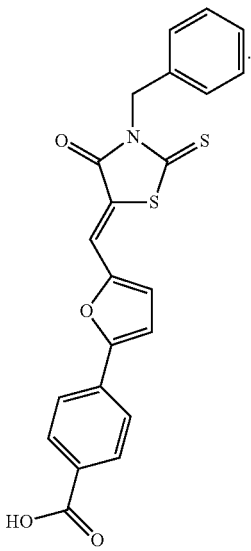

(I)

As described above, Formula I corresponds to LA1. Choline is also referred to by synonyms including (2-hydroxyethyl)trimethylammonium and 2-hydroxy-N,N,N-trimethylethanamonium. As used herein, "choline salt" refers to a salt containing as least one 2-hydroxy-N,N,N-trimethylethanamonium cation. In certain embodiments, the choline salt of LA1 is a salt according to Formula II:

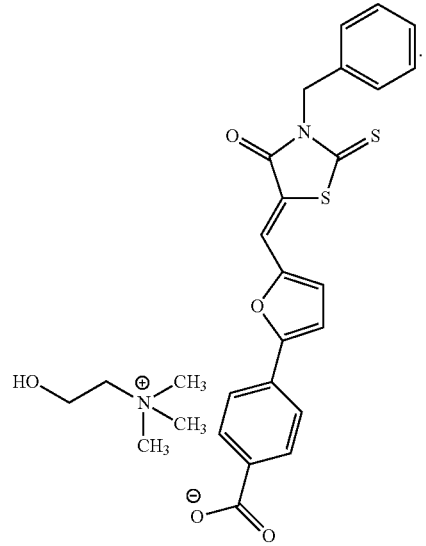

(II)

In one aspect, the invention provides a crystalline form G of a choline salt of a compound of Formula I:

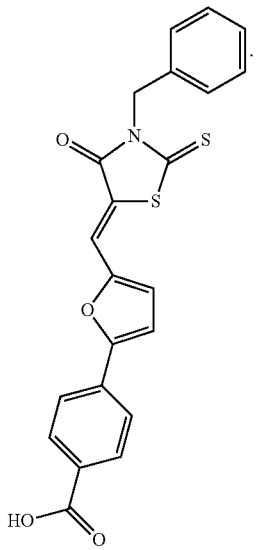

(I)

In some embodiments, crystalline form G is characterized by an X-ray powder diffraction (XRPD) pattern including at least three peaks selected from 5.6, 7.9, 11.2, 13.3, 15.0, 15.7, 16.1, 16.2, 16.5, 16.6, 17.8, 18.1, 18.5, 19.1, 19.8, 20.0, 21.1, 23.0, 24.6, 25.0, 25.6, 26.6, 26.8, 26.9, 29.3, 29.7, 30.6, 30.7, and 34.4 °2θ, ±0.2 °2θ, as determined on a diffractometer using Cu-Kα radiation. For example, crystalline form G can include 3, 4, 5, 6, 7, 8, 9, 10, 11, 12, 13, 14, 15, 16, 17, 18, 19, 20, 21, 22, 23, 24, 25, 26, 27, 28, or 29 such peaks.

In some embodiments, crystalline form G is characterized by an X-ray powder diffraction (XRPD) pattern including at least six peaks selected from 5.6, 11.2, 13.3, 15.0, 15.7, 16.1, 16.6, 19.1, 24.6, 25.0, 25.6, and 26.8 °2θ, ±0.2 °2θ, as determined on a diffractometer using Cu-Kα radiation.

In some embodiments, crystalline form G is characterized by an X-ray powder diffraction (XRPD) pattern including at least ten peaks selected from 5.6, 11.2, 13.3, 15.0, 15.7, 16.1, 16.6, 19.1, 24.6, 25.0, 25.6, and 26.8°2θ, ±0.2°2θ, as determined on a diffractometer using Cu-Kα radiation.

Figures 5A, 5B:
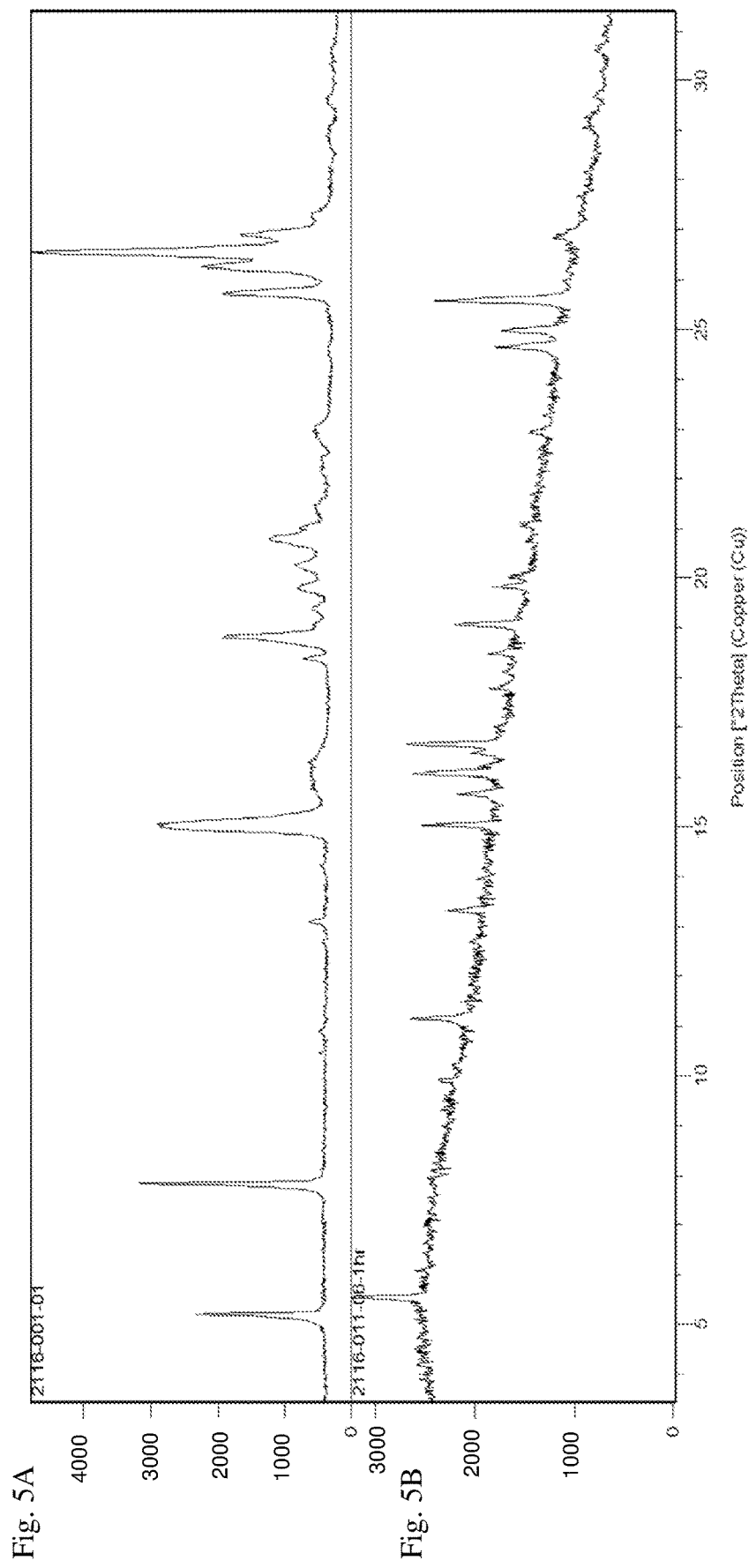
FIGS. 5A-B show XRPD patterns obtained for disordered crystalline LA1, Form A (FIG. 5A) and LA1 choline salt, Form G (FIG. 5B).

In some embodiments, crystalline form G is characterized by an X-ray powder diffraction (XRPD) pattern substantially in accordance with FIG. 5B, as determined on a diffractometer using Cu-Kα radiation.

In another aspect, the invention provides a crystalline form O of a choline salt of a compound of Formula I:

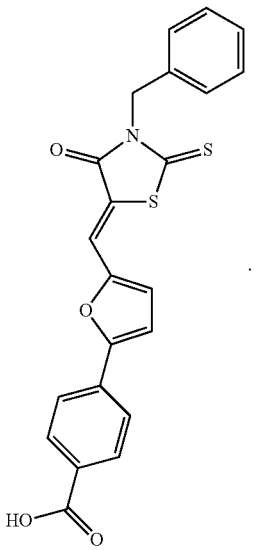

(I)

In some embodiments, crystalline form O is characterized by an X-ray powder diffraction (XRPD) pattern including at least three peaks selected from 8.4, 8.8, 9.3, 13.3, 14.3, 16.7, 17.0, 18.1, 19.4, 19.6, 19.9, 20.7, 20.9, 21.4, 21.7, 22.5, 23.4, 24.1, and 25.5 °2θ, ±0.2 °2θ as determined on a diffractometer using Cu-Kα radiation. For example, crystalline form O can include 3, 4, 5, 6, 7, 8, 9, 10, 11, 12, 13, 14, 15, 16, 17, 18, or 19 such peaks.

In some embodiments, crystalline form O is characterized by an X-ray powder diffraction (XRPD) pattern including at least six peaks selected from 8.4, 8.8, 9.3, 16.7, 19.9, 20.7, 21.7, 22.5, 23.4, and 25.5 °2θ, ±0.2 °2θ as determined on a diffractometer using Cu-Kα radiation.

In some embodiments, crystalline form O is characterized by an X-ray powder diffraction (XRPD) pattern substantially in accordance with FIG. 6E, as determined on a diffractometer using Cu-Kα radiation.

In another aspect, the invention provides a crystalline form Q of a choline salt of a compound of Formula I:

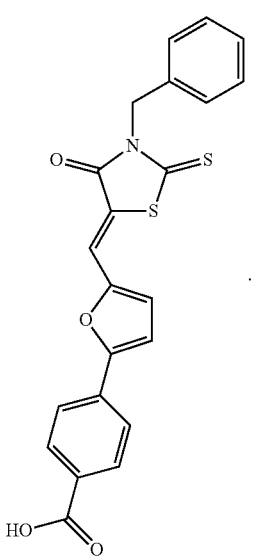

(I)

In some embodiments, the crystalline form Q is characterized by an X-ray powder diffraction (XRPD) pattern including at least three peaks selected from 5.0, 5.2, 8.4, 9.6, 9.9, 11.5, 12.6, 12.8, 13.3, 14.4, 15.8, 16.1, 16.6, 17.5, 18.0, 19.3, 20.6, 20.7, 21.5, 21.7, 22.9, 23.7, 24.8, 25.1, 25.3, 25.3, 25.5, 26.3, 26.9, 27.0, 28.1, 28.8, 30.4, 31.2, 32.0, 35.7, and 37.4 °2θ±0.2 °2θ, as determined on a diffractometer using Cu-Kα radiation. For example, crystalline form Q can include 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, or 37 such peaks.

In some embodiments, the crystalline form Q is characterized by an X-ray powder diffraction (XRPD) pattern including at least six peaks selected from 5.0, 8.4, 9.6, 9.9, 11.5, 12.8, 13.3, 14.4, 18.0, 19.3, 23.7, and 25.5 °2θ±0.2 °2θ, as determined on a diffractometer using Cu-Kα radiation.

In some embodiments, the crystalline form Q is characterized by an X-ray powder diffraction (XRPD) pattern including at least ten peaks selected from 5.0, 8.4, 9.6, 9.9, 11.5, 12.8, 13.3, 14.4, 18.0, 19.3, 23.7, and 25.5 °2θ±0.2 °2θ, as determined on a diffractometer using Cu-Kα radiation.

In some embodiments, the crystalline form Q is characterized by an X-ray powder diffraction (XRPD) pattern substantially in accordance with D, as determined on a diffractometer using Cu-Kα radiation.

In another aspect, the invention provides a crystalline form R of a choline salt of a compound of Formula I:

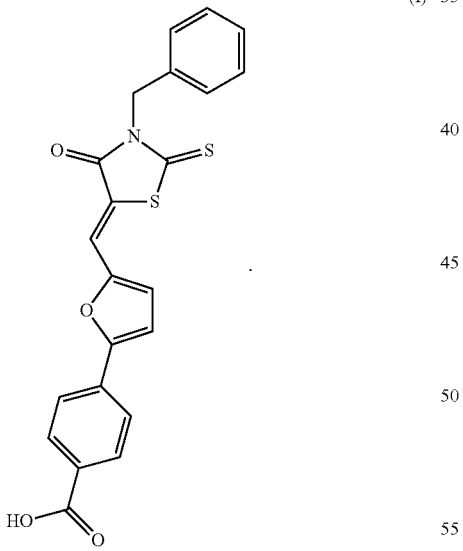

In some embodiments, the crystalline form R is characterized by an X-ray powder diffraction (XRPD) pattern including at least three peaks selected from 5.1, 5.6, 8.0, 8.2, 8.4, 9.8, 11.2, 12.7, 13.4, 14.6, 15.1, 15.7, 16.1, 16.3, 16.7, 17.1, 17.8, 18.2, 18.5, 19.1, 19.9, 20.1, 21.1, 22.6, 23.0, 23.4, 24.0, 24.5, 24.7, 25.0, 25.6, 26.0, 26.6, 26.8, 27.1, 27.4, 27.7, 28.1, 29.3, 29.7, 30.6, 31.1, 31.7, 32.2, 32.8, 33.2, 33.5, 34.5, 34.8, 35.1, 35.4, 36.5, 37.6, 38.5, 39.5, 40.4, 41.3, 42.7, and 44.4 °2θ, ±0.2 °2θ, as determined on a diffractometer using Cu-Kα radiation. For example, crystalline form R can include 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, or 59 such peaks.

In some embodiments, the crystalline form R is characterized by an X-ray powder diffraction (XRPD) pattern including at least six peaks selected from 5.6, 11.2, 15.1, 16.3, 16.7, 19.1, 20.1, 21.1, 23.0, 24.5, 25.0, 25.6, 26.0, 31.1, 32.8, and 33.5±0.2 °2θ, as determined on a diffractometer using Cu-Kα radiation.

In some embodiments, the crystalline form R is characterized by an X-ray powder diffraction (XRPD) pattern including at least nine peaks selected from 5.6, 11.2, 15.1, 16.3, 16.7, 19.1, 20.1, 21.1, 23.0, 24.5, 25.0, 25.6, 26.0, 31.1, 32.8, and 33.5±0.2 °2θ, as determined on a diffractometer using Cu-Kα radiation.

Figure 7:
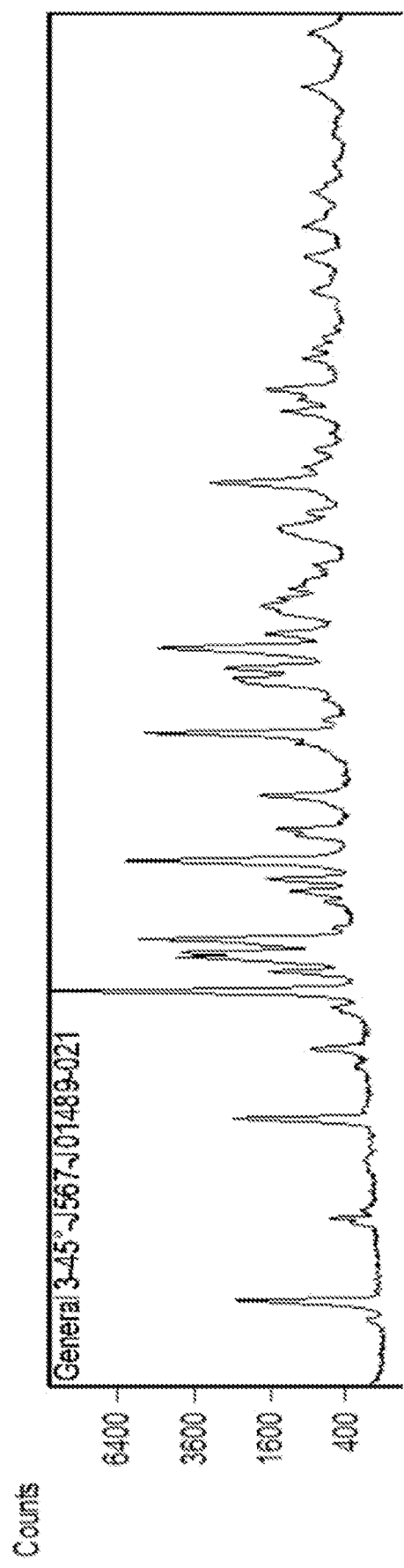
FIG. 7 shows an XRPD pattern obtained for LA1 choline salt, Form R.

In some embodiments, the crystalline form R is characterized by an X-ray powder diffraction (XRPD) pattern in accordance with FIG. 7, as determined on a diffractometer using Cu-Kα radiation. In some embodiments, the crystalline form R is characterized by a differential scanning calorimetry thermogram comprising an endothermic peak at around 224.5° C.

In another aspect, the invention provides a crystalline form S of a choline salt of a compound of Formula I:

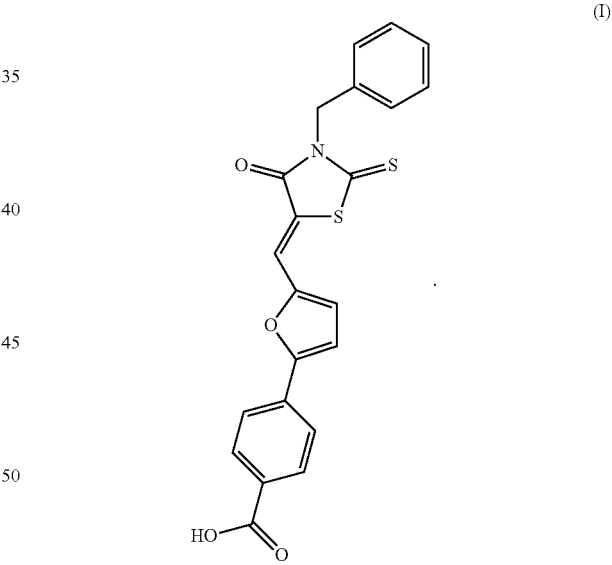

In some embodiments, the crystalline form S is characterized by an X-ray powder diffraction (XRPD) pattern including at least three peaks selected from 5.1, 8.4, 9.6, 10.0, 11.6, 12.9, 13.3, 14.4, 14.9, 15.8, 16.6, 17.4, 18.0, 19.2, 19.3, 20.6, 21.4, 21.7, 22.7, 23.7, 24.8, 25.4, 26.3, 26.8, 28.1, 28.7, 29.6, 30.3, 31.0, 31.9, 33.0, 34.0, 35.7, 37.4, 39.2, 40.5, and 41.7 °2θ, ±0.2 °2θ, as determined on a diffractometer using Cu-Kα radiation. For example, crystalline form S can include 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, or 37 such peaks.

In some embodiments, the crystalline form S is characterized by an X-ray powder diffraction (XRPD) pattern including at least six peaks selected from 5.1, 8.4, 9.6, 10.0, 12.9, 13.3, 16.6, 17.4, 18.0, 19.2, 20.6, 21.4, 21.7, 23.7, 25.4, and 28.1 °2θ±0.2 °2θ, as determined on a diffractometer using Cu-Kα radiation.

In some embodiments, the crystalline form S is characterized by an X-ray powder diffraction (XRPD) pattern including at least ten peaks selected from 5.1, 8.4, 9.6, 10.0, 12.9, 13.3, 16.6, 17.4, 18.0, 19.2, 20.6, 21.4, 21.7, 23.7, 25.4, and 28.1 °2θ±0.2 °2θ, as determined on a diffractometer using Cu-Kα radiation.

Figure 8:
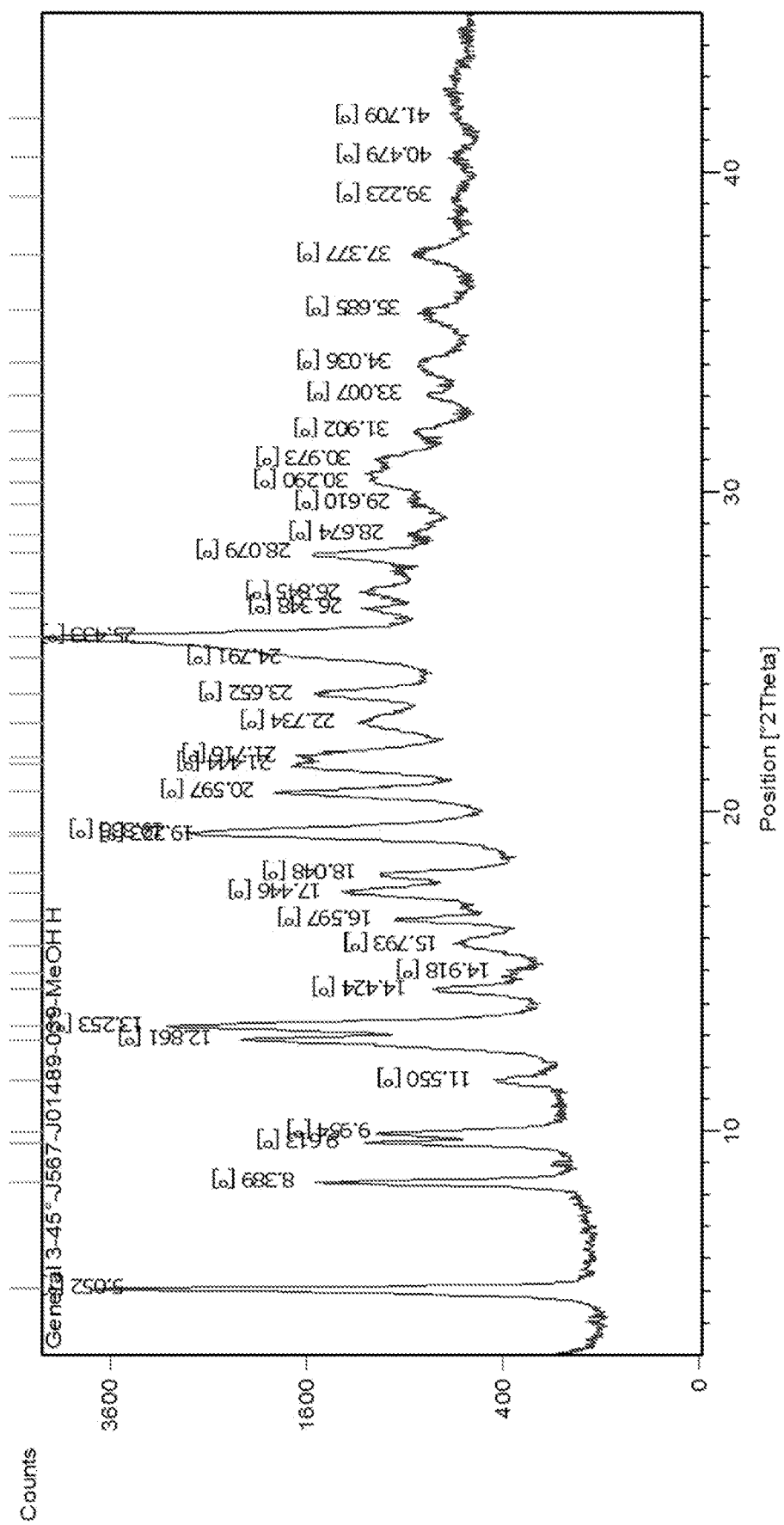
FIG. 8 shows an XRPD pattern obtained for LA1 choline salt, Form S.
Figure 9:
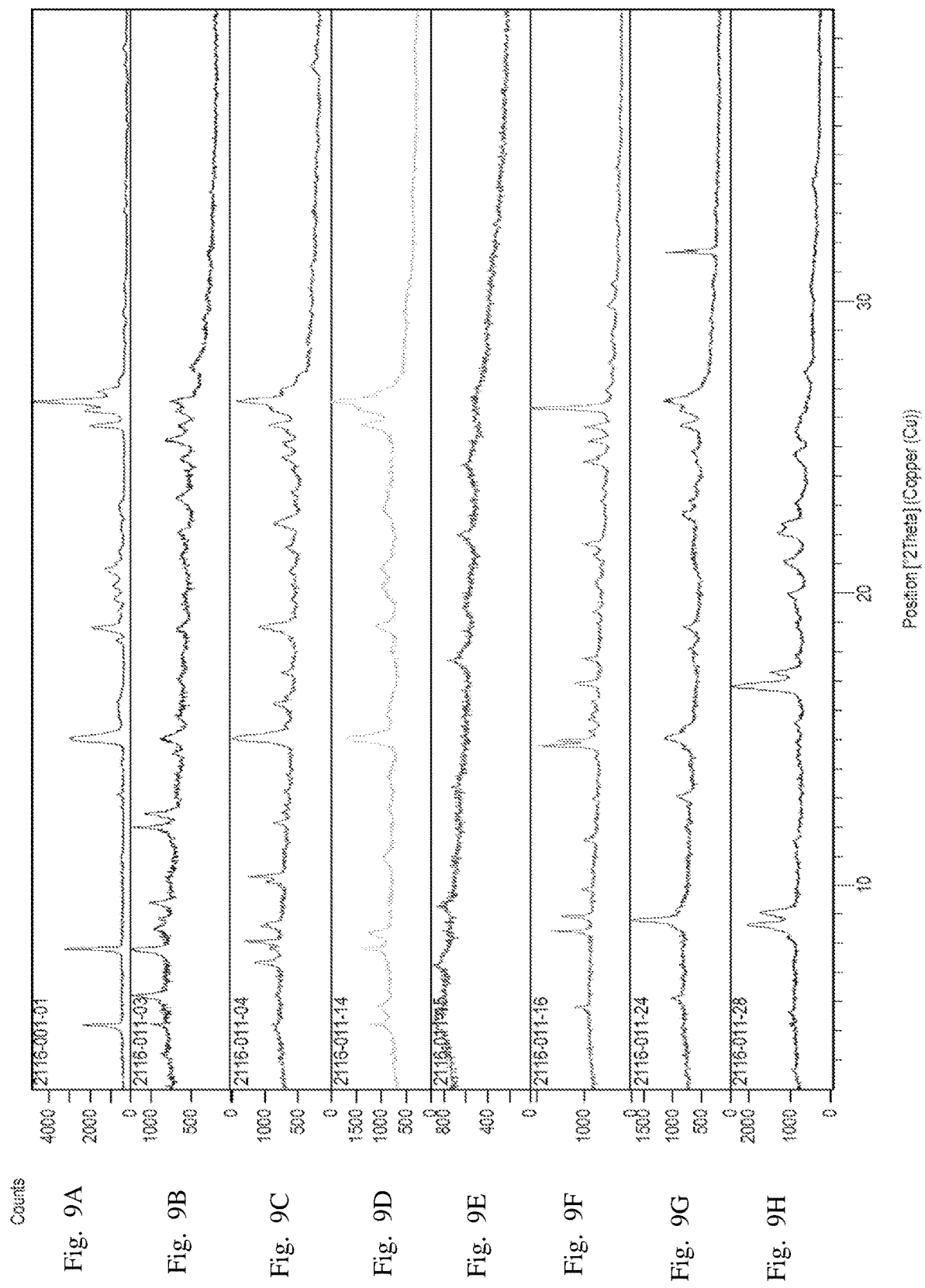
FIGS. 9A-H show XRPD patterns obtained for disordered solids: LA1 salt (FIG. 9A); LA1 calcium salt (FIG. 9B); LA1 magnesium salt (FIG. 9C); LA1 sodium salt (FIG. 9D); LA1 potassium salt (FIG. 9E); LA1 ammonium salt (FIG. 9F); LA1 calcium salt (FIG. 9G); LA1 piperazine salt (FIG. 9H).

In some embodiments, the crystalline form S is characterized by an X-ray powder diffraction (XRPD) pattern substantially in accordance with FIG. 8, as determined on a diffractometer using Cu-Kα radiation.

In another aspect, the invention provides a meglumine salt of a compound of Formula I:

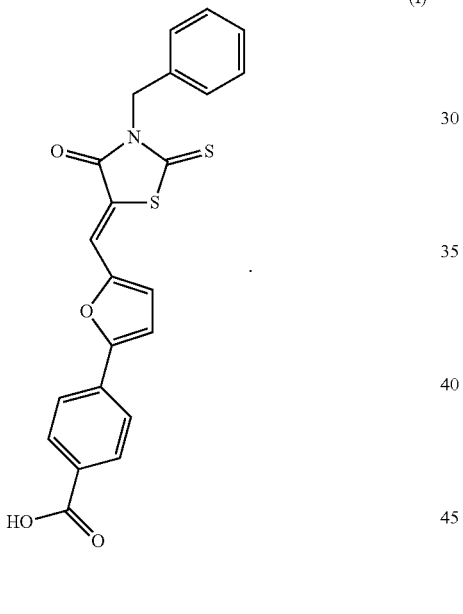

(I)

Meglumine is also referred to by synonyms including N-methyl-D-glucamine and (2R,3R,4R,5S)-6-(methylamino)hexane-1,2,3,4,5-pentol. As used herein, "meglumine salt" refers to a salt containing at least one (2S,3R,4R,5R)-2,3,4,5,6-pentahydroxy-N-methylhexan-1-aminium cation. In certain embodiments, the meglumine salt of LA1 is a salt according to Formula III:

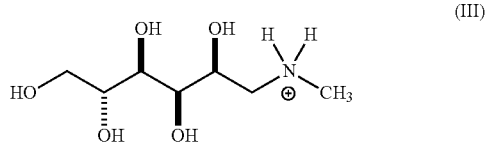

(III)

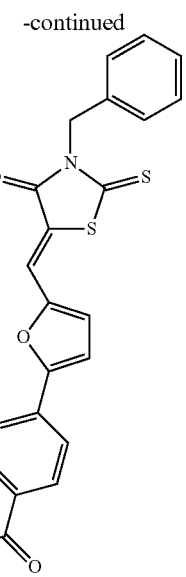

-continued

In another aspect, the invention provides a crystalline form H of a meglumine salt of a compound of Formula I:

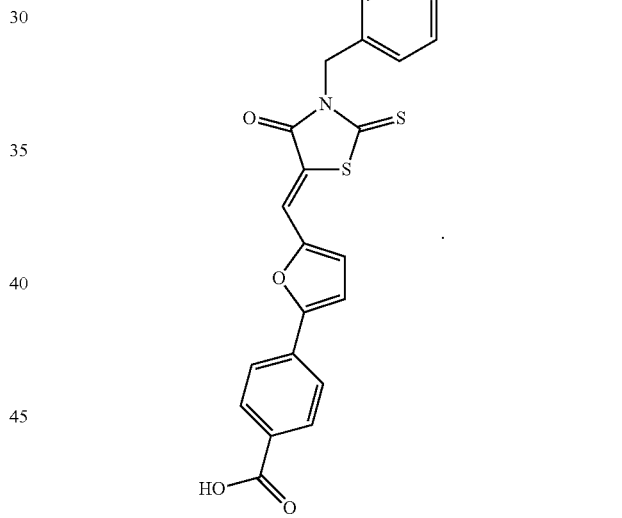

(I)

In some embodiments, crystalline form H is characterized by an X-ray powder diffraction (XRPD) pattern including at least three peaks selected from 5.3, 7.1, 10.7, 10.9, 16.1, 16.5, 17.7, 18.5, 20.3, 23.6, 24.9, and 27.2 °2θ±0.2 °2θ, as determined on a diffractometer using Cu-Kα radiation. For example, crystalline form H can include 3, 4, 5, 6, 7, 8, 9, 10, 11, or 12 such peaks.

In some embodiments, crystalline form H is characterized by an X-ray powder diffraction (XRPD) pattern including at least six peaks selected from 5.3, 7.1, 10.7, 10.9, 16.1, 16.5, 17.7, 18.5, 20.3, 23.6, 24.9, and 27.2 °2θ±0.2 °2θ, as determined on a diffractometer using Cu-Kα radiation.

In some embodiments, crystalline form H is characterized by an X-ray powder diffraction (XRPD) pattern including at least ten peaks selected from 5.3, 7.1, 10.7, 10.9, 16.1, 16.5, 17.7, 18.5, 20.3, 23.6, 24.9, and 27.2 °2θ±0.2 °2θ, as determined on a diffractometer using Cu-Kα radiation.

In some embodiments, crystalline form H is characterized by an X-ray powder diffraction (XRPD) pattern substantially in accordance with FIG. 6B, as determined on a diffractometer using Cu-Kα radiation.

In another aspect, the invention provides a crystalline form L of a meglumine salt of a compound of Formula I:

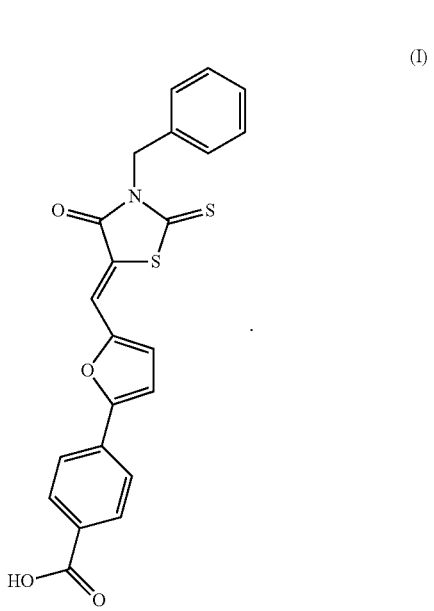 [SMILES: O=C(O)c1ccc(-c2ccc(/C=C3\SC(=S)N(Cc4ccccc4)C3=O)o2)cc1]

(I)

In some embodiments, crystalline form L is characterized by an X-ray powder diffraction (XRPD) pattern including at least three peaks selected from 5.3, 7.9, 8.5, 9.0, 9.9, 10.6, 10.9, 11.6, 12.0, 12.6, 13.1, 14.5, 14.8, 15.0, 15.3, 15.9, 16.2, 16.9, 17.4, 17.8, 18.0, 18.4, 18.8, 19.2, 20.2, 20.8, 21.3, 21.7, 22.1, 23.2, 23.8, 24.5, 25.2, 25.5, 26.3, 26.9, 27.3, 27.9, 28.4, 28.9, 29.2, 29.8, 30.3, 30.6, 31.1, 32.1, 32.8, 34.1, 34.5, 34.9, 35.1, 36.0, 36.5, 37.5, 38.0, 38.9, 39.6, 40.7, 41.7, 42.5, and 42.9 °2θ, ±0.2 °2θ, as determined on a diffractometer using Cu-Kα radiation. For example, crystalline form L can include 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, or 61 such peaks.

In some embodiments, crystalline form L is characterized by an X-ray powder diffraction (XRPD) pattern including at least six peaks selected from 8.5, 9.0, 10.9, 15.0, 16.9, 20.2, 21.7, 23.8, 24.5, 25.2, 26.3, 29.2, and 29.8 °2θ±0.2 °2θ, as determined on a diffractometer using Cu-Kα radiation.

In some embodiments, crystalline form L is characterized by an X-ray powder diffraction (XRPD) pattern including at least ten peaks selected from 8.5, 9.0, 10.9, 15.0, 16.9, 20.2, 21.7, 23.8, 24.5, 25.2, 26.3, 29.2, and 29.8 °2θ±0.2 °2θ, as determined on a diffractometer using Cu-Kα radiation.

Figure 11:
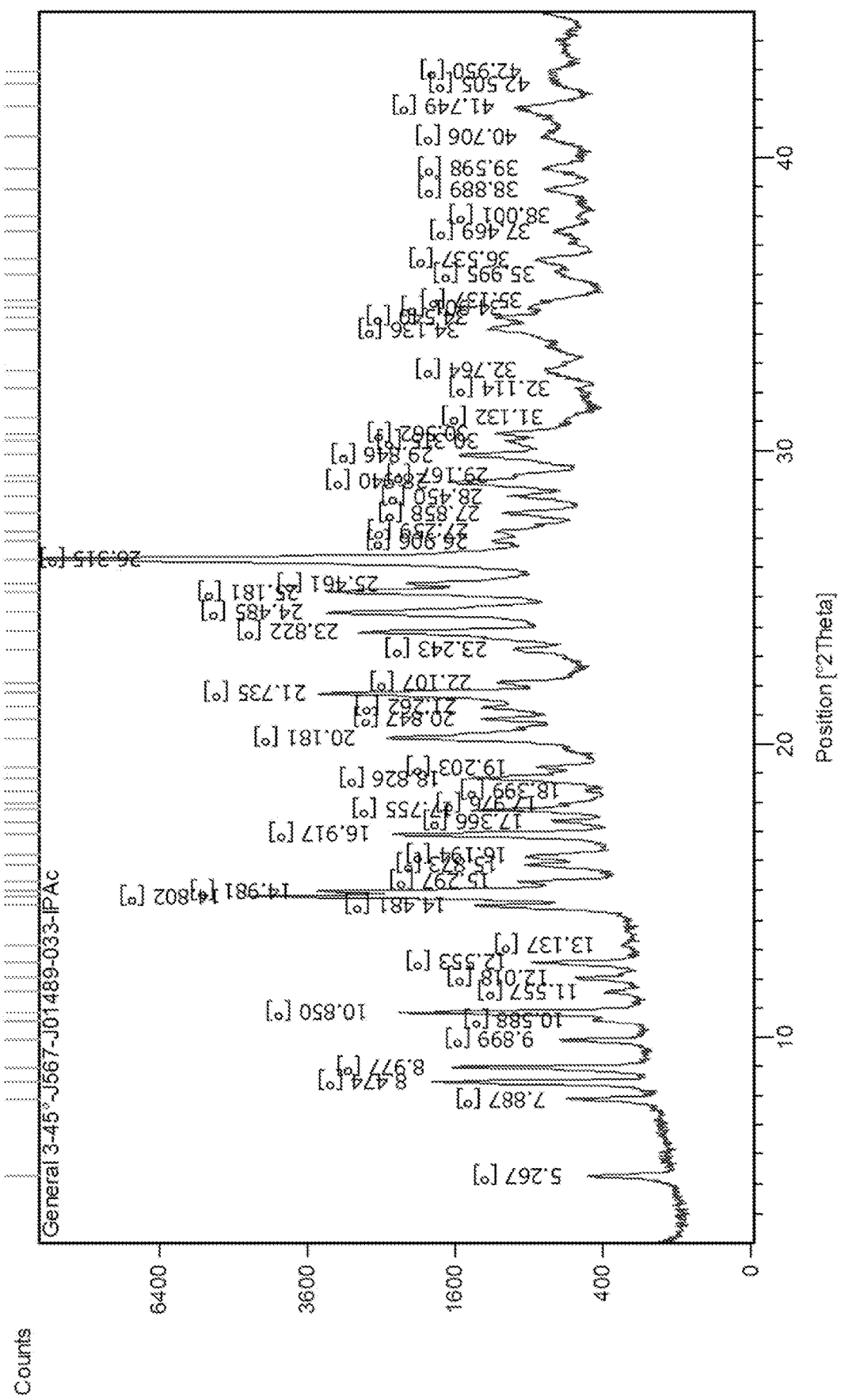
FIG. 11 shows an XRPD pattern obtained for LA1 meglumine salt, Form L.

In some embodiments, crystalline form L is characterized by an X-ray powder diffraction (XRPD) pattern substantially in accordance with FIG. 11, as determined on a diffractometer using Cu-Kα radiation. In some embodiments, the crystalline form L is characterized by a differential scanning calorimetry thermogram comprising an endothermic peak at around 136.3° C.

In another aspect, the invention provides a crystalline form M of a meglumine salt of a compound of Formula I:

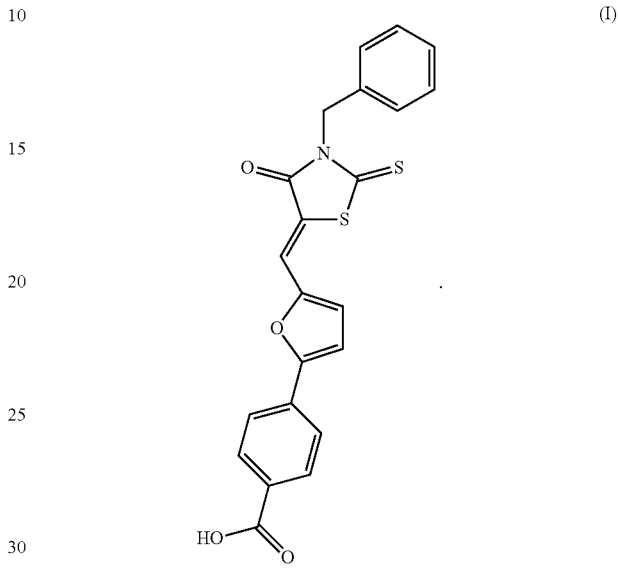

(I)

In some embodiments, crystalline form M is characterized by an X-ray powder diffraction (XRPD) pattern including at least three peaks selected from 6.5, 8.5, 9.0, 9.9, 10.6, 11.6, 14.4, 14.8, 15.0, 15.3, 15.9, 16.1, 16.9, 17.8, 18.0, 19.0, 20.4, 20.8, 21.3, 21.7, 23.6, 24.5, 25.2, 26.3, 26.9, 27.5, 27.9, 28.5, 28.9, 29.8, 30.6, 32.1, 32.8, 33.8, 34.5, 36.0, 36.4, 37.1, 38.0, 39.7, 40.7, 41.7, 43.0, and 44.0 °2θ, ±0.2 °2θ, as determined on a diffractometer using Cu-Kα radiation. For example, crystalline form M can include 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, or 44 such peaks.

In some embodiments, crystalline form M is characterized by an X-ray powder diffraction (XRPD) pattern including at least six peaks selected from 8.5, 9.0, 14.8, 15.0, 16.9, 18.0, 21.7, 24.5, 25.2, 26.3, and 29.8 °2θ±0.2 °2θ, as determined on a diffractometer using Cu-Kα radiation.

In some embodiments, crystalline form M is characterized by an X-ray powder diffraction (XRPD) pattern including at least nine peaks selected from 8.5, 9.0, 14.8, 15.0, 16.9, 18.0, 21.7, 24.5, 25.2, 26.3, and 29.8±0.2 °2θ, as determined on a diffractometer using Cu-Kα radiation.

Figure 12:
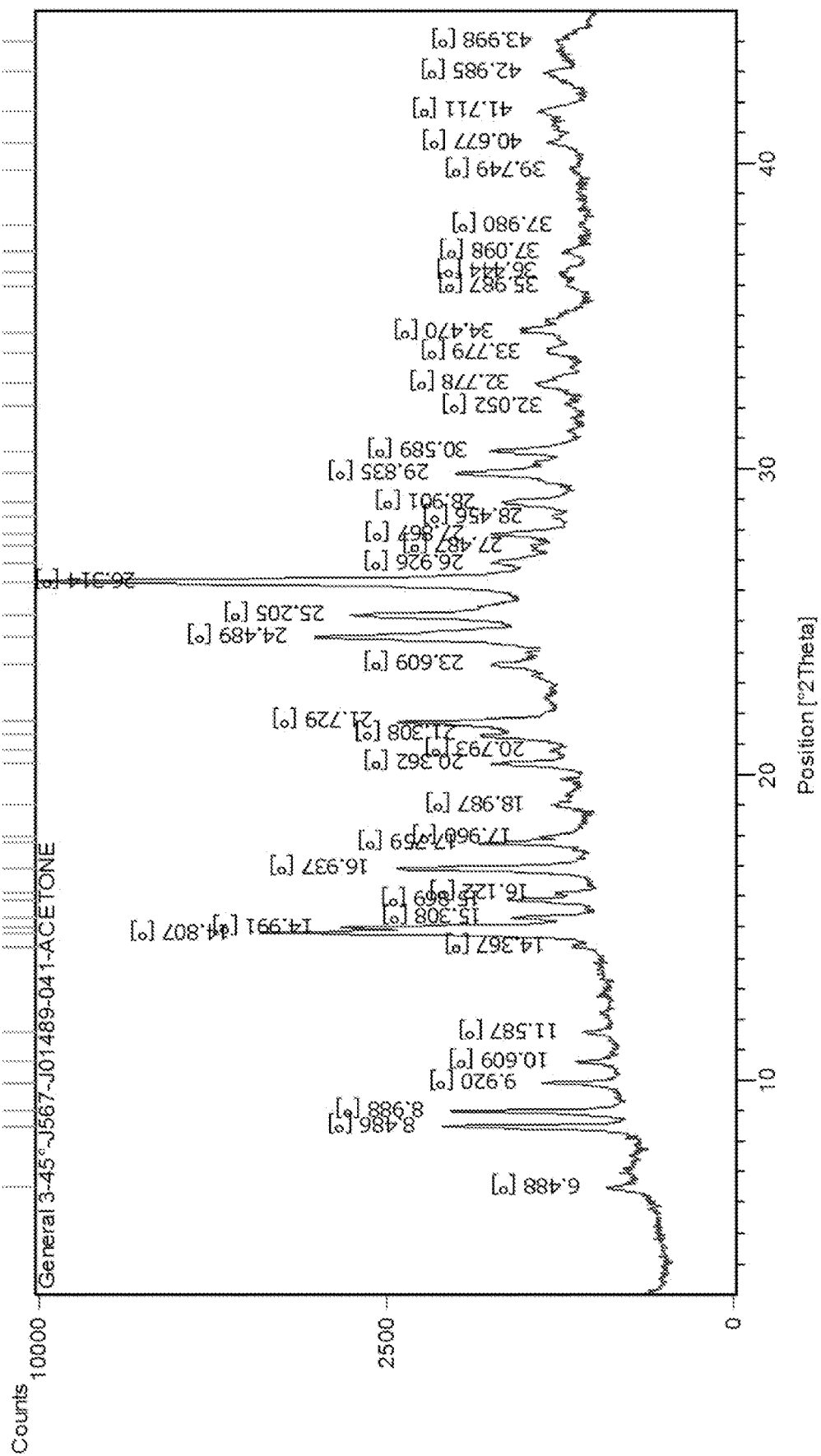
FIG. 12 shows an XRPD pattern obtained for LA1 meglumine salt, Form M.

In some embodiments, crystalline form M is characterized by an X-ray powder diffraction (XRPD) pattern substantially in accordance with FIG. 12, as determined on a diffractometer using Cu-Kα radiation. In some embodiments, the crystalline form M is characterized by a differential scanning calorimetry thermogram comprising an endothermic peak at around 294.5° C.

In another aspect, the invention provides a crystalline form N of a meglumine salt of a compound of Formula I:

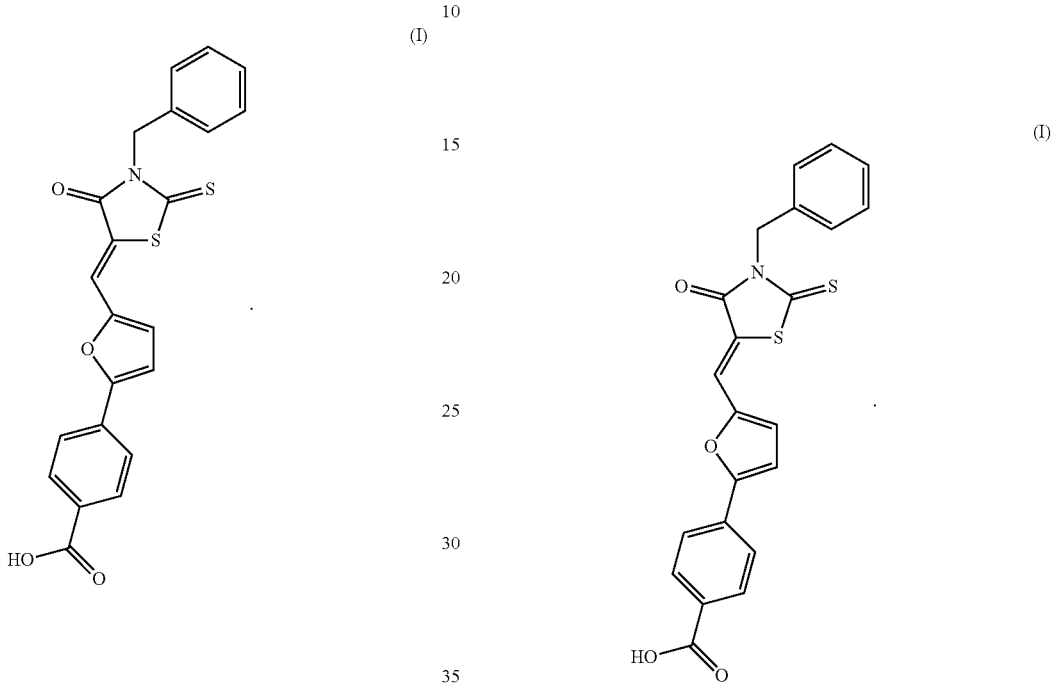

In some embodiments, crystalline form N is characterized by an X-ray powder diffraction (XRPD) pattern including at least three peaks selected from 4.3, 5.0, 5.4, 6.1, 7.5, 7.9, 8.9, 9.5, 10.0, 10.8, 11.4, 12.1, 12.5, 13.8, 14.3, 14.8, 15.6, 16.1, 16.7, 17.4, 18.1, 19.2, 19.5, 20.1, 20.9, 21.4, 21.5, 22.1, 22.5, 23.9, 24.6, 25.3, 26.3, 26.7, 27.1, 27.6, 28.2, 29.0, 30.4, 30.9, 32.0, 32.9, 33.9, 34.7, 36.9, 38.3, 39.1, 39.6, 40.2, and 41.4 °2θ, ±0.2 °2θ, as determined on a diffractometer using Cu-Kα radiation. For example, crystalline form N can include 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 such peaks.

In some embodiments, crystalline form N is characterized by an X-ray powder diffraction (XRPD) pattern including at least six peaks selected from 6.1, 7.9, 8.9, 9.5, 10.0, 12.5, 14.3, 14.8, 15.6, 16.1, 17.4, 18.1, 19.5, 20.9, 21.4, 21.5, 23.9, 24.6, 25.3, and 29.0 °2θ±0.2 °2θ, as determined on a diffractometer using Cu-Kα radiation.

In some embodiments, crystalline form N is characterized by an X-ray powder diffraction (XRPD) pattern including at least ten peaks selected from 6.1, 7.9, 8.9, 9.5, 10.0, 12.5, 14.3, 14.8, 15.6, 16.1, 17.4, 18.1, 19.5, 20.9, 21.4, 21.5, 23.9, 24.6, 25.3, and 29.0 °2θ±0.2 °2θ, as determined on a diffractometer using Cu-Kα radiation.

Figure 13:
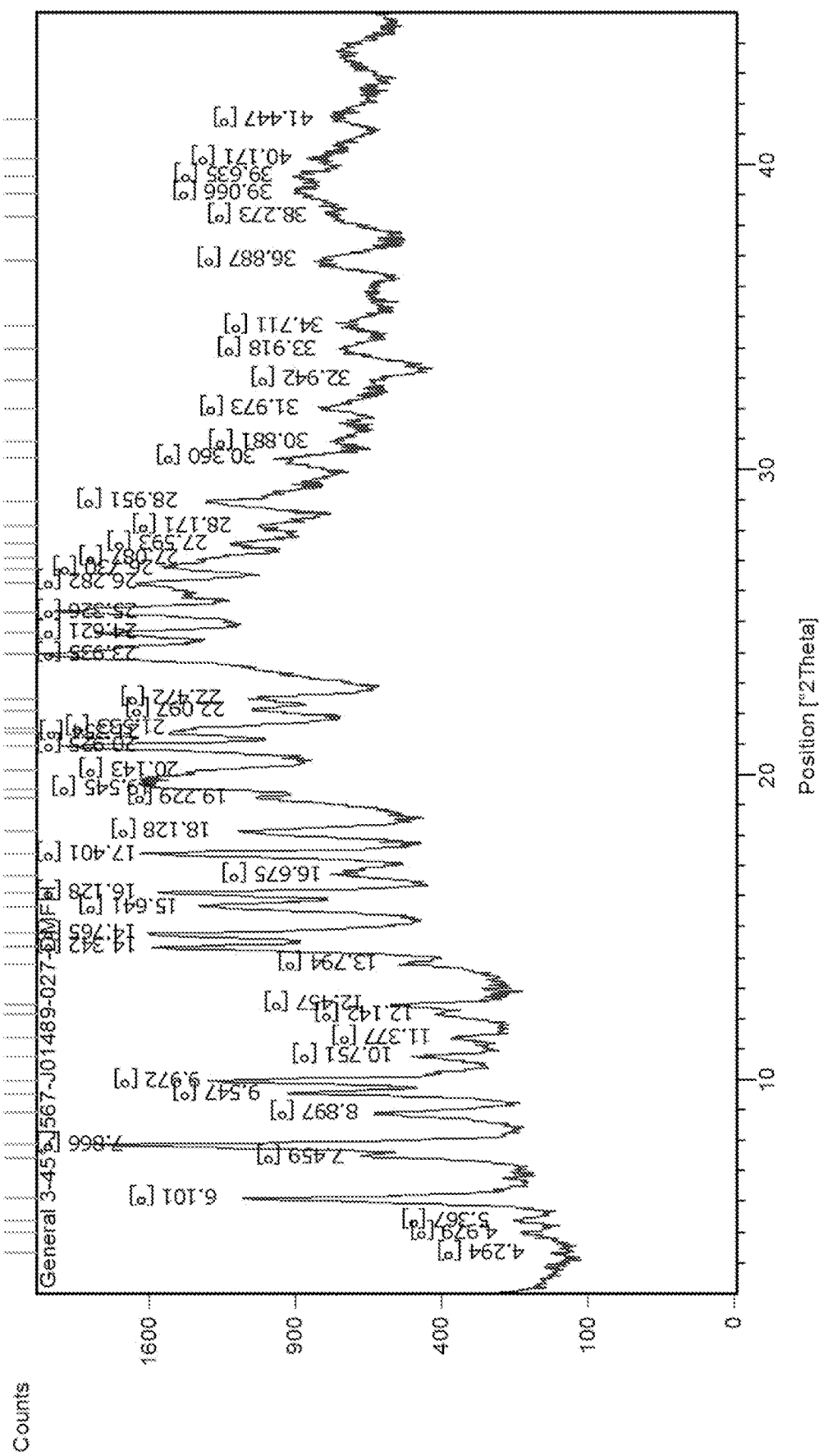
FIG. 13 shows an XRPD pattern obtained for LA1 meglumine salt, Form N.
Figures 14A, 14B, 14C, 14D, 14E:
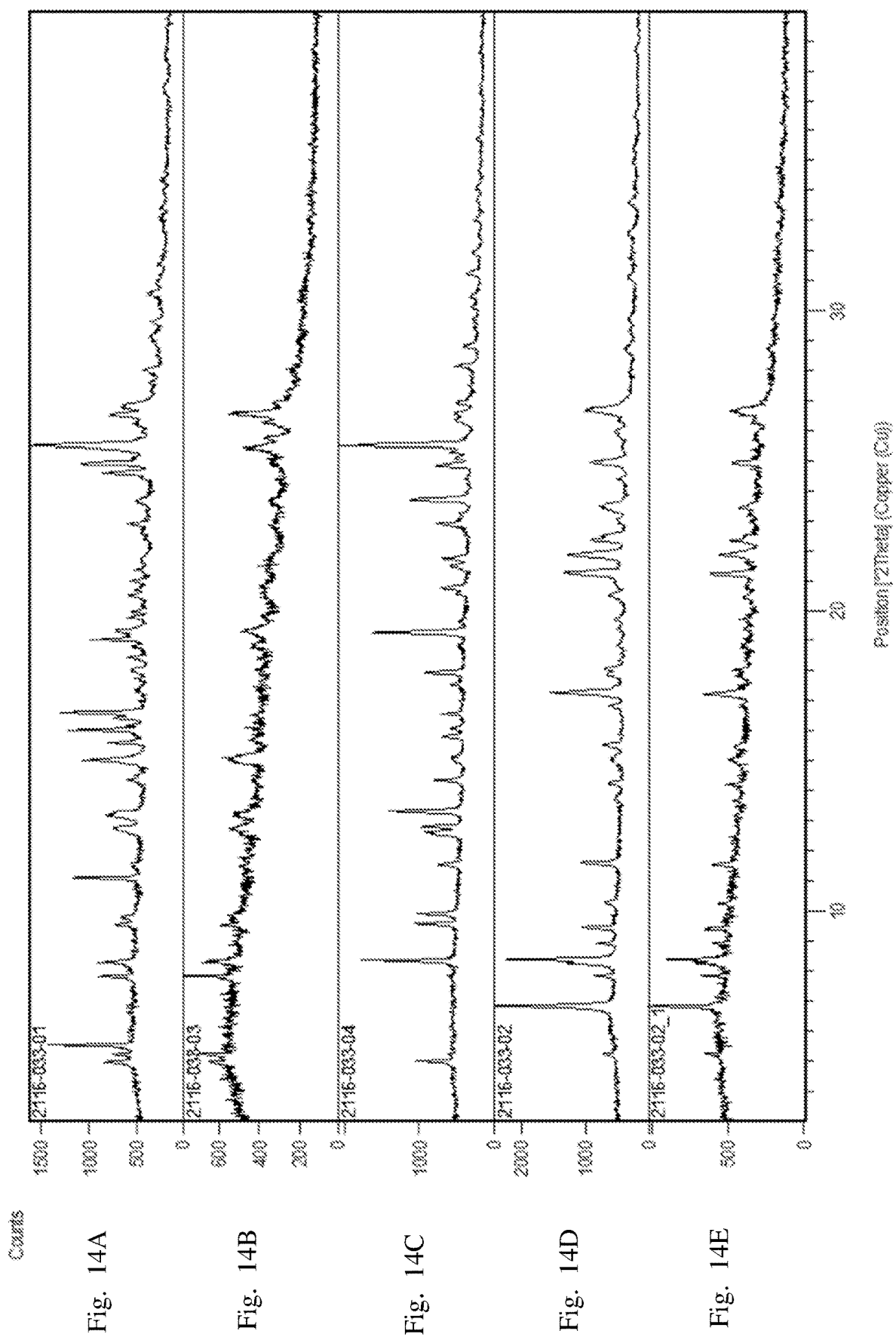
FIGS. 14A-E show XRPD patterns obtained for choline and meglumine salts prepared on a large scale: LA1 choline salt from ethanol (FIG. 14A); LA1 choline salt from ethanol (FIG. 14B); LA1 choline salt from acetone (FIG. 14C); LA1 meglumine salt from ethanol (FIG. 14D); LA1 meglumine salt from ethanol (FIG. 14E).

In some embodiments, crystalline form N is characterized by an X-ray powder diffraction (XRPD) pattern substantially in accordance with FIG. 13, as determined on a diffractometer using Cu-Kα radiation. In some embodiments, the crystalline form N is characterized by a differential scanning calorimetry thermogram comprising an endothermic peak at around 139.9° C.

In another aspect, the invention provides a crystalline form T of a meglumine salt of a compound of Formula I:

In some embodiments, crystalline form T is characterized by an X-ray powder diffraction (XRPD) pattern including at least three peaks selected from 6.9, 8.2, 8.4, 9.4, 11.6, 15.0, 15.1, 15.5, 17.2, 17.8, 18.1, 20.5, 21.3, 21.9, 22.3, 23.5, 25.0, and 26.7 °2θ±0.2 °2θ, as determined on a diffractometer using Cu-Kα radiation. For example, crystalline form T can include 3, 4, 5, 6, 7, 8, 9, 10, 11, 12, 13, 14, 15, 16, 17, or 18 such peaks.

In some embodiments, crystalline form T is characterized by an X-ray powder diffraction (XRPD) pattern including at least six peaks selected from 6.9, 8.4, 9.4, 11.6, 15.5, 17.2, 21.3, 21.9, 22.3, 23.5, 25.0, and 26.7 °2θ±0.2 °2θ, as determined on a diffractometer using Cu-Kα radiation.

In some embodiments, crystalline form T is characterized by an X-ray powder diffraction (XRPD) pattern including at least ten peaks selected from 5.3, 7.1, 10.7, 10.9, 16.1, 16.5, 17.7, 18.5, 20.3, 23.6, 24.9, and 27.2 °2θ±0.2 °2θ, as determined on a diffractometer using Cu-Kα radiation.

Figure 10:
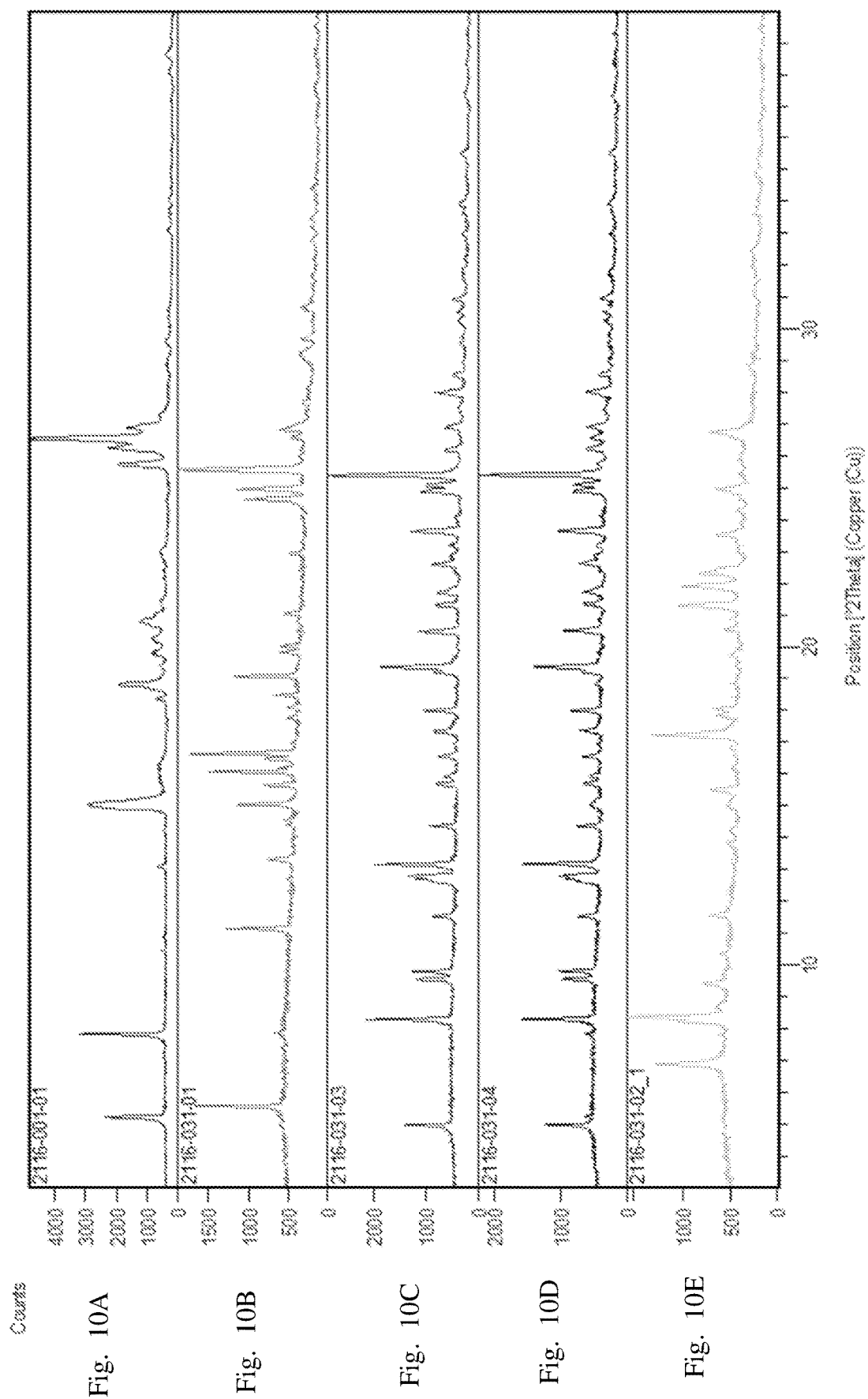
FIGS. 10A-E show XRPD patterns obtained for choline and meglumine salts prepared on small scale: disordered LA1, Form A (FIG. 10A); LA1 choline salt from ethanol: methyl tert-butyl ether (FIG. 10B); LA1 choline salt from acetone (FIG. 10C); LA1 choline salt, Form Q, from ethyl acetate (FIG. 10D); LA1 meglumine salt, Form T, from ethanol (FIG. 10E).

In some embodiments, crystalline form T is characterized by an X-ray powder diffraction (XRPD) pattern substantially in accordance with FIG. 10E, as determined on a diffractometer using Cu-Kα radiation.

In another aspect, the invention provides a solid form A of a compound of Formula I:

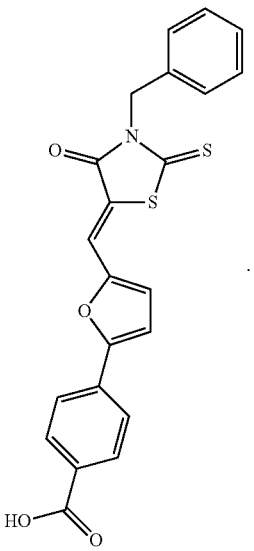

(I)

In some embodiments, the solid form A is characterized by an X-ray powder diffraction (XRPD) pattern including at least three peaks selected from 5.3, 7.8, 15.2, 18.7, 19.8, 20.3, 20.8, 25.7, 26.3, 26.5, and 26.9 °2θ±0.2 °2θ, as determined on a diffractometer using Cu-Kα radiation. For example, crystalline form A can include 3, 4, 5, 6, 7, 8, 9, 10, or 11 such peaks.

In some embodiments, the solid form A is characterized by an X-ray powder diffraction (XRPD) pattern including at least six peaks selected from 5.3, 7.8, 15.2, 18.7, 19.8, 20.3, 20.8, 25.7, 26.3, 26.5, and 26.9 °2θ±0.2 °2θ, as determined on a diffractometer using Cu-Kα radiation.

In some embodiments, the solid form A is characterized by an X-ray powder diffraction (XRPD) pattern including at least ten peaks selected from 5.3, 7.8, 15.2, 18.7, 19.8, 20.3, 20.8, 25.7, 26.3, 26.5, and 26.9 °2θ±0.2 °2θ, as determined on a diffractometer using Cu-Kα radiation.

Figure 2:
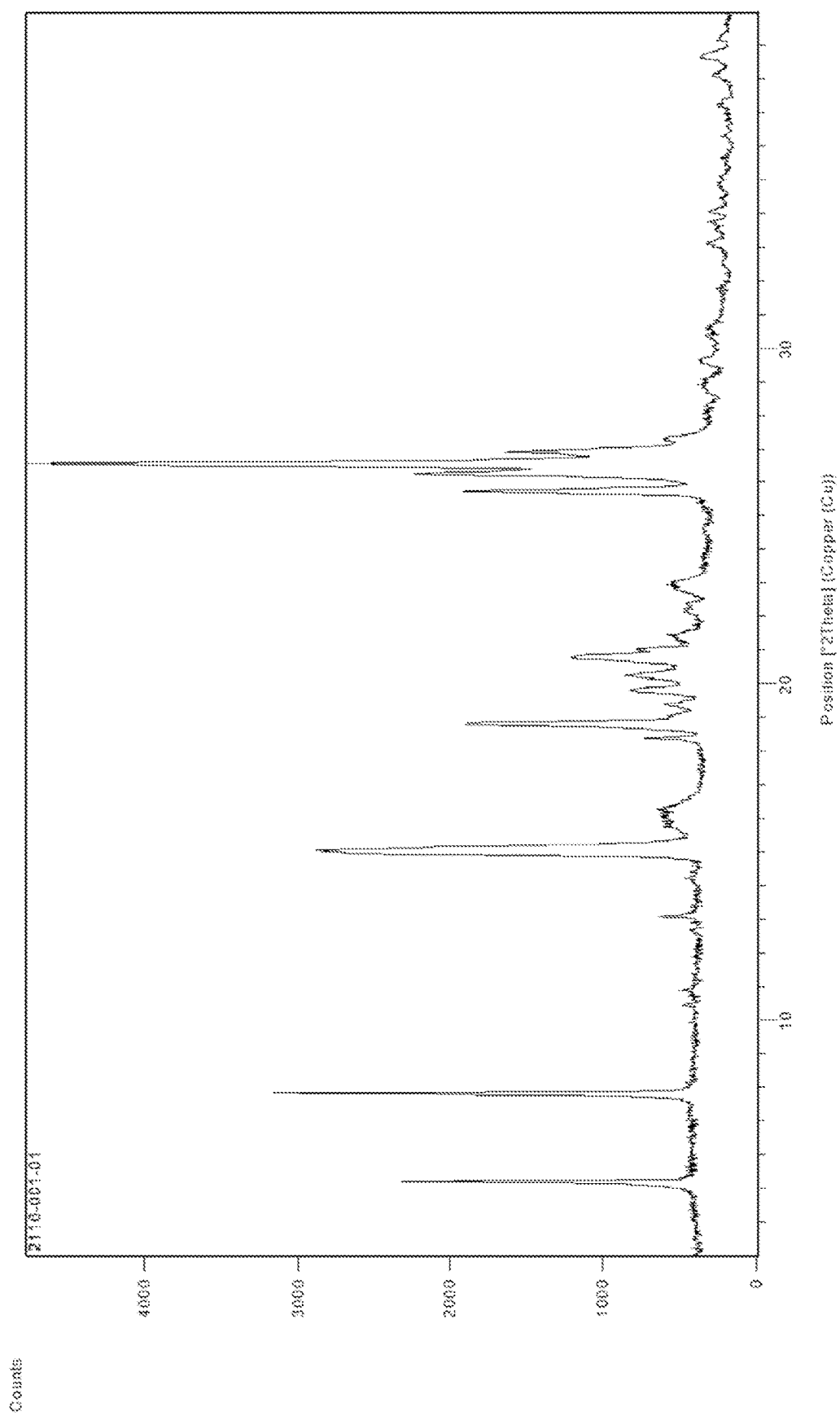
FIG. 2 shows an X-ray powder diffraction (XRPD) pattern obtained for LA1 free acid, Form A.

In some embodiments, the solid form A is characterized by an X-ray powder diffraction (XRPD) pattern substantially in accordance with FIG. 2, as determined on a diffractometer using Cu-Kα radiation.

In a related aspect, the invention provides methods for preparing salts and crystalline forms of LA1. In general, an LA1 salt is prepared by forming a mixture (i.e., a salt formation mixture) containing the LA1 free acid and at least one molar equivalent of a suitable base under conditions sufficient to form the salt. The mixture typically contains a solvent in which the LA1 free acid and/or the base is partially soluble or fully soluble. Examples of solvents that are useful for making LA1 salts include, but are not limited to, tetrahydrofuran, dioxane, methanol, ethanol, isopropanol, N,N-dimethylformamide, N-methylpyrollidone, methyl tert-butyl ether, acetone, ethyl acetate, dichloromethane, water, and mixture thereof. In some embodiments, the salt formation mixture contains at least one solvent selected from tetrahydrofuran and methanol. In some embodiments, the mixture contains tetrahydrofuran. In some embodiments, the mixture contains tetrahydrofuran and methanol. In some embodiments, the mixture contains acetone. In some embodiments, the mixture contains ethanol.

The salt formation mixture containing the LA1 free acid and the base can be formed under or held at any suitable temperature. Typically, the mixture is held at a temperature ranging from about 20° C. to about 80° C. for a time sufficient for salt formation. The mixture can be held, for example, at from about 20° C. to about 80° C. for anywhere from about 15 minutes to about 72 hours or longer. The mixture can be held at from about 40° C. to about 60° C. for from about 1 hour to about 48 hours, or at from about 40° C. to about 50° C. for from about 1 hour to about 16 hours.

In some embodiments, the salt formation mixture contains LA1 free acid, choline hydroxide, tetrahydrofuran, and methanol. In some embodiments, the ratio of tetrahydrofuran to methanol is 3:1 v:v. In some embodiments, crystalline form G is prepared by a process including forming a mixture containing one molar equivalent of LA1 free acid, one molar equivalent of choline hydroxide, and combination of tetrahydrofuran and methanol in a ratio of 3:1 v:v. In some embodiments, the process for preparing crystalline form G further includes agitating the mixture at from about 40° C. to about 50° C. for from about 24 hours to about 48 hours. In some embodiments, the process for preparing crystalline form G includes agitating the mixture at about 50° C. for at least about 24 hours. In some embodiments, the process for preparing crystalline form G includes removing the combination of tetrahydrofuran and methanol from the mixture by evaporation after formation of the crystalline form G.

In some embodiments, the salt formation mixture contains LA1 free acid, choline hydroxide, and tetrahydrofuran. In some embodiments, the ratio of tetrahydrofuran to methanol is 3:1 v:v. In some embodiments, crystalline form O is prepared by a process including forming a mixture containing one molar equivalent of LA1 free acid, one molar equivalent of choline hydroxide, and tetrahydrofuran. In some embodiments, the process for preparing crystalline form O further includes agitating the mixture at from about 20° C. to about 30° C. for from about 24 hours to about 48 hours. In some embodiments, the process for preparing crystalline form O includes agitating the mixture at no more than about 30° C. for at least about 24 hours.

In some embodiments, the salt formation mixture contains LA1 free acid, choline hydroxide, and ethyl acetate or acetone. In some embodiments, crystalline form Q is prepared by a process including forming a mixture containing one molar equivalent of LA1 free acid, one molar equivalent of choline hydroxide, and ethyl acetate. In some embodiments, the process for preparing crystalline form Q further includes agitating the mixture at from about 20° C. to about 30° C. for from about 12 hours to about 48 hours. In some embodiments, the process for preparing crystalline form Q includes agitating the mixture at no more than about 30° C. for at least about 12 hours. In some embodiments, the process for preparing crystalline form Q includes removing the ethyl acetate or acetone via vacuum filtration after formation of the crystalline form Q.

Preparing crystalline forms of LA1 choline salt can also include recrystallizing the LA1 choline salts. Recrystallization can be conducted used any suitable solvent, including a protic solvent (e.g., methanol, ethanol, isopropyl alcohol (IPA), n-butanol, and water), an aprotic solvent (e.g., isopropyl acetate, ethyl acetate, and acetone), or a mixture thereof. In some embodiments, preparing a crystalline form of LA1 choline salt includes recrystallizing the LA1 choline salt from a protic solvent. In some embodiments, preparing crystalline form R of LA1 choline salt includes recrystallizing LA1 choline salt from n-butanol. In some embodiments, preparing crystalline form S of LA1 choline salt includes recrystallizing LA1 choline salt from methanol.

In some embodiments, the salt formation mixture contains LA1 free acid, meglumine, tetrahydrofuran, and methanol. In some embodiments, the ratio of tetrahydrofuran to methanol is 2:1 v:v. In some embodiments, crystalline form H is prepared by a process including forming a mixture containing one molar equivalent of LA1 free acid, one molar equivalent of meglumine, and a combination of tetrahydrofuran and methanol in a ratio of 2:1 v:v. In some embodiments, the process for preparing crystalline form H further includes agitating the mixture at from about 40° C. to about 50° C. for from about 24 hours to about 48 hours. In some embodiments, the process for preparing crystalline form H includes agitating the mixture at about 50° C. for at least about 24 hours. In some embodiments, the process for preparing crystalline form H includes removing the combination of tetrahydrofuran and methanol from the mixture by evaporation after formation of the crystalline form H.

In some embodiments, the salt formation mixture contains LA1 free acid, meglumine, and ethanol. In some embodiments, crystalline form T is prepared by a process including forming a mixture containing one molar equivalent of LA1 free acid, one molar equivalent of meglumine, and ethanol. In some embodiments, the process for preparing crystalline form T further includes agitating the mixture at from about 40° C. to about 50° C. for from about 24 hours to about 48 hours. In some embodiments, the process for preparing crystalline form T includes agitating the mixture at about 40° C. for at least about 24 hours. In some embodiments, the process for preparing crystalline form T includes removing the ethanol from the mixture by vacuum filtration after formation of the crystalline form T and isolating at least a portion of crystalline form T. In some embodiments, the process for preparing crystalline form T further includes washing the isolated crystalline form T with methyl tert-butyl ether.

Preparing crystalline forms of LA1 meglumine salt can also include recrystallizing the LA1 meglumine salts. Recrystallization can be conducted used any suitable solvent, including a protic solvent (e.g., methanol, ethanol, isopropyl alcohol (IPA), n-butanol, and water), an aprotic solvent (e.g., N,N-dimethyl formamide (DMF), dimethylsulfoxide (DMSO), isopropyl acetate, ethyl acetate, and acetone), or a mixture thereof. In some embodiments, preparing a crystalline form of LA1 meglumine salt includes recrystallizing the LA1 meglumine salt from an aprotic solvent. In some embodiments, preparing crystalline form L of LA1 meglumine salt includes recrystallizing LA1 choline salt from isopropyl acetate. In some embodiments, preparing crystalline form M of LA1 meglumine salt includes recrystallizing LA1 choline salt from acetone. In some embodiments, preparing crystalline form N of LA1 meglumine salt includes recrystallizing LA1 choline salt from DMF.

IV. Pharmaceutical Compositions

In a related aspect, the invention provides pharmaceutical compositions for the administration of the salts and crystalline forms described herein. The pharmaceutical compositions can be prepared by any of the methods well known in the art of pharmacy and drug delivery. In general, methods of preparing the compositions include the step of bringing the active ingredient into association with a carrier containing one or more accessory ingredients. The pharmaceutical compositions are typically prepared by uniformly and intimately bringing the active ingredient into association with a liquid carrier or a finely divided solid carrier or both, and then, if necessary, shaping the product into the desired formulation. The compositions can be conveniently prepared and/or packaged in unit dosage form.

The pharmaceutical compositions can be in the form of sterile injectable aqueous or oleaginous solutions and suspensions. Sterile injectable preparations can be formulated using non-toxic parenterally-acceptable vehicles including water, Ringer's solution, and isotonic sodium chloride solution, and acceptable solvents such as 1,3-butane diol. In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables.

Aqueous suspensions contain the active materials in admixture with excipients including, but not limited to: suspending agents such as sodium carboxymethylcellulose, methylcellulose, oleagino-propylmethylcellulose, sodium alginate, polyvinyl-pyrrolidone, gum tragacanth and gum acacia; dispersing or wetting agents such as lecithin, polyoxyethylene stearate, and polyethylene sorbitan monooleate; and preservatives such as ethyl, n-propyl, and p-hydroxybenzoate.

Oily suspensions can be formulated by suspending the active ingredient in a vegetable oil, for example, *arachis* oil, olive oil, sesame oil or coconut oil, or in a mineral oil such as liquid paraffin. The oily suspensions can contain a thickening agent, for example beeswax, hard paraffin or cetyl alcohol. These compositions can be preserved by the addition of an anti-oxidant such as ascorbic acid.

Dispersible powders and granules (suitable for preparation of an aqueous suspension by the addition of water) can contain the active ingredient in admixture with a dispersing agent, wetting agent, suspending agent, or combinations thereof. Additional excipients can also be present.

The pharmaceutical compositions of the invention can also be in the form of oil-in-water emulsions. The oily phase can be a vegetable oil, for example olive oil or *arachis* oil, or a mineral oil, for example liquid paraffin or mixtures of these. Suitable emulsifying agents can be naturally-occurring gums, such as gum acacia or gum tragacanth; naturally-occurring phospholipids, such as soy lecithin; esters or partial esters derived from fatty acids and hexitol anhydrides, such as sorbitan monooleate; and condensation products of said partial esters with ethylene oxide, such as polyoxyethylene sorbitan monooleate.

Pharmaceutical compositions containing the salts and crystalline forms described herein can also be in a form suitable for oral use. Suitable compositions for oral administration include, but are not limited to, tablets, troches, lozenges, aqueous or oily suspensions, dispersible powders or granules, emulsions, hard or soft capsules, syrups, elixirs, solutions, buccal patches, oral gels, chewing gums, chewable tablets, effervescent powders, and effervescent tablets. Compositions for oral administration can be formulated according to any method known to those of skill in the art. Such compositions can contain one or more agents selected from sweetening agents, flavoring agents, coloring agents, antioxidants, and preserving agents in order to provide pharmaceutically elegant and palatable preparations.

Tablets generally contain the active ingredient in admixture with non-toxic pharmaceutically acceptable excipients, including: inert diluents, such as cellulose, silicon dioxide, aluminum oxide, calcium carbonate, sodium carbonate, glucose, mannitol, sorbitol, lactose, calcium phosphate, and sodium phosphate; granulating and disintegrating agents, such as corn starch and alginic acid; binding agents, such as polyvinylpyrrolidone (PVP), cellulose, polyethylene glycol (PEG), starch, gelatin, and acacia; and lubricating agents such as magnesium stearate, stearic acid, and talc. The tablets can be uncoated or coated, enterically or otherwise, by known techniques to delay disintegration and absorption in the gastrointestinal tract and thereby provide a sustained action over a longer period. For example, a time delay material such as glyceryl monostearate or glyceryl distearate can be employed. Tablets can also be coated with a semi-permeable membrane and optional polymeric osmogents according to known techniques to form osmotic pump compositions for controlled release.

Compositions for oral administration can be formulated as hard gelatin capsules wherein the active ingredient is mixed with an inert solid diluent (such as calcium carbonate, calcium phosphate, or kaolin), or as soft gelatin capsules wherein the active ingredient is mixed with water or an oil medium (such as peanut oil, liquid paraffin, or olive oil).

The salts and crystalline forms described herein can also be administered topically as a solution, ointment, cream, gel, suspension, mouth washes, eye-drops, and the like. Still further, transdermal delivery of the salts and crystalline forms can be accomplished by means of iontophoretic patches and the like. The compound can also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter and polyethylene glycols.

In some embodiments, a salt or crystalline form described herein is administered via intraperitoneal injection. In some embodiments, the salt or crystalline form is administered orally. In some embodiments, the salt or crystalline form is administered intravenously.

LA1 can be used in combination with drugs selected from, but not limited to, the group consisting of 5-fluorouracil, AZD8055, bevacizumab, bortezomib, cetuximab, cyclophosphamide, docetaxel, gemcitabine, imatinib, ipilimumab, lapatinib, paclitaxel, pertuzumab, rapamycin, sipuleucel-T, sorafenib, sunitinib, trastuzumab, temsirolimus, vemurafenib, taxol, paclitaxel, abiraterone, steroids, corticosteroids, prednisone, NSAIDs, mitomycin, androgens, antiandrogens, estrogens, antiestrogens, statins, CTLA-4 inhibitors, anti-CTLA-4 antibodies, B7 modulators, abatacept, rituximab, belatacept, benlumimab, PD-1 modulators, anti-PD1 antibodies, PDL1 modulators, anti-PDL1 antibodies, IDO1 inhibitors and modulators, CSF1 modulators, CSF1R modulators, anti-CSF1R antibodies, CD47 modulators and inhibitors, CD206 modulators and inhibitors, TNFa inhibitors and modulators, anti-TNFa antibodies, cytokine modulators, anti-cytokine antibodies, interleukin modulators and inhibitors, anti-interleukin antibodies, anti-CCL2, anti-CCL4, CXCR-4 inhibitors, anti-CXCR4, anti-IL17, and anti-IL23.

The pharmaceutical compositions of the invention can also include micronized LA1 or a micronized LA1 salt or a micronized crystalline form of an LA1 salt. In general, compositions containing micronized LA1 contain particles consisting essentially of LA1 with average diameters below 50 µm. The average diameter of the LA1 particles can be, for example, below 45 µm, below 40 µm, below 35 µm, below 30 µm, below 25 µm, or below 20 µm. The average diameter of the LA1 particles can be from about 10 µm to about 49 µm, or from about 10 µm to about 45 µm, or from about 15 µm to about 40 µm, or from about 20 µm to about 35 µm, or from about 25 µm to about 30 µm. The average diameter of the LA1 particles can be about 15, 16, 17, 18, 19, 20, 21, 22, 23, 24, or about 25 µm. In some embodiments, the particles consist essentially of micronized LA1 in its free-acid form. In some embodiments, the particles consist essentially of a micronized LA1 salt, as described herein, in amorphous or crystalline form.

V. Methods of Treatment

The salts and crystalline forms described herein can be used for treating a disease or condition associated with the activity of β2 integrins. In certain embodiments, such a disease or condition is selected from inflammation (including, but not limited to, acute and chronic inflammation), inflammatory skin diseases, immune-related disorders, autoimmune diseases, burn, immune deficiency, acquired immune deficiency syndrome (AIDS), myeloperoxidase deficiency, Wiskott-Aldrich syndrome, chronic kidney disease, chronic granulomatous disease, hyper-IgM syndromes, leukocyte adhesion deficiency, iron deficiency, Chediak-Higashi syndrome, severe combined immunodeficiency, diabetes, obesity, hypertension, HIV, wound-healing, remodeling, scarring, fibrosis, stem cell therapies, cachexia, encephalomyelitis, multiple sclerosis, psoriasis, lupus, rheumatoid arthritis, immune-related disorders, radiation injury, transplantation, cell transplantation, cell transfusion, organ transplantation, bone marrow transplantation, organ preservation, cell preservation, asthma, irritable bowel disease, irritable bowel syndrome, ulcerative colitis, colitis, bowel disease, cancer, leukemia, ischemia-reperfusion injury, stroke, neointimal thickening associated with vascular injury, bullous pemphigoid, neonatal obstructive nephropathy, familial hypercholesterolemia, atherosclerosis, dyslipidemia, aortic aneurisms, arteritis, vascular occlusion, including cerebral artery occlusion, complications of coronary by-pass surgery, myocarditis, including chronic autoimmune myocarditis and viral myocarditis, heart failure, including chronic heart failure (CHF), cachexia of heart failure, myocardial infarction, stenosis, restenosis after heart surgery, silent myocardial ischemia, post-implantation complications of left ventricular assist devices, thrombophlebitis, vasculitis, including Kawasaki's vasculitis, giant cell arteritis, Wegener's granulomatosis, traumatic head injury, post-ischemic-reperfusion injury, post-ischemic cerebral inflammation, ischemia-reperfusion injury following myocardial infarction, cardiovascular disease, glaucoma, macular degeneration, uveitis, and graft-versus-host disease, neurological conditions, Alzheimer's disease, Parkinson's disease, dermatitis, pain (including chronic pain), and cancer, including primary tumors and metastatic tumors, such as breast cancer, prostate cancer, melanoma, lung cancer and pancreatic cancer. In certain such embodiments, the disease or condition associated with the activity of β2 integrins is selected from inflammatory kidney disease, a condition that affects millions of people in the world and leads to renal failure, and restenosis, a common problem in people who have undergone angioplasty, one of the most common procedures in interventional cardiology. In certain such embodiments, the β2 integrin is CD11b/CD18.

The salts and crystalline forms described herein can be used for treating cancer or reducing tumors in patients. In certain embodiments, the salts and crystalline forms modulate tumor infiltration of leukocytes. Tumors secrete inflammatory cytokines to recruit cells expressing β2 integrins, such as CD11b/CD18, to facilitate neovascularization. During cancer treatments, including via chemotherapy and irradiation, tumors recruit large numbers of specific leukocytes or bone marrow-derived cells that restore tumor vasculature and allow tumor re-growth and recurrence. Therefore, the compounds and methods of this invention are useful in reducing activity, such as infiltration, of such cells. In addition, activating CD11b can enhance anti-tumor immune responses. Accordingly, compounds that agonize CD11b, including the salts and crystalline forms described herein as well as other compounds, can be used to target and exploit immunomodulatory pathways for anti-tumor therapy. In some embodiments, the salts and crystalline forms described herein are useful in enhancing the response of other cancer treatments, such as chemotherapy, antibody therapy, radiation therapy, and cell-based therapies.

In some embodiments, the salts and crystalline forms described can be used to decrease leukocyte recruitment upon injury, inflammation, bacterial infection, viral infection, or other diseases and conditions in mammals. In some embodiments, the salts and crystalline forms can be used to reduce organ injury, including neointimal hyperplasia upon arterial injury. In some embodiments, the salts and crystalline forms can be used to preserve organ function upon acute organ injury, such as ischemia-reperfusion injury. For example, the salts and crystalline forms can preserve kidney function upon acute kidney injury. In some embodiments, the salts and crystalline forms described herein can be used to preserve kidney function upon glomerular nephritis or nephrosis.

In some embodiments, the salts and crystalline forms described herein can be used to modulate the function of inflammatory cells, such as lymphocytes and leukocytes. The compounds can be used to treat integrin-mediated inflammation in a number of organs and tissues including, but not limited to, integrin-mediated inflammation of the eye, the brain, the skin, the liver, and the kidney. For example, the salts and crystalline forms can be used to induce graft tolerance in a recipient animal. Grafts can include bone marrow, bone marrow cells, stem cells, immune cells, engineered cells, organs, tissues or other cells. Similarly, the salts and crystalline forms can reduce graft-vs-host disease in the recipient. Thus, the salts and crystalline forms can improve transplantation outcomes.

Accordingly, the invention provides methods for preventing or treating a β2 integrin-mediated condition or disease in a patient comprising administering to said patient a therapeutically effective amount of a salt or crystalline form described herein. In certain embodiments, the β2 integrin-mediated condition or disease is a CD11b/CD18-mediated condition or disease.

LA1 has also shown efficacy in an adenosine A2A receptor agonist assay and a glucocorticoid receptor agonist assay, indicating that LA1 and the salts and crystalline forms described herein can be used to treat conditions related to the activity of those receptors.

In one aspect, the invention provides a method for treating cancer. The method comprises administering to a subject in need thereof:

a therapeutically effective amount of a compound according to Formula I

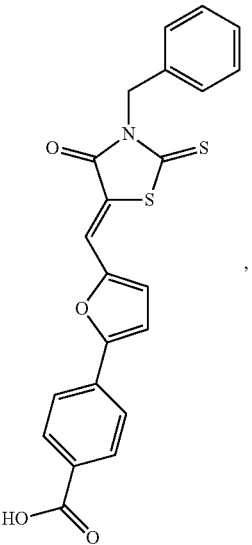

(I)

or a pharmaceutically acceptable salt thereof, and a therapeutically effective amount of an immune checkpoint inhibitor.

In some embodiments, the method comprises administering to the subject a pharmaceutically acceptable salt of the compound according to Formula I. In some embodiments, the salt is a meglumine salt or a choline salt. In some such embodiments, the invention includes administering a salt or crystalline form of LA1 as described herein.

In some embodiments, the immune checkpoint inhibitor inhibits the activity of one or more targets selected from the group consisting of CTLA-4, 4-1BB (CD137), 4-1BBL (CD137L), PDL1, PDL2, PD1, B7-H3, B7-H4, BTLA, HVEM, TIM3, GAL9, LAG3, TIM3, B7H3, B7H4, VISTA, KIR, 2B4, CD160, IDO1/IDO2 (indoleamine 2,3-dioxygenase), and CGEN-15049.

In some embodiments, the immune checkpoint inhibitor is a protein that binds to one or more targets selected from the group consisting of CTLA-4, PDL1, PDL2, PD1, B7-H3, B7-H4, BTLA, HVEM, TIM3, GAL9, LAG3, TIM3, B7H3, B7H4, VISTA, KIR, 2B4, CD160, and CGEN-15049.

In some embodiments, the protein is selected from the group consisting of an antibody and an antigen-binding antibody fragment. In some embodiments, the protein is selected from the group consisting of a CTLA-4 antibody, an OX40 antibody, a PD-L1 antibody, a PD1 antibody, and a BY55 antibody. In some embodiments, the protein is a CTLA-4 antibody. In some embodiments, the protein is a PD1 antibody.

In some embodiments, the protein is selected from the group consisting of tremelimumab, MEDI4736, MK-3475, nivolumab, CT-011, AMP224, BMS-936559, MPLDL3280A, MSB0010718C, and ipilimumab.

In some embodiments, the cancer is associated with expression of one or more leukocyte markers in the subject. In some embodiments, the leukocyte markers are selected from the group consisting of CD11b/CD18, IDO 1/2, TDO, CSF1R, CD14, CD16, CD68, VEGFR, and SIRPa.

In some embodiments, the cancer expresses one or more targets for β2 integrins. In some embodiments, the targets are selected from the group consisting of ICAM-1, VCAM-1, fibronectin, vironectin, fibrinogen, and complement fragments.

In some embodiments, the cancer is selected from the group consisting of a melanoma, a sarcoma, a lymphoma, a glioma, a leukemia, pancreatic cancer, a tenosynovial giant-cell tumor, breast cancer, ovarian cancer, prostate cancer, colon cancer, stomach cancer, and lung cancer. In some embodiments, the cancer is a melanoma. In some embodiments, the cancer patient has also been diagnosed with an autoimmune disease (e.g., multiple sclerosis, lupus, rheumatoid arthritis, Crohn's disease, or ulcerative colitis).

In another aspect, the invention provides a method for treating melanoma. The method comprises administering to a subject in need thereof:

a therapeutically effective amount of a compound according to Formula IV

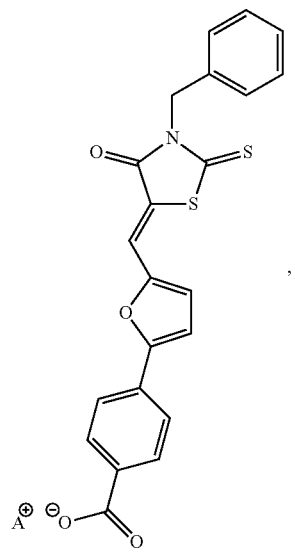

(IV)

wherein A⁺ is selected from the group consisting of a choline cation and a meglumine cation, and a therapeutically effective amount of a PD1 antibody.

In another aspect, the invention provides a method for treating cancer which includes administering to a subject in need thereof:

a therapeutically effective amount of a compound according to Formula I

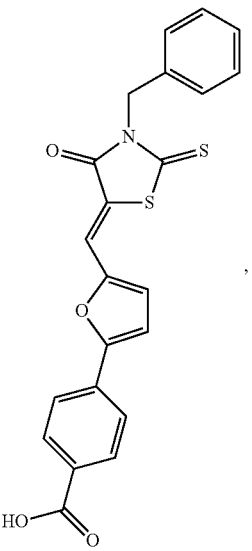

(I)

or a pharmaceutically acceptable salt thereof, and a therapeutically effective amount of an agent that targets myeloid cells.

In some embodiments, the agent that targets myeloid cells inhibits the activity of one or more targets selected from the group consisting of CSF1R, IDO1/2, TDO, CCR2, CCL2, CXCR4, JAK1/2/3/4/5, PI3Kg, integrin β1, integrin α4β1 (VLA4), VEGFR.

In some embodiments, the agent that targets myeloid cells increases the activity of SIRPa.

In some embodiments of any one of the preceding aspects, the method further comprises detecting one or more leukocyte markers in a sample obtained from the subject, thereby identifying the subject as needing the treatment. In some such embodiments, the leukocyte markers are selected from the group consisting of CD11b/CD18, IDO1/2, TDO, CSF1R, CD14, CD16, CD68, VEGFR, and SIRPa. In some such embodiments, the marker is CD11b/CD18.

In some embodiments of any one of the preceding aspects, the method further comprises monitoring treatment efficacy by imaging tumor cells with macrophage-targeted imaging agents. In some embodiments of any on the preceding aspects, the method further comprises monitoring treatment efficacy by monitoring levels of one or more macrophage markers in the subject.

In a related aspect, the invention provides a method for reducing CD11b+ leukocytes in a tumor. The method comprises administering to a subject in need thereof:

an effective amount of a compound according to Formula I

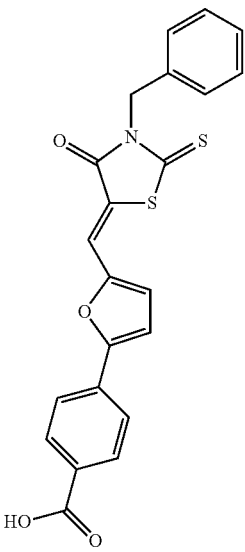

or a pharmaceutically acceptable salt thereof, and
an effective amount of an agent selected from the group consisting of an immune checkpoint inhibitor, an agent that targets myeloid cells, and combinations thereof.

In some embodiments, the CD11b+ leukocytes are myeloid cells. In some embodiments, the CD11b+ leukocytes are macrophages. In some embodiments, the CD11b+ leukocytes are neutrophils.

In some embodiments, the ratio of anti-tumorigenic to pro-tumorigenic macrophages in the tumor tissue is changed.

In some embodiments, the M1/M2 ratio is changed in the tumor. In some such embodiments, the macrophages are polarized toward an M1 phenotype.

In some embodiments, the invention provides a method for preventing tumor metastasis in a subject having cancer. The method includes:
administering to a subject in need thereof an effective amount of a compound according to Formula I

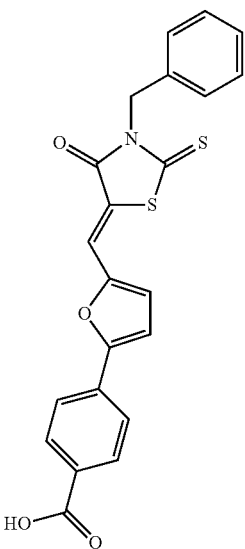

or a pharmaceutically acceptable salt thereof, and
reducing infiltration of CD11b+ leukocytes in a potential metastasis site in the subject.

In some embodiments, the method for preventing tumor metastasis further includes administering an effective amount of an agent selected from the group consisting of an immune checkpoint inhibitor, an agent that targets myeloid cells, and combinations thereof.

The salts and crystalline forms described herein can be administered at any suitable dose in the methods of the invention. In general, a salt or crystalline form is administered at a dose ranging from about 0.1 milligrams to about 2000 milligrams per kilogram of a subject's body weight (i.e., about 0.1-2000 mg/kg). The dose of the salt or crystalline form can be, for example, about 0.1-1000 mg/kg, or about 1-500 mg/kg, or about 25-250 mg/kg, or about 50-100 mg/kg, or about 10-100 mg/kg. The dose of the salt or crystalline form can be about 1, 2, 3, 4, 5, 10, 15, 20, 25, 30, 35, 40, 45, 50, 55, 60, 65, 70, 75, 85, 90, 95, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950 or 2000 mg/kg. The dose of the salt or crystalline form can be administered at a dose below about 1, below about 2, below about 3, below about 4, below about 5, below about 10, below about 15, below about 20, below about 25, below about 30, below about 35, below about 40, below about 45, below about 50, below about 55, below about 60, below about 65, below about 70, below about 75, below about 85, below about 90, below about 95, below about 100, below about 150, below about 200, below about 250, below about 300, below about 350, below about 400, below about 450, below about 500, below about 550, below about 600, below about 650, below about 700, below about 750, below about 800, below about 850, below about 900, below about 950, or below about 1000 mg/kg. In some embodiments, the salt or crystalline form is administered at a dose below 200 mg of compound per kg of the subject's body weight (200 mg/kg). In some embodiments, the salt or crystalline form is administered at a dose below 100 mg/kg. In some embodiments, the salt or crystalline form is administered at a dose below 50 mg/kg. In some embodiments, the salt or crystalline form is administered at a dose below 20 mg/kg.

Immune checkpoint inhibitors can be administered at any suitable dose in the methods of the invention. In certain embodiments, an antibody immune checkpoint inhibitor is administered at a dose ranging from about 0.1 milligrams to about 100 milligrams per kilogram of a subject's body weight (i.e., about 0.1-100 mg/kg). The dose of the antibody immune checkpoint inhibitor can be, for example, about 0.1-50 mg/kg, or about 1-10 mg/kg. The dose of the antibody immune checkpoint inhibitor can be about 1, 2, 3, 4, 5, 6, 7, 8, 9, 10, 11, 12, 13, 14, 15, 16, 17, 18, 19, or 20 mg/kg.

The dosages can be varied depending upon the requirements of the patient, the severity of the β2 integrin-mediated disorder or condition being treated, and the particular formulation being administered. The dose administered to a patient should be sufficient to result in a beneficial therapeutic response in the patient. The size of the dose will also be determined by the existence, nature, and extent of any adverse side-effects that accompany the administration of the drug in a particular patient. Determination of the proper dosage for a particular situation is within the skill of the typical practitioner. The total dosage can be divided and administered in portions over a period of time suitable to treat to the integrin-mediated condition.

Administration of a salt or crystalline form described herein can be conducted for a period of time which will vary depending upon the nature of the particular the β2 integrin-mediated disorder or condition, its severity and the overall condition of the patient. Administration can be conducted, for example, hourly, every 2 hours, three hours, four hours, six hours, eight hours, or twice daily including every 12 hours, or any intervening interval thereof. Administration can be conducted once daily, or once every 36 hours or 48 hours, or once every month or several months. Following treatment, a patient can be monitored for changes in his or her condition and for alleviation of the symptoms of the β2 integrin-mediated disorder or condition. The dosage of the salt or crystalline form can either be increased in the event the patient does not respond significantly to a particular dosage level, or the dose can be decreased if an alleviation of the symptoms of the β2 integrin-mediated disorder or condition is observed, or if the disorder or condition has been ablated, or if unacceptable side effects are seen with a particular dosage.

A therapeutically effective amount of a salt or crystalline form described herein can be administered to the subject in a treatment regimen comprising intervals of at least 1 hour, or 6 hours, or 12 hours, or 24 hours, or 36 hours, or 48 hours between dosages. Administration can be conducted at intervals of at least 72, 96, 120, 168, 192, 216, or 240 hours, or the equivalent amount of days. The dosage regimen can consist of two or more different interval sets. For example, a first part of the dosage regimen can be administered to a subject multiple times daily, daily, every other day, or every third day. The dosing regimen can start with dosing the subject every other day, every third day, weekly, biweekly, or monthly. The first part of the dosing regimen can be administered, for example, for up to 30 days, such as 7, 14, 21, or 30 days. A subsequent second part of the dosing regimen with a different interval administration administered weekly, every 14 days, or monthly can optionally follow, continuing for 4 weeks up to two years or longer, such as 4, 6, 8, 12, 16, 26, 32, 40, 52, 63, 68, 78, or 104 weeks. Alternatively, if the (32 integrin-mediated disorder or condition goes into remission or generally improves, the dosage may be maintained or kept at lower than maximum amount. If the disorder or condition relapses, the first dosage regimen can be resumed until an improvement is seen, and the second dosing regimen can be implemented again. This cycle can be repeated multiple times as necessary.

In certain embodiments, an LA1 salt and an immune checkpoint inhibitor are administered in synergistic amounts; in such cases the effect of the agents when administered in combination is greater than the additive effect of the compounds when administered alone as a single agent. In some embodiments, the synergistic effect is obtained by administering the LA1 salt and the checkpoint inhibitor at concentrations below the maximally effective concentration of the drugs when administered as single agents. The synergistic amounts can depend on factors including, but not limited to, the particular LA1 salt or crystalline form, the particular immune checkpoint inhibitor, the condition (e.g., cancer type) being treated, and the route and frequency of administration. Synergy can be observed in terms of lower cytotoxicity, increased anti-proliferative and/or anti-infective effect, or some other beneficial effect of the combination compared with the individual components.

In some embodiments, LA1 or an LA1 salt as described above is administered to the subject in an amount ranging from about 1 mg/kg to about 2000 mg/kg. In some such embodiments, the immune checkpoint inhibitor is administered in a synergistic amount with the LA1 or the LA1 salt. In some of these embodiments, LA1 or the LA1 salt is administered orally to the subject.

In some embodiments, LA1 or an LA1 salt is administered to the subject in an amount ranging from about 2 mg/kg to about 100 mg/kg. In some such embodiments, the immune checkpoint inhibitor is administered in a synergistic amount with the LA1 or the LA1 salt. In some of these embodiments, LA1 or the LA1 salt is administered orally to the subject.

LA1 can modulate the release of one or more secreted factors, including but not limited to cytokines and chemokines, from leukocytes. Cytokines include pro-inflammatory cytokines (e.g., interleukin (IL)-1, tumor necrosis factor (TNF)) and anti-inflammatory cytokines (e.g., IL-4, IL-10, IL-13). In certain embodiments, administration of a salt or crystalline form described herein results in modulation of cytokine expression (or other soluble factor) by LA1. In some embodiments, the cytokine is selected from IL-10, IL-6, and IL-10. In some embodiments, the soluble factor is selected from TNF-α, interferon a (IFNa), interferon b (IFNb) and interferon (IFN)-γ. Soluble factors such as cytokines are inflammatory markers and can be assayed in patient sera or patient-derived cells or tissues to assess the efficacy of LA1 (or the efficacy of an LA1 salt or crystalline form) in treating a particular condition. A number of diagnostic assays for cytokines such IL-10 and TNF-α are known in the art and can be used to assess the anti-inflammatory efficacy of an LA1 salt or crystalline form. Such methods include, but are not limited to, ELISA (enzyme-linked immune-sorbent assay) and bead array systems for capture of cytokines by resin-bound antibodies and detection by flow cytometry.

In another aspect, the invention provides a method for treating cancer, wherein the method includes: determining the expression level of one or more proteins selected from the group consisting of CD11b, CD18, IDO1, IDO2, TDO, CSF1R, CD14, CD16, CD68, VEGFR, SIRPa, ARG1, UPAR, CD114, CD11a, CD11c, CD11d, CD45, CD4, CD8, FOXP3, CD3, ICAM1, CD31, DESMIN, alpha-smooth muscle actin, and CD64, CD32, CD89 in the subject, and administering a therapeutically effective amount of LA1, or a salt or crystalline form thereof, to the subject. In some embodiments, determining the expression level of the proteins includes obtaining a biospecimen (such as a biopsy) from the patient and determining the expression level of the proteins in the biospecimen. In some such embodiments, the method further includes administering a therapeutically effective amount of an immune checkpoint inhibitor to the subject. In some such embodiments, the method further comprises periodically determining the expression level of the protein over the course of an evaluation period, and adjusting the treatment if the expression level of the protein is observed to change over the course of the evaluation period.

In some embodiments, the method includes determining that the expression level of a protein in a biospecimen, such as a biopsy, obtained from a subject is higher than the expression level of the protein in a biospecimen sample obtained from a healthy subject. In some embodiments, the method includes determining that the expression level of a protein in a biopsy sample obtained from a subject is higher than the expression level of the protein in a non-cancerous tissue sample obtained from the subject. In some such embodiments, the expression level of one more proteins selected from the group consisting of CD11b, CD18, IDO1, IDO2, TDO, CSF1R, CD14, CD16, CD68, VEGFR, SIRPa, ARG1, UPAR, CD114, CD11a, CD11c, CD11d, CD45, CD4, CD8, FOXP3, CD3, ICAM1, CD31, DESMIN, alpha-smooth muscle actin, CD64, CD32, and CD89 is determined.

In some embodiments, the method includes determining that the expression level of a protein in a biospecimen, such as a biopsy, obtained from a subject is lower than the expression level of the protein in a biospecimen sample obtained from a healthy subject. In some embodiments, the method includes determining that the expression level of a protein in a biopsy sample obtained from a subject is lower than the expression level of the protein in a non-cancerous tissue sample obtained from the subject. In some such embodiments, the expression level of one more proteins selected from the group consisting of CD11b, CD18, IDO1, IDO2, TDO, CSF1R, CD14, CD16, CD68, VEGFR, SIRPa, ARG1, UPAR, CD114, CD11a, CD11c, CD11d, CD45, CD4, CD8, FOXP3, CD3, ICAM1, CD31, DESMIN, alpha-smooth muscle actin, CD64, CD32, and CD89 is determined.

In some embodiments, the invention provides a method for treating cancer, wherein the method includes: determining the level of one or more substances selected from the group consisting of colony stimulating factor 1 (CSF1); C-reactive protein (CRP); urokinase receptor (uPAR); soluble urokinase-type plasminogen activator receptor (suPAR); Glypican-1; CD11b; vascular endothelial growth factor (VEGF); VEGF receptor; a matrix metalloproteinase such as MMP-9 and the like; TNFα; an interleukin such as IL-6, IL-10, IL-10, IL-17, IL-23, and the like; TGFβ; interferons including IFN-α, IFN-β, and the like; tryptophan; lysine; arginine; lactate; and a microRNA in the subject, and administering a therapeutically effective amount of LA1, or a salt or crystalline form thereof, to the subject having the biomarker. In some embodiments, determining the level of the substance includes obtaining a blood, plasma, urine, or saliva sample from the patient and determining the expression level of the proteins in the sample. In some such embodiments, the method further includes administering a therapeutically effective amount of an immune checkpoint inhibitor to the subject. In some such embodiments, the method further comprises periodically determining the level of the substance over the course of an evaluation period, and adjusting the treatment if the level of the substance is observed to change over the course of the evaluation period.

In some embodiments, the method includes determining that the level of the substance in a blood, plasma, urine, or saliva sample obtained from a subject is higher than the expression level of the protein in a similar plasma sample obtained from a healthy subject. In some embodiments, the method includes determining that the level of the substance in a blood, plasma, urine, or saliva sample obtained from a subject is lower than the level of the substance in a similar sample obtained from a healthy subject. In some such embodiments, the level of one more substances selected from the group consisting of colony stimulating factor 1 (CSF1); C-reactive protein (CRP); urokinase receptor (uPAR); soluble urokinase-type plasminogen activator receptor (suPAR); Glypican-1; CD11b; vascular endothelial growth factor (VEGF); VEGF receptor; a matrix metalloproteinase such as MMP-9 and the like; TNFα; an interleukin such as IL-6, IL-1β, IL-10, IL-17, IL-23, and the like; TGFβ; interferons including IFN-α, IFN-β, and the like; tryptophan; lysine; arginine; lactate; and a microRNA is determined.

VI. Examples

Example 1. Preparation of Leukadherin LA1 DMSO Solvate Form I

A vapor diffusion of diethyl ether (outer vial, closed) was prepared into a DMSO solution (inner vial, open). After a day at room temperature, in which a fair amount of ether was added to the vial containing the DMSO, the vial was placed in a −10° C. freezer. The DMSO froze, but there were crystalline plates which had grown in the upper regions of the inner vial. The crystalline plates were characterized. $^1$H NMR (500 MHz, DMSO) δ 8.10 (d, 2H, J=8.2 Hz), 7.96 (d, 2H, J=8.4 Hz), 7.74 (s, 1H), 7.50 (d, 1H, J=3.8 Hz) 7.42 (d, 1H, J=4 Hz), 7.37-7.26 (m, 5H), 5.25 (s, 1H), 3.31 (bs, 1H).

The novel crystalline form of Leukadherin LA1 has been characterized by powder X-ray diffraction spectroscopy, which produces a fingerprint of the particular crystalline form. Measurements of 2θ typically are accurate to within +0.2 degrees.

X-ray diffraction data for crystalline Leukadherin LA1 were acquired using a Bruker SMART APEX II CCD platform diffractometer for a data collection at 100.0(5) K.1 A preliminary set of cell constants and an orientation matrix were calculated from reflections harvested from three orthogonal wedges of reciprocal space. The full data collection was carried out using MoKα radiation (graphite monochromator) with a frame time of 60 seconds and a detector distance of 3.99 cm. A randomly oriented region of reciprocal space was surveyed: four major sections of frames were collected with 0.50° steps in w at four different φ settings and a detector position of −38° in 2θ. The intensity data were corrected for absorption. Final cell constants were calculated from the xyz centroids of 4045 strong reflections from the actual data collection after integration.

FIG. 1 shows the X-ray crystal structure determined for Leukadherin LA1 DMSO Solvate Form I, data for which is summarized in Table 1 and Table 2.

TABLE 1

Crystal data for LA1 DMSO Solvate Form I.
Crystal data and structure refinement for
Leukadherin LA1 DMSO Solvate Form I

| | |
|---|---|
| Identification code | Leukadherin LA1 DMSO Solvate Form I |
| Empirical formula | C24 H21 N O5 S3 |
| Formula weight | 499.60 |
| Temperature | 100.0(5) K |
| Wavelength | 0.71073 Å |
| Crystal system | triclinic |
| Space group | P-1 |
| Unit cell dimensions | a = 8.1554(15) Å, , α = 66.860(4) |
| | b = 11.535(2) Å, , β = 86.581(4)° |
| | c = 14.091(3) Å, γ = 70.621(4)° |
| Volume | 1146.1(4) Å$^3$ |
| Z | 2 |
| Density (calculated) | 1.448 mg/m$^3$ |
| Absorption coefficient | 0.361 mm$^{-1}$ |
| F(000) | 520 |
| Crystal color, morphology | orange, plate |
| Crystal size | 0.36 × 0.30 × 0.12 mm$^3$ |
| Theta range for data collection | 2.023 to 35.010° |
| Index ranges | −13 ≤ h ≤ 13, −18 ≤ k ≤ 18, −22 ≤ l ≤ 22 |
| Reflections collected | 25036 |
| Independent reflections | 9940 [R(int) = 0.0562] |
| Observed reflections | 6038 |
| Completeness to theta = 34.970° | 98.7% |
| Max. and min. transmission | 0.7469 and 0.6405 |

TABLE 1-continued

Crystal data for LA1 DMSO Solvate Form I.
Crystal data and structure refinement for
Leukadherin LA1 DMSO Solvate Form I

| | |
|---|---|
| Refinement method | Full-matrix least-squares on $F^2$ |
| Data/restraints/parameters | 9940/0/304 |
| Goodness-of-fit on $F^2$ | 1.001 |
| Final R indices [I > 2sigma(I)] | R1 = 0.0553, wR2 = 0.1174 |
| R indices (all data) | R1 = 0.1054, wR2 = 0.1372 |
| Largest diff. peak and hole | 0.766 and −0.518 e.Å$^{-3}$ |

TABLE 2

Positional parameters for the Leukadherin LA1 at 100.0(5) K.
Atomic coordinates (×104) and equivalent isotropic displacement
parameters (Å2 × 103) for Leukadherin LA1 DMSO Solvate Form I.

| | x | y | z | Ueq* |
|---|---|---|---|---|
| S1 | 2808(1) | 3734(1) | 6146(1) | 19(1) |
| S2 | 4823(1) | 4939(1) | 6943(1) | 23(1) |
| O1 | 7504(2) | −525(2) | 1974(1) | 32(1) |
| O2 | 8673(2) | 634(2) | 2520(1) | 28(1) |
| O3 | 1403(2) | 2458(1) | 5120(1) | 17(1) |
| O4 | −1385(2) | 5201(1) | 7265(1) | 22(1) |
| N1 | 1461(2) | 5146(1) | 7210(1) | 17(1) |
| C1 | 7429(2) | 155(2) | 2464(2) | 22(1) |
| C2 | 5898(2) | 544(2) | 3041(1) | 19(1) |
| C3 | 4530(2) | 71(2) | 3059(1) | 21(1) |
| C4 | 3046(2) | 465(2) | 3547(1) | 21(1) |
| C5 | 2937(2) | 1324(2) | 4047(1) | 17(1) |
| C6 | 4315(2) | 1794(2) | 4028(1) | 19(1) |
| C7 | 5772(2) | 1413(2) | 3530(1) | 20(1) |
| C8 | 1369(2) | 1744(2) | 4542(1) | 17(1) |
| C9 | −235(2) | 1618(2) | 4542(1) | 19(1) |
| C10 | −1252(2) | 2280(2) | 5141(1) | 20(1) |
| C11 | −218(2) | 2786(2) | 5478(1) | 18(1) |
| C12 | −535(2) | 3562(2) | 6086(1) | 18(1) |
| C13 | 607(2) | 4002(2) | 6381(1) | 17(1) |
| C14 | 57(2) | 4831(2) | 6989(1) | 17(1) |
| C15 | 3005(2) | 4676(2) | 6823(1) | 18(1) |
| C16 | 1272(2) | 5907(2) | 7860(1) | 18(1) |
| C17 | 1905(2) | 5017(2) | 8974(1) | 18(1) |
| C18 | 2607(3) | 5494(2) | 9560(2) | 25(1) |
| C19 | 3138(3) | 4721(2) | 10599(2) | 28(1) |
| C20 | 2976(3) | 3464(2) | 11065(2) | 26(1) |
| C21 | 2281(3) | 2984(2) | 10489(2) | 27(1) |
| C22 | 1744(2) | 3757(2) | 9451(1) | 23(1) |
| S3 | 7700(1) | 1389(1) | 8335(1) | 26(1) |
| O5 | 8762(2) | −62(1) | 8587(1) | 30(1) |
| C23 | 5936(3) | 1352(2) | 9147(2) | 36(1) |
| C24 | 8883(3) | 1978(2) | 8955(2) | 34(1) |

*Ueq is defined as one third of the trace of the orthogonalized Uij tensor

Crystal Data and Structure Refinement for Leukadherin LA1:

The following parameters were used. Temperature—100.0(5) K, wavelength—0.71073 Å, crystal system—triclinic, space group—P-1, unit cell dimensions—(a=8.1554(15) Å, α=66.860(4)°, b=11.535(2) Å, β=86.581(4)°, c=14.091(3) Å, γ=70.621(4)°, volume—1146.1(4) Å$^3$, Z—2, density (calculated)—1.448 Mg/m$^3$, absorption coefficient—0.361 mm$^{-1}$, F(000)—520, crystal color & morphology—orange & plate, crystal size—0.36×0.30×0.12 mm$^3$, theta range for data collection—2.023 to 35.010°, index ranges—(−13≤h≤13, −18≤k≤18, −22≤l≤22), reflections collected—25036, independent reflection—9940 [R(int)=0.0562], observed reflections—6038, completeness to theta=34.970°-98.7%, absorption correction—multi-scan, max. and min. transmission—0.7469 and 0.6405, refinement method—Full-matrix least-squares on F2, goodness-of-fit on F2-1.001, final R indices [I>2sigma(I)]−(R1=0.0553, wR2=0.1174), R indices (all data)−(R1=0.1054, wR2=0.1372), largest diff. peak and hole −0.766 and −0.518 e·Å$^{-3}$ The asymmetric unit of Leukadherin LA1 Form I contains one target molecule and one co-crystallized dimethyl sulfoxide solvent molecule, both in general positions. The phenyl rings of the molecules are stacked pairwise at planar distances of approximately 3.5 and 3.6 Å for rings C2-C7 and C17-C22, respectively (see FIG. 1). Hydrogen bonding links the solvent molecule to the target molecule (see FIG. 1 and Table 1).

Example 2. Characterization of LA1 Free Acid

The free acid form of LA1 has an aqueous solubility of 0.78 μg/mL and a calculated pKa of 4.1. A limited salt screen was previously conducted using five inorganic counter-ions (Na, K, NH4, Ca and Mg). Although the salts exhibited crystallinity, most were hygroscopic.

Solubility Estimation.

Aliquots of the test solvent were added to an accurately weighed sample (~10 mg) of LA1 at ambient temperature. The aliquot volumes were typically 200-1000 μL. Complete dissolution of the test material was determined by visual inspection. The solubility was estimated from these experiments based on the total solvent used to provide complete dissolution. It should be noted that the actual solubility may be greater than that calculated because of the use of solvent aliquots that were too large or due to a slow rate of dissolution.

A number of samples that did not show dissolution by aliquot addition were subjected to a temperature cycling regime. First, the samples were heated from 20° C. to within 3° C. of solvent boiling point (or 100° C., whichever was lower) at 0.5° C./minute; then cooled to 20° C. at 0.2° C./minute while stirring at 800 rpm.

From the infrared (IR) transmission data of the sample vials, dissolution and precipitation events were recorded as the point of complete transmission of IR and the onset of turbidity by IR respectively. Selected samples were also agitated on an orbital shaker at 50° C. and visually observed for dissolution.

Solubility Determination by Equilibration.

An aliquot of the UHQ water test solvent (1 mL) was added to an accurately weighed sample of the LA1 salts and agitated at ambient temperature for a period of 4 days. A sample was withdrawn, filtered through a 0.2 PTFE filter, and analyzed by HPLC.

X-Ray Powder Diffraction (XRPD).

XRPD analyses were performed using a Panalytical Xpert Pro diffractometer equipped with a Cu X-ray tube and a Pixcel detector system. The isothermal samples were analyzed in transmission mode and held between low density polyethylene films. Frames were collected with 0.013° steps in ω, a detector position range of 3–40° in 2θ with a counting time of 99 sec., and a ~22 min run time. XRPD patterns were sorted and manipulated using HighScore Plus 2.2c software.

Thermogravimetric Differential Thermal Analysis (TG/DTA).

Thermogravimetric analyses were carried out on a Mettler Toledo TGA/DSC1 STARe. The calibration standards were indium and tin. Samples were placed in an aluminum sample pan, inserted into the TG furnace and accurately weighed. The heat flow signal was stabilized for one minute at 30° C., prior to heating to 300° C. in a stream of nitrogen at a rate of 10° C./minute.

Proton Nuclear Magnetic Resonance spectroscopy (NMR).

Proton NMR analysis was carried out on a Bruker 500 MHz or 400 MHz instrument in $d_6$-DMSO or MeOD. A drop of $D_2O$ and/or TFA was added to several samples to shift the water peak from overlapping with the peak due to base.

Hplc Analysis.

HPLC was used to determine aqueous equilibrium solubility at ambient temperature. HPLC was conducted using a Supelco Ascentis Express C18, 4.6×150 mm, 2.7 µm column; a mobile phase A containing 0.1% phosphoric acid in water; a mobile phase B containing acetonitrile; a solvent gradient ranging from 10% B to 95% B over 9 minutes; a solvent flow rate of 1.5 mL/min; a sample volume of 10 µt; and UV detection at 264 nm. The retention time of LA1 was typically 8.4±0.2 min. A standard for HPLC analysis was initially prepared using LA1 free acid but was insoluble in DMSO:acetonitrile:water (1:1:1) and therefore another standard was prepared using LA1 choline salt, which was soluble in acetonitrile:water (1:1).

Characterization of LA1.

Figure 3:
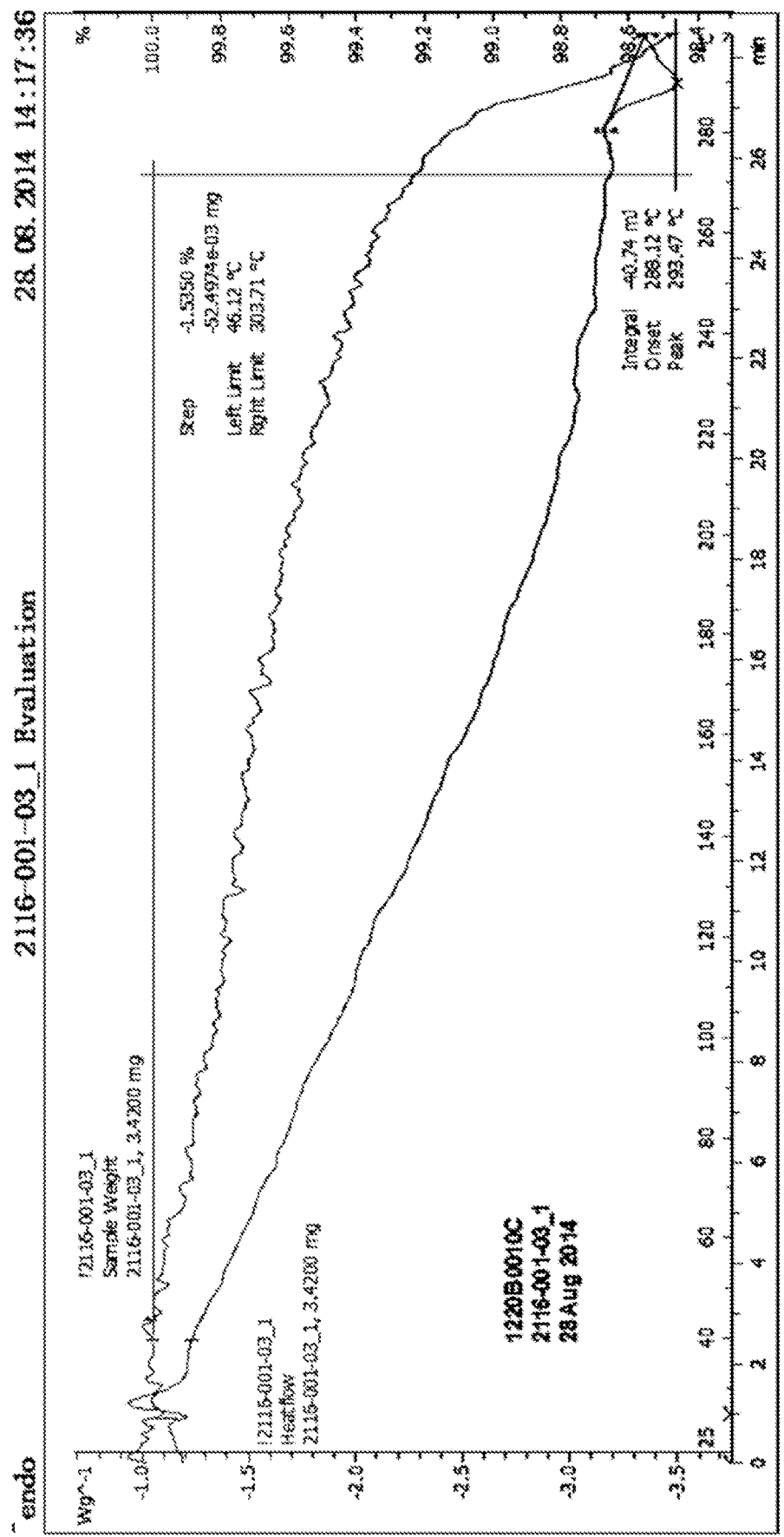
FIG. 3 shows thermogravimetric-thermal differential analysis (TG-DTA) data for LA1 free acid.

As-received LA1 was a crystalline solid by XRPD analysis but contained some disorder as indicated by peak broadening of some of the diffraction peaks. (FIG. 2). Thermogravimetric/Differential Thermal Analysis (TG/DTA) was performed to determine the thermal profile and associated % weight changes of LA1. A weight loss of <1% was observed below 280° C. suggesting that the material is anhydrous FIG. 3. A small weight loss of 0.5% was noted from 280-300° C., corresponding to a small endotherm in the accompanying DTA trace but was not investigated further.

Figure 4:
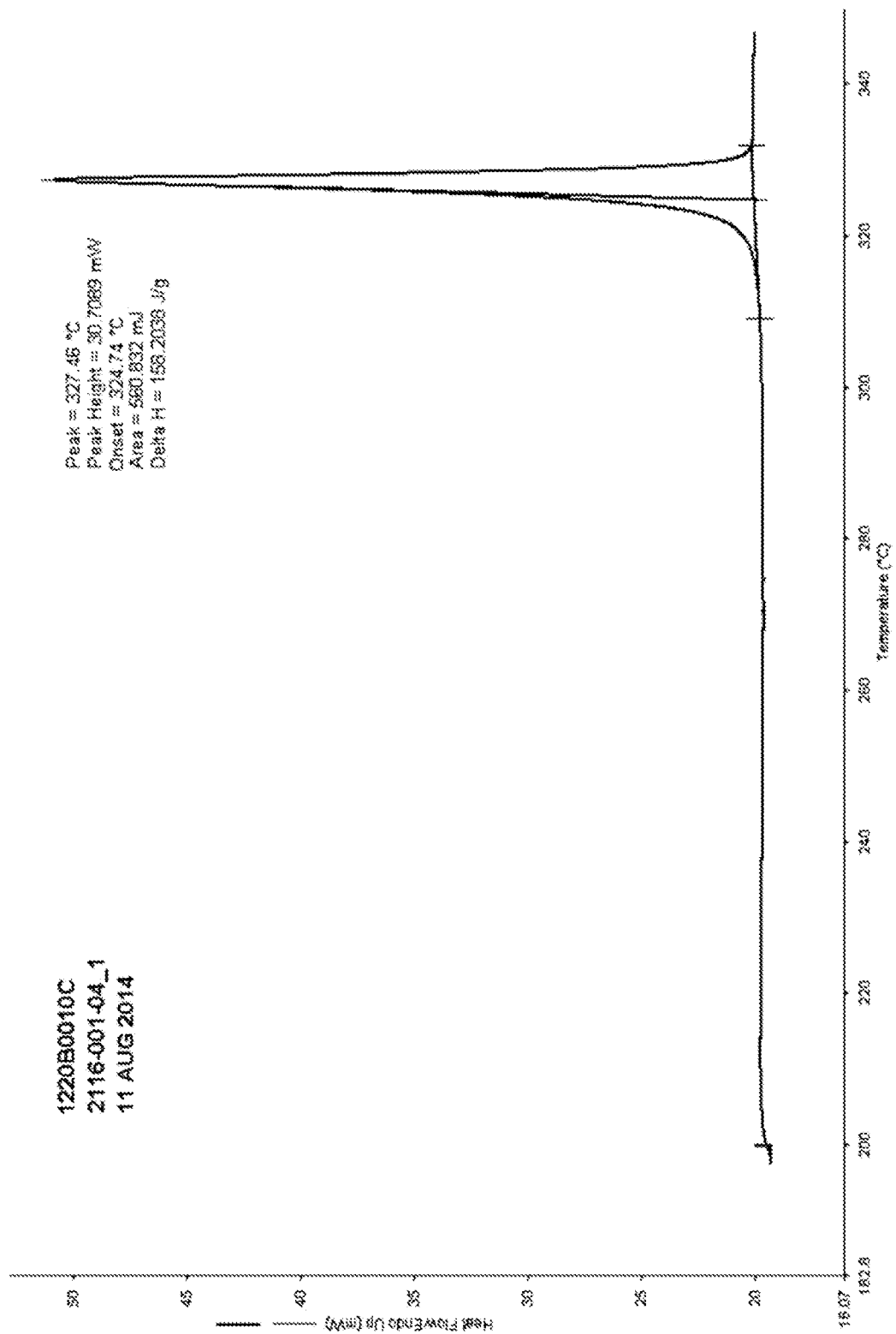
FIG. 4 shows a differential scanning calorimetry (DSC) thermogram recorded for LA1 free acid.

The DSC thermogram of the sample indicated a melting onset of ~318° C. FIG. 4. Small deviations to the baseline were noted between 260-280° C. but were not investigated further. The proton NMR spectrum of the API was recorded in $d_6$-DMSO and conformed to the molecular structure. Soon after dissolution of the API in $d_6$-DMSO, noticeable precipitation was observed in the NMR tube, probably due to formation of the known DMSO solvate.

Estimated solubility of LA1.

Approximate solubility of as-received LA1 were estimated in eight solvents by the aliquot addition method in order to select suitable solvents for the salt studies (Table 3) and it was insoluble in all solvents tested. Several solvent mixtures were tested but the API was insoluble in all mixtures investigated. Even upon heating, the API only dissolved in DIVIF at 10 mg/mL at 73° C.

TABLE 3

Approximate solubilities of LA1 at 20° C.

| Solvent | Acronym | Approx. solubility (mg/mL) | Sample no. (2116-) |
|---|---|---|---|
| acetone | — | <10 | 001-09 |
| acetonitrile | ACN | <10 | 001-08 |
| anisole | — | <10 | 001-13 |
| dichloromethane | DCM | <10 | 001-10 |
| dimethylformamide | DMF | <10 | 001-12 |
| DMF:MeOH (1:1) | — | <10 | 001-19 |
| DMF:THF (1:1) | — | <7 | 001-18 |
| hexafluoroisopropanol | HFIPA | <10 | 001-11 |
| MeOH:ACN:dioxane (1:1:1) | MAD | <10 | 001-15 |
| MeOH:acetone (1:1) | — | <10 | 001-16 |
| methanol | MeOH | <10 | 001-06 |
| THF | THF | <10 | 001-07 |

TABLE 3-continued

Approximate solubilities of LA1 at 20° C.

| Solvent | Acronym | Approx. solubility (mg/mL) | Sample no. (2116-) |
|---|---|---|---|
| THF:Acetone (1:1) | — | <10 | 001-14 |
| THF:MeOH (1:1) | — | <10 | 001-17 |
| DMF:water (1:1) | — | <10 | 001-20 |

Those experiments which did not show dissolution in ~10 volumes were temperature cycled or slurried at elevated temperature as described above.

Conclusions from Characterization and Solvent Study.

XRPD analysis indicated that LA1 was a disordered crystalline material. TG/DTA data showed negligible weight loss from 30-280° C., suggesting minimal moisture or residual solvent content, and indicating that LA1 remains thermally stable up to 280° C. A small weight loss of 0.5% with accompanying endotherm was noted from 280-300° C. but was not investigated further. The DSC thermogram of the sample indicated a melting onset of ~318° C. Small deviations to the baseline were noted between 260-280° C. but were not investigated further. The molecular structure was confirmed by $^1H$ NMR spectroscopy using $d_6$-DMSO. Precipitation was noted in the NMR tube after initial dissolution of the API and was probably due to formation of the known DMSO solvate. The solubility of LA1 was assessed by aliquot addition and exhibited poor solubility in all solvents tested. Dissolution was achieved only in DMF with heating (73° C.) at ~10 mg/mL.

Example 3. Preparation and Characterization of LA1 Salts

LA1 salts with improved aqueous solubility and low hygroscopicity were prepared and characterized.

All solids from the crystallization experiments were analyzed by XRPD and the resulting patterns compared to that exhibited by the starting material. Novel XRPD patterns were assigned an alphabetical descriptor in order of discovery (Pattern B, Pattern C etc.). Where sufficient material was available, further analysis (e.g. NMR or TGA) was conducted on solids with novel XRPD patterns to allow tentative assignment of the novel pattern as a polymorph, solvate, hydrate, degradant or mixture thereof. Bases used are summarized in Table 4.

TABLE 4

Materials and reagents used for salt studies

| Bases Used | Abbreviation |
|---|---|
| 2-(dimethylamino)ethanol | deanol |
| 4-(2-hydroxyethyl) morpholine | — |
| ammonium hydrogen carbonate | $NH_4HCO_3$ |
| ammonium hydroxide | $NH_4OH$ |
| calcium hydroxide | $Ca(OH)_2$ |
| choline hydroxide | — |
| L-lysine monohydrate | — |
| magnesium hydroxide | $Mg(OH)_2$ |
| N-methyl-D-glucamine | meglumine |
| piperazine | — |
| potassium carbonate | $K_2CO_3$ |
| potassium hydrogen carbonate | $KHCO_3$ |

TABLE 4-continued

Materials and reagents used for salt studies

| Bases Used | Abbreviation |
|---|---|
| potassium hydroxide | KOH |
| sodium carbonate | Na$_2$CO$_3$ |
| sodium hydrogen carbonate | NaHCO$_3$ |
| sodium hydroxide | NaOH |
| tromethamine | TRIS |
| — | — |

Solvent Based Techniques.

Solvent based experiments were initially performed at approximately 90 mg scale; however, this was revised to approximately 20-30 mg scale in glass vials due to limited API.

Experiments were carried out at a scale of 20-30 mg with equimolar stoichiometry and using excess base. Weighed amounts of acid and base were combined in glass vials, followed by solvent and slurried at ambient temperature or 40° C. Alternatively, weighed amounts of acid were combined with excess base in glass vials and solvents added. Samples were slurried at ambient temperature or at 40° C./50° C. for 1-2 days. Solids were isolated by vacuum filtration, centrifugation or dried by slow evaporation, purged under N$_2$ stream or under vacuum desiccation.

Slow Evaporation.

Some of the experiments setup as slurries were allowed to evaporate to dryness under ambient conditions, under N$_2$ stream or under vacuum desiccator and solids isolated and analyzed by XRPD. One sample from tromethamine produced a solution when API was combined with excess base and this was evaporated under a N$_2$ stream.

Slurry Experiments.

LA1 and base (in equimolar stoichiometry or in excess) were placed in a vial and solvent added. The mixture was agitated at the selected temperature by magnetic stirring for 1 or 2 days. Solids were isolated by vacuum filtration/centrifugation and air dried prior to analysis by XRPD.

Sonication.

Selected solids generated from slurry experiments were sonicated at 70% intensity for approximately 8 minutes using a Cole-Parmer 130W ultrasonic processor using a pulsed program. All solids recovered from these experiments were analyzed using XRPD.

Evaporation, prolonged slurry (at ambient and elevated temperatures) and sonication techniques were employed using an equimolar stoichiometry of API to base. Excess base was also used for a number of experiments as initial results from equimolar mixtures of several bases indicated incomplete salt formation.

Evaporation in Vials.

The only samples that dissolved completely were those with choline in DMF or MeOH-THF, forming a dark red solution. Evaporation of these solutions generated oils, which were then dried under vacuum. Solids were retrieved from one of the samples after drying but the other sample remained as a sticky oil and was not analyzed (Table 5). The solid was composed of crystalline material (FIGS. 5A-B) and salt formation was confirmed for the solids by 1H NMR spectroscopy.

TABLE 5

Results from evaporations in vials

| Base | Conditions | Slow evaporation Result | XRPD |
|---|---|---|---|
| choline | 1:1 base:API slurry @ 50° C. THF-MeOH (3:1). Slow evap under N$_2$ | Dark red solid | Pattern G |
| choline | XS API + DMF, soln evap, dry under vac | Sticky oil | — |

Slurry Experiments.

Suspensions of LA1 and base were agitated in various solvents at ambient temperature or 40/50° C. for 1-2 days and analyzed by XRPD (Table 6). A number of the slurries were evaporated to dryness by leaving uncapped or under N$_2$. Two new forms of the API were isolated from a number of experiments (Pattern C and D materials) and are further discussed in section 7. Crystalline solids were isolated from several of the counter-ions including choline, meglumine, tromethamine and Choline salts (FIGS. 6A-E) and disordered solids from Ca, K, Mg, Na and piperazine (FIGS. 9A-H), although many were mixtures containing API. A new form of choline salt was crystallized and two forms of Ca and tromethamine salts were isolated. Salt formation was confirmed for the unique solids by $^1$H NMR spectroscopy.

TABLE 6

Results from slurry experiments

| Base | Sample (2116-) | Conditions | XRPD |
|---|---|---|---|
| Ca(OH)$_2$ | 011-24 | 1:2 base:API, slurry @ 40° C. in water-NMP (5:1) | Pattern N (disordered) |
| choline OH | 011-26 | 1:1 base:API slurried in THF at RT | Pattern O |
| meglumine | 011-07_1 | 1:1 base:API slurry @ 50° C. in THF-MeOH (2:1). Slow evap under N$_2$ | Pattern H |
| piperazine | 011-28 | 1:1 base:API slurry @ 40° C. 1 day | Pattern P) |
| tromethamine | 011-23_2 | 2:1 base:API slurry @ 40° C. in NMP. Partial evap under N$_2$. Washed 4x THF. | Pattern M |

Conclusions from Salt Studies.

LAI salts were prepared using twelve pharmaceutically acceptable bases and involved different crystallization techniques and conditions.

Five salts were isolated which exhibited crystallinity: choline, meglumine, calcium, piperazine, and tromethamine. Salt formation for each was confirmed by $^1$H NMR analysis and the tromethamine salts appeared to be NMP solvates. Multiple forms of salts were isolated for choline, tromethamine, and calcium salts. Solids were also isolated from Ca, Mg, and Na counter-ions that exhibited crystallinity but by XRPD appeared to be a mixture of API and suspected salt. Complete conversion to salts could not be achieved, except for one Ca salt sample, which was disordered by XRPD. Solids isolated from other counter-ions were composed of mixtures of starting materials.

Example 4. Hygroscopicity and Aqueous Solubility of Crystalline Salts

Humidity stress at 40° C./75% RFI.

Salt samples that exhibited crystallinity were stressed under 40°/75% RH conditions for 5-6 days to assess deliquescence and hygroscopicity. Approximately 5 mg of LA1 salts that exhibited crystallinity were added to glass vials, which were placed uncapped inside larger vials containing saturated aqueous solution of NaCl. The larger vials were capped, sealed with Parafilm and placed inside an oven at 40° C. for up to 6 days. Salts were then removed from these conditions and changes observed (e.g. color, deliquescence etc.) before being analyzed for weight change and by XRPD. Samples were examined visually after stressing, form composition confirmed by XRPD analysis and weight change recorded (Table 7).

TABLE 7

Results from humidity stressing experiments

| Salt | Sample (2116-) | Result | Weight gain (%) | XRPD after stressing |
|---|---|---|---|---|
| Ca | 021-04 | Solid, not deliquescent | 1.7 | More disordered |
| choline | 021-01 | Solid, not deliquescent | 8.9 | New pattern (Q) |
| meglumine | 021-02 | Solid, not deliquescent | 1.4 | No change |
| piperazine | 021-05 | Solid, not deliquescent | −5.5 | New pattern (R) |
| tromethamine | 021-03 | Solid, not deliquescent | n/a | New pattern (S) |

None of the samples deliquesced under the humidity conditions tested but three of the samples gained weight, particularly for the choline salt. In addition, XRPD analysis indicated that the choline, tromethamine and piperazine salts had undergone phase change after stressing, possibly to hydrated forms. The large weight gain noted for the choline salt would support hydrate formation but a weight loss was observed for the piperazine salt, the cause of which is unknown.

Aqueous Solubilities of Selected Salts.

Aqueous solubilities of salts that exhibited crystallinity and were not deliquescent were determined by HPLC analysis at ambient temperature. Samples were slurried in water for 4-5 days before analysis. Solubility is summarized in Table 8.

TABLE 8

Results from aqueous solubility estimation

| Salt | Sample (2116-) | Input Salt (2116-) | Aq solub (mg/mL)[1] | HPLC purity (%) | Soln pH | Appearance |
|---|---|---|---|---|---|---|
| calcium | 029-04 | 011-24 | 0.002 | 5.58 | 7 | No change |
| choline | 029-01 | 011-06 | 7.052 | 75.51 | 8 | Darker red color |
| meglumine | 029-02 | 011-07_1 | 0.724 | 34.7 | 8 | No change |
| piperazine | 029-06 | 011-28 | 0.013 | 5.31 | 8 | No change |
| tromethamine | 029-03 | 011-23 | 0.387 | 89.7 | 8 | Yellow ppt seen |

Note:
The concentration values were corrected for weight of counter-ion, purity of standard (91.6%) and volatile content of standard (4.8%).

The choline salt was the most soluble at 7.1 mg/mL, followed by meglumine and tromethamine. The calcium and piperazine salts were not very soluble.

The tromethamine salt changed color during slurrying to a yellow solid. XRPD analysis indicated that it had converted to the free API during slurrying and so was not physically stable in water over that period of time. Solubility and chemical purity estimation by HPLC was approximate as the HPLC method was not validated. The results suggest that all salts are not chemically stable when slurried in aqueous media for 4-5 days. However, the data were obtained after 4-5 days of slurrying in order to achieve equilibrium solubility; it is possible that the salts may be stable for shorter periods of time in water.

Example 5. Scale-Up of Choline and Meglumine of Salt Production

Small Scale Production.

Both salts were prepared on a small scale by slurrying components in ethanol (Table 9). The choline salt was also slurried in acetone and EtOAc as yield from EtOH was low, due to improved solubility of the salt in EtOH.

The XRPD pattern of the choline salt from EtOH matched that of the salt generated from dioxane-THF but the samples from acetone and EtOAc exhibited a different powder pattern, which matched that of the sample from the 40°/75% RH stress, see section 6.1 (FIGS. 10A-E). The sample from acetone was analyzed by $^1$H NMR spectroscopy and salt formation was confirmed. A drop of TFA was added to shift the water peak from overlapping with the peak due to choline. Acetone was not detected in the spectrum.

Solids from the meglumine salt preparation exhibited a unique powder pattern (FIGS. 10A-E). Salt formation was confirmed by $^1$H NMR spectroscopy and ethanol was present at 1 mole eq. suggesting solvate formation.

Both salts were initially prepared on a larger scale from ethanol. XRPD analysis of solids from the choline salt slurry indicated that the salt had formed but contained a small amount of API (FIGS. 14A-E). Some unique diffraction peaks were also seen indicating the presence of a minor amount of an additional component. Salt formation was confirmed by 1H NMR spectroscopy. Yield for the choline salt was poor due to increased solubility in ethanol and therefore the preparation was repeated. The repeated sample was dried under vacuum to remove residual ethanol but XRPD analysis indicated that it was disordered and was different to the original form (FIGS. 14A-E). The sample also contained a significant amount of API. Salt formation was confirmed by $^1$H NMR spectroscopy.

The preparation was repeated again using acetone with better yield and the crystalline solids were composed of Pattern Q material (FIGS. 14A-E). Salt formation was confirmed by 1H NMR spectroscopy.

The meglumine salt was prepared on a larger scale with reasonable yield and the XRPD pattern was consistent with that of the salt generated on a smaller scale from ethanol (FIGS. 14A-E). A minor amount of API was also present by XRPD analysis. The sample was dried to remove residual solvent and XRPD analysis indicated that the solid was disordered but contained the same form (FIGS. 14A-E). Salt

TABLE 9

Results from crystallization of choline and meglumine salts

| Base/ID | Solvent | Method | XRPD | Comment |
|---|---|---|---|---|
| choline/ 2116-031-01 | EtOH, MTBE (2:1) | 1:1 base:API slurried @ 40° C. ~2 hours. Aliquot removed, vac filter, MtBE wash | Pattern G, matches 011-06 | Orange solid |
| choline/ 2116-031-03 | acetone | 1:1 base:API slurried @ RT o/n. Aliquot removed, vac filter | Pattern Q, matches salt stressed at 40 C./75% RH (021-01) | Red solid |
| choline/ 2116-031-04 | EtOAc | 1:1 base:API slurried @ RT o/n. Aliquot removed, vac filter | Pattern Q | Orange solid |
| meglumine/ 2116-031-02 | EtOH | 1:1 base:API slurried @ 40° C. ~2 hours. Aliquot removed, vac filter, MtBE wash | new Pattern (T) | Orange-yellow solid | o/n = overnight,
RT = ambient temperature,
vac = vacuum

Preparation of LA1 Meglumine Salt on a Larger Scale (2116-033-02).

LA1 (203.3 mg) and N-methyl-D-glucamine (94.16 mg) were weighed into a glass vial, followed by addition of EtOH (0.6 mL) and the mixture stirred at ambient temperature overnight. Solids were isolated by vacuum filtration and washed with t-BME, then with EtOH. The solids were then placed in a vacuum oven and dried at 40-47° C. overnight. A red/orange powder was collected, yield=71%.

Preparation of LA1 Choline Salt on a Larger Scale (2116-033-04).

LA1 (201.3 mg) and ~46% choline hydroxide solution in water (117.3 μL) were combined in a glass vial, followed by addition of acetone (0.7 mL) and the mixture stirred at ambient temperature overnight. Solids were isolated by vacuum filtration and air dried. A dark red powder was collected, yield=73%.

formation was confirmed by $^1$H NMR spectroscopy with an equimolar stoichiometry and contained 0.5 mol eq. of ethanol.

Example 6. Preparation of Leukadherin LA1 Meglumine Salt Form H

Leukadherin LA1 (203.3 mg) and N-methyl-D-glucamine (94.16 mg) were weighed into a glass vial. Ethanol (0.6 mL) was added and the mixture was stirred at ambient temperature overnight. Solids were isolated by vacuum filtration and washed with t-butyl methyl ether, then with ethanol. The solids were then placed in a vacuum oven and dried at 40-47° C. overnight. A red/orange powder was collected, yield=71%. Alternatively, Leukadherin LA1 (~200 mg) and N-methyl-D-glucamine in a 1:1 ratio were weighed into a glass vial. Tetrahydrofuran:Methanol (2:1, 0.6 mL) was added and the mixture stirred at 50° C. with a slow evaporation under nitrogen atmosphere. A red/orange solid was collected. 1H NMR (500 MHz, DMSO) δ 8.04 (d, 2H, J=8.6 Hz), 7.87 (d, 2H, J=8.6 Hz), 7.74 (s, 1H), 7.41 (ABq, 2H, $J_{AB}$=3.9 Hz), 7.27-7.37 (m, 5H), 5.26 (s, 2H), 3.84 (dt, 1H, J=4.4, 3.9 Hz), 3.68 (dd, 1H, J=4.9, 1.5 Hz), 3.60 (dd, 1H, J=10.9, Hz), 3.50 (m, 1H) 3.44 (dd, 1H, J=8.1, 1.7 Hz), 3.41 (dd, 1H, J=10.8, 5.8 Hz), 3.31 (bs, 7H), 2.91 (dd, 1H, J=12.5, 3.8 Hz), 2.84 (dd, 1H, J=11.3, 7.8 Hz), 2.47 (s, 3H).

Form H produces a unique powder X-ray diffraction pattern (FIG. 6B; Table 10).

TABLE 10

Powder X-ray diffraction peak positions and intensities for Leukadherin LA1 Meglumine Salt Form H.

| Peak Position 2θ (Copper) | Intensity |
|---|---|
| 5.334 | 1574 |
| 7.128 | 3086 |
| 9.221 | 985 |
| 9.611 | 871 |
| 10.716 | 2414 |
| 10.716 | 2414 |
| 10.911 | 2184 |
| 11.847 | 1077 |
| 12.315 | 995 |
| 14.109 | 922 |
| 14.876 | 804 |
| 16.085 | 1271 |
| 16.488 | 1653 |
| 17.047 | 963 |
| 17.658 | 1285 |
| 18.477 | 1127 |
| 18.828 | 837 |
| 19.166 | 819 |
| 19.322 | 994 |
| 19.725 | 1062 |
| 19.855 | 784 |
| 20.31 | 1438 |
| 20.817 | 852 |
| 20.856 | 866 |
| 21.545 | 726 |
| 22.078 | 617 |
| 22.377 | 640 |
| 23.092 | 1135 |
| 23.326 | 732 |
| 23.56 | 1443 |
| 23.82 | 787 |
| 23.859 | 716 |
| 24.86 | 1360 |
| 25.302 | 795 |
| 27.2 | 1554 |
| 28.019 | 504 |
| 29.761 | 511 |
| 30.021 | 420 |
| 30.268 | 419 |
| 30.359 | 433 |
| 31.074 | 685 |
| 32.14 | 363 |
| 33.141 | 291 |
| 33.453 | 283 |
| 33.713 | 436 |
| 33.804 | 389 |
| 34.181 | 298 |
| 34.701 | 408 |
| 35.715 | 318 |
| 36.118 | 285 |
| 36.287 | 337 |
| 36.508 | 301 |
| 38.419 | 372 |
| 38.536 | 343 |

Example 7. Preparation of Leukadherin LA1 Meglumine Salt Form T

Leukadherin LA1 (~200 mg) and N-methyl-D-glucamine in a 1:1 ratio were weighed into a glass vial. Ethanol (0.6 mL) was added and the mixture stirred at 50° C. for 2 hours. Solids were isolated by vacuum filtration and washed with t-butyl methyl ether. A red/orange solid was collected. 1H NMR (500 MHz, DMSO) δ 8.04 (d, 2H, J=8.6 Hz), 7.87 (d, 2H, J=8.6 Hz), 7.74 (s, 1H), 7.41 (ABq, 2H, JAB=3.9 Hz), 7.27-7.37 (m, 5H), 5.26 (s, 2H), 3.84 (dt, 1H, J=4.4, 3.9 Hz), 3.68 (dd, 1H, J=4.9, 1.5 Hz), 3.60 (dd, 1H, J=10.9, Hz), 3.50 (m, 1H) 3.44 (dd, 1H, J=8.1, 1.7 Hz), 3.41 (dd, 1H, J=10.8, 5.8 Hz), 3.31 (bs, 7H), 2.91 (dd, 1H, J=12.5, 3.8 Hz), 2.84 (dd, 1H, J=11.3, 7.8 Hz), 2.47 (s, 3H).

Form T produces a unique powder X-ray diffraction pattern (Table 11).

TABLE 11

Powder X-ray diffraction peak positions and intensities for Leukadherin LA1 Meglumine Salt Form T

| Position 2θ (Copper) | Intensity |
|---|---|
| 6.907 | 1088 |
| 8.233 | 882 |
| 8.376 | 1295 |
| 9.416 | 723 |
| 11.587 | 672 |
| 14.98 | 518 |
| 15.058 | 526 |
| 15.5 | 593 |
| 17.229 | 958 |
| 17.84 | 557 |
| 18.061 | 579 |
| 20.531 | 506 |
| 21.285 | 838 |
| 21.909 | 751 |
| 22.312 | 684 |
| 23.508 | 546 |
| 24.964 | 587 |
| 26.719 | 579 |

Example 8. Purification of LAI Meglumine (NMDG) Salt Polymorphs

NMDG salts were purified through recrystallization by heating at various temperatures or at room temperature in various solvents as shown in Table 12-Table 13. Table 12 shows polymorph screening of meglumine salt in protic solvents, and Table 13 shows polymorph screening of meglumine salt in protic solvents. The protic solvents included methanol, ethanol, isopropyl alcohol, n-butanol and water. The aprotic solvents included acetone, ethyl acetate, dimethyformamide (DMF), dimethyl sulfoxide (DMSO), isopropyl alcohol (IPA), tetrahydrofuran (THF), acetonitrile (ACN) and N-methyl pyrrolidone (NMP). The precipitation occurred at room temperature. No clear solution was observed on heating. FIGS. 15A-J show XRPD patterns obtained for LA1 meglumine salts in various solvents.

The crystalline form L was obtained in isopropylacetate, at 70° C., and is characterized by an X-ray powder diffraction (XRPD) pattern in accordance with FIG. 11, as determined on a diffractometer using Cu-Kα radiation. The crystalline form M was obtained in acetone, at 70° C., and is characterized by an X-ray powder diffraction (XRPD) pattern in accordance with FIG. 12, as determined on a diffractometer using Cu-Kα radiation. The crystalline form N was obtained in DMF, at 70° C., and is characterized by an X-ray powder diffraction (XRPD) pattern in accordance with FIG. 13 (and FIG. 15I), as determined on a diffractometer using Cu-Kα radiation.

TABLE 12

Polymorph screening of meglumine salt in protic solvents

| Solvent | Condition | Observation | Remarks | XPRD |
|---|---|---|---|---|
| Methanol | 1:30 Salt:Solvent at 70° C. | No clear solution observed. Fluffy nature observed during heating | Complete disintegration of salt is observed based on NMR pattern | NA |
| Ethanol | 1:30 Salt:Solvent at 70° C. | No clear solution observed. Fluffy nature observed during heating | Complete disintegration of salt is observed based on NMR pattern | NA |
| IPA | 1:30 Salt:Solvent at 70° C. | No clear solution observed. Fluffy nature observed during heating | Complete disintegration of salt is observed based on NMR pattern | NA |
| n-Butanol | 1:30 Salt:Solvent at 100° C. | No clear solution observed. Fluffy nature observed during heating | Complete disintegration of salt is observed based on NMR pattern | NA |
| Methanol | 1:30 Salt:Solvent at 25-30° C. | No clear solution observed. Fluffy nature observed during heating | Complete disintegration of salt is observed based on NMR pattern | NA |
| Ethanol | 1:30 Salt:Solvent at 25-30° C. | No clear solution observed. Fluffy nature observed during heating | Partial disintegration of salt is observed based on NMR pattern | NA |
| H₂O | 1:30 Salt:Solvent at 25-30° C. | No clear solution observed. Fluffy nature observed during heating | Complete disintegration of salt is observed based on NMR pattern | NA |

TABLE 13

Polymorph screening of meglumine salt in aprotic solvents

| Solvent | Condition | Observation | Remarks | XPRD | HPLC Purity (A %) |
|---|---|---|---|---|---|
| DMF | 1:10 Salt:Solvent at 70° C. | Clear solution observed. Precipitate appeared upon cooling at room temperature. MTBE was used for transfer & filtration | NMR complies with authentic, DSC shows broad melting point of 139.9° C., Crystal Form N | See, FIG. 15I, FIG. 13 | 98.72 |
| DMF | 1:10 Salt:Solvent at 25-30° C. | Clear solution observed. Precipitate appeared upon cooling at room temperature. MTBE was used for transfer & filtration. | NMR complies with authentic, DSC shows broad melting point of 139.3° C. | See, FIG. 15B | 98.65 |
| DMSO | 1:10 Salt:Solvent at 70° C. | Clear solution observed. Methanol added at RT for precipitation | Disintegration of salt is observed based on NMR pattern | NA | |
| DMSO | 1:5 Salt:Solvent at 70° C. | Clear solution observed. Methanol added at RT for precipitation | Disintegration of salt is observed based on NMR pattern. | NA | |
| DMSO | 1:5 Salt:Solvent at 70° C. | Clear solution observed. On cooling THF added as anti solvent | Precipitation didn't occur | NA | |
| DMSO | 1:5 Salt:Solvent at 70° C. | Clear solution observed. On cooling ACN added as anti solvent and ppt observed | NMR complies with authentic | See, FIG. 15J | |
| DMSO | 1:5 Salt:Solvent at 70° C. | Clear solution observed. On cooling Acetone added as anti solvent | Precipitation didn't occur | NA | |
| THF | 1:30 Salt:Solvent at 70° C. | Clear solution observed. Precipitation | NMR complies with authentic | See, FIG. 15H (Amorphous) | 97.80 |

TABLE 13-continued

Polymorph screening of meglumine salt in aprotic solvents

| Solvent | Condition | Observation | Remarks | XPRD | HPLC Purity (A %) |
|---|---|---|---|---|---|
| ACN | 1:30 Salt: Solvent at 70° C. | appeared during cooling No clear solution observed. Fluffy nature observed during heating | NMR complies with authentic | See, FIG. 15C | |
| Acetone | 1:30 Salt: Solvent at 70° C. | No clear solution observed. Fluffy nature observed during heating | Partial disintegration of salt is observed based on NMR pattern, DSC shows spectrum with a melting point of 294.5° C., crystal Form M | See, FIG. 15D, FIG. 12 | 98.53 |
| Ethyl acetate | 1:30 Salt: Solvent at 70° C. | No clear solution observed. Fluffy nature observed during heating | NMR complies with authentic, DSC shows broad melting point of 114.5° C. | See, FIG. 15G | 98.76 |
| Isopropyl acetate | 1:30 Salt: Solvent at 70° C. | No clear solution observed. Fluffy nature observed during heating | NMR complies with authentic, DSC shows melting point of 136.3° C., crystal Form L | See, FIG. 15F, FIG. 11 | 98.99 |
| NMP | 1:10 Salt: Solvent at 70° C. | Clear solution observed. On cooling MTBE added for precipitation | Partial disintegration of salt is observed based on NMR pattern | See, FIG. 15E | 93.74 |

Example 9. Preparation of Leukadherin LA1 Choline Salt Form G

Leukadherin LA1 (~200 mg) and ~46% choline hydroxide solution in water in a 1:1 ratio were slurried in a tetrahydrofuran:methanol (3:1, 0.7 mL) solution in a glass vial and the mixture stirred at 50° C. with a slow evaporation under nitrogen atmosphere. A dark red solid was collected.

Alternatively, Leukadherin LA1 (~200 mg) and ~46% choline hydroxide solution in water in a 1:1 ratio were slurried in an ethanol:t-butyl methyl ether (2:1, 0.7 mL) solution in a glass vial and the mixture stirred at 40° C. for 2 hours. Solids were isolated by vacuum filtration, washed with methyl t-butyl ether and air dried. A dark red solid was collected. 1H NMR (500 MHz, DMSO) δ 7.95 (d, 2H, J=6.8 Hz), 7.75 (d, 2H, J=7.3 Hz), 7.72 (s, 1H), 7.40 (d, 1H, J=3.8 Hz), 7.37-7.27 (m, 6H), 5.26 (s, 2H), 3.87-3.83 (m, 2H), 3.42-3.39 (m, 2H), 3.11 (s, 9H).

Form G produces a unique powder X-ray diffraction pattern (Table 14).

TABLE 14

Powder X-ray diffraction peak positions and intensities for Leukadherin LA1 Choline Salt Form G

| Position 2θ (Copper) | Intensity |
|---|---|
| 5.555 | 1684 |
| 7.869 | 685 |
| 11.158 | 1298 |
| 13.329 | 769 |
| 15.045 | 1133 |
| 15.656 | 825 |
| 16.072 | 1512 |
| 16.202 | 639 |
| 16.475 | 793 |
| 16.644 | 1734 |
| 17.801 | 509 |
| 18.113 | 520 |
| 18.49 | 683 |
| 19.062 | 1192 |
| 19.829 | 600 |
| 20.024 | 603 |
| 21.051 | 557 |
| 22.949 | 509 |
| 24.639 | 1051 |
| 24.964 | 1146 |
| 25.575 | 1881 |
| 26.641 | 461 |
| 26.823 | 613 |
| 26.901 | 539 |
| 29.28 | 368 |
| 29.683 | 334 |
| 30.58 | 286 |
| 30.697 | 332 |
| 34.415 | 215 |

Example 10. Preparation of Leukadherin LA1 Choline Salt Form O

Leukadherin LA1 (~200 mg) and ~46% choline hydroxide solution in water in a 1:1 ratio were slurried in a THF (0.7 mL) solution in a glass vial and the mixture stirred at ambient temperature overnight. Solids were isolated by vacuum filtration and air dried. A dark red solid was collected. 1H NMR (500 MHz, DMSO) δ 7.95 (d, 2H, J=6.8 Hz), 7.75 (d, 2H, J=7.3 Hz), 7.72 (s, 1H), 7.40 (d, 1H, J=3.8 Hz), 7.37-7.27 (m, 6H), 5.26 (s, 2H), 3.87-3.83 (m, 2H), 3.42-3.39 (m, 2H), 3.11 (s, 9H).

Form O produces a unique powder X-ray diffraction pattern (Table 15).

TABLE 15

Powder X-ray diffraction peak positions and intensities for Leukadherin LA1 Choline Salt Form O

| Position 2θ (Copper) | Intensity |
|---|---|
| 8.35 | 1010 |
| 8.792 | 1057 |
| 9.286 | 998 |
| 13.251 | 806 |
| 14.304 | 826 |
| 16.735 | 1365 |
| 17.008 | 826 |
| 18.074 | 731 |
| 19.426 | 784 |
| 19.647 | 735 |
| 19.907 | 777 |
| 20.661 | 765 |
| 20.934 | 605 |
| 21.402 | 609 |
| 21.727 | 850 |
| 22.52 | 661 |
| 23.417 | 669 |
| 24.145 | 722 |
| 25.458 | 610 |
| 25.549 | 587 |

Example 11. Preparation of Leukadherin LA1 Choline Salt Form Q

Leukadherin LA1 (~200 mg) and ~46% choline hydroxide solution in water in a 1:1 ratio were slurried in a acetone (0.7 mL) solution in a glass vial and the mixture stirred at ambient temperature overnight. Solids were isolated by vacuum filtration and air dried. A dark red solid was collected. Alternatively, Leukadherin LA1 (~200 mg) and ~46% choline hydroxide solution in water in a 1:1 ratio were slurried in a ethyl acetate (0.7 mL) solution in a glass vial and the mixture stirred at ambient temperature overnight. Solids were isolated by vacuum filtration and air dried. A dark red solid was collected. 1H NMR (500 MHz, DMSO) δ 7.95 (d, 2H, J=6.8 Hz), 7.75 (d, 2H, J=7.3 Hz), 7.72 (s, 1H), 7.40 (d, 1H, J=3.8 Hz), 7.37-7.27 (m, 6H), 5.26 (s, 2H), 3.87-3.83 (m, 2H), 3.42-3.39 (m, 2H), 3.11 (s, 9H).

Form Q produces a unique powder X-ray diffraction pattern (Table 16).

TABLE 16

Powder X-ray diffraction peak positions and intensities for Leukadherin LA1 Choline Salt Form

| Position 2θ (Copper) | Intensity |
|---|---|
| 4.996 | 2333 |
| 5.23 | 932 |
| 8.35 | 2283 |
| 9.585 | 1626 |
| 9.91 | 1604 |
| 11.548 | 1112 |
| 12.64 | 1272 |
| 12.822 | 1947 |
| 13.303 | 2639 |
| 14.369 | 1193 |
| 15.812 | 937 |
| 16.085 | 834 |
| 16.579 | 1095 |
| 17.541 | 1074 |
| 17.957 | 1194 |
| 19.283 | 2225 |
| 20.557 | 857 |
| 20.726 | 1096 |
| 21.467 | 1046 |
| 21.74 | 1114 |
| 22.884 | 925 |
| 23.703 | 1447 |
| 24.847 | 1082 |
| 25.094 | 793 |
| 25.263 | 800 |
| 25.302 | 813 |
| 25.341 | 812 |
| 25.497 | 2964 |
| 26.329 | 749 |
| 26.927 | 728 |
| 26.979 | 727 |
| 28.136 | 803 |
| 28.773 | 560 |
| 30.424 | 505 |
| 31.204 | 534 |
| 31.958 | 409 |
| 35.702 | 386 |
| 37.392 | 335 |

Differential Scanning Calorimetry

Table 17 shows the melting temperatures of various forms of choline and meglumine salts.

TABLE 17

DSC thermogram readings of various forms of salts

| Form type | Melt Onset (° C.) | Melt Peak (° C.) | Enthalpy (J/g) |
|---|---|---|---|
| Form A | | | |
| Form G | | | |
| Form H | | | |
| Form O | | | |
| Form R | 221.45 | 224.48 | 157.5 |
| Form S | | | |
| Form L | 132.13 | 136.32 | 59.29 |
| Form M | 276.23 | 294.45 | 46.18 |
| Form N | 130.18 | 139.87 | 84.91 |

Example 12. Purification of LA1 Choline Salt Polymorphs

Choline salts were purified through recrystallization by heating at various temperatures or at room temperature in protic and aprotic solvents as shown in Table 18 and Table 19. Table 18 shows polymorph screening of choline salt in protic solvents, and Table 19 shows polymorph screening of choline salt in aprotic solvents. The protic solvents included methanol, ethanol, isopropyl alcohol, n-butanol and water. The aprotic solvents included acetone, ethyl acetate, dimethyformamide (DMF), dimethyl sulfoxide (DMSO), isopropyl alcohol (IPA), tetrahydrofuran (TI-IF), acetonitrile (ACN) and N-methyl pyrrolidone (NMP). The precipitation occurred at room temperature. No clear solution was observed on heating. FIGS. 16A-L show XRPD patterns obtained for LA1 choline salts in various solvents separately. The crystalline form R was obtained in n-butanol, at 70° C., and is characterized by an X-ray powder diffraction (XRPD) pattern in accordance with FIG. 7 (and FIG. 16A), as determined on a diffractometer using Cu-Kα radiation. The crystalline form S was obtained in methanol, at 70° C., and is characterized by an X-ray powder diffraction (XRPD) pattern in accordance with FIG. 8 (FIG. 16L), as determined on a diffractometer using Cu-Kα radiation.

Example 13. Characterization of LA1 Free Acid Pharmacokinetic Properties in Rats The absolute oral and intraperitoneal bioavailability of LA1 was evaluated in Sprague Dawley (SD) rats following a single oral and IP route (2 mg/kg) and IV (1 mg/kg) administration of LA 1.

In a first experiment, the dose solution was prepared in 30% w:v 2-hydroxypropyl-β-cyclodextrin prepared in PBS at 2 mg/kg. Clearance (ml/min/kg) and bioavailability (AUC in mM*hr) are summarized in Table 20. Improved bioavailability was needed.

TABLE 18

Polymorph screening of choline salt in protic solvents

| Solvent | Condition | Observation | Remarks | XPRD | HPLC Purity (A %) |
|---|---|---|---|---|---|
| Methanol | 1:20 Salt:Solvent at 70° C. | Clear solution observed. Precipitation occurs after cooling | NMR complies with authentic | See, FIG. 16B, FIG. 8 | 99.93 |
| Ethanol | 1:20 Salt:Solvent at 70° C. | Clear solution observed. Precipitation occurs after cooling | NMR complies with authentic | — | |
| IPA | 1:20 Salt:Solvent at 70° C. | No clear solution observed | NMR complies with authentic | See, FIG. 16F | |
| IPA | 1:20 Salt:Solvent at 25-30° C. | No clear solution observed | NMR complies with authentic | See, FIG. 16E | |
| n-Butanol | 1:20 Salt:Solvent at 120° C. | Clear solution observed. Precipitation observed upon cooling at RT | NMR complies with authentic, crystal Form R | See, FIG. 16A, FIG. 7 | >99 (by LCMS) |
| Methanol | 1:20 Salt:Solvent at 25-30° C. | Clear solution observed. Precipitation occurs after ageing | NMR complies with authentic, crystal Form S | See, FIG. 16L, FIG. 8 | 99.47 |
| Ethanol | 1:20 Salt:Solvent at 25-30° C. | Clear solution not observed | NMR complies with authentic | See, FIG. 16G | 99.75 |
| H$_2$O | 1:20 Salt:Solvent at 25-30° C. | Turbid solution observed | Non filterable | — | |

TABLE 19

Polymorph screening of choline salt in aprotic solvents

| Solvent | Condition | Observation | Remarks | XPRD | HPLC Purity (A %) |
|---|---|---|---|---|---|
| Isopropyl acetate | 1:20 Salt:Solvent at 70° C. | No clear solution observed. Fluffy nature observed during heating | NMR complies with authentic | See, FIG. 16D | 89.61 |
| Isopropyl acetate | 1:20 Salt:Solvent at 25-30° C. | No clear solution observed. Fluffy nature observed during heating | NMR complies with authentic | See, FIG. 16C | 97.85 |
| Acetone | 1:20 Salt:Solvent at 70° C. | No clear solution observed. Fluffy nature observed during heating | NMR complies with authentic | See, FIG. 16K | 99.62 |
| Acetone | 1:20 Salt:Solvent at 25-30° C. | No clear solution observed. Fluffy nature observed during heating | NMR complies with authentic | See, FIG. 16J | 99.44 |
| Ethyl acetate | 1:20 Salt:Solvent at 70° C. | No clear solution observed. Fluffy nature observed during heating | NMR complies with authentic | See, FIG. 16I | 98.56 |
| Ethyl acetate | 1:20 Salt:Solvent at 25-30° C. | No clear solution observed. Fluffy nature observed during heating | NMR complies with authentic | See, FIG. 16H | 98.77 |

TABLE 20

PK data for LA1 free acid for PO administration

| DMPK<br>PO - 2 mg/kg | LA1 Free Acid |
|---|---|
| Rat Cl (ml/min/kg) | 11.1 |
| Rat F % (AUC in mM*hr) | 15.1% (8.7) |
| Vss (L) | 0.59 |
| $t_{1/2}$ (hr) | 2.03 |
| MRT (hr) | 3.49 |

In a second experiment, the dose solution was prepared in Tween-80 (0.02%) and 0.5% methyl cellulose in Milli-Q water. IP (2 mg/kg) and IV (1 mg/kg) dose solutions were prepared in a 5% DMSO and 95% PEG-200. Rat PK shows reasonable clearance of 20 ml/min/kg as shown in Table 21. The PO dosing did not achieve significant exposure to yield data for calculations. IP dosing yielded 82% bioavailability (3.5 mM*hr) PO (2 mg/kg).

TABLE 21

PK data for LA1 free acid for PO and IP administration

| | DMPK | LA1 Free Acid |
|---|---|---|
| PO - 2 mg/kg | Rat Cl (ml/min/kg) | 19.7 |
| | Rat F % (AUC in mM*hr) | Exposure too low |
| | Vss (L/kg) | 4.19 |
| | $t_{1/2}$ (hr) | Exposure too low |
| | MRT (hr) | Exposure too low |
| IP - 2 mg/kg | Rat Cl (ml/min/kg) | 19.7 |
| | Rat F % (AUC in mM*hr) | 81.6% (3.5) |
| | Vss (L/kg) | 4.19 |
| | $t_{1/2}$ (hr) | 0.78 |
| | MRT (hr) | 3.44 |

Example 14. Characterization of Micronized LA1 Free Acid Pharmacokinetic Properties in Rats The PO (2 mg/kg) dose solution was prepared in Tween-80 (0.02%) and 0.5% methyl cellulose in Milli-Q water. The IV (1 mg/kg) dose solution was prepared in a solution of 5% DMSO and 95% PEG-200. Rat PK shows reasonable clearance of 23.4 ml/min/kg as shown in Table 22. PO dosing yielded 23% bioavailability (0.76 μM*hr).

Following IV administration of LA1, the $t_{1/2}$ and clearance were found to be 1.16 h and 19.7 mL/min/Kg, respectively. The mean volume of distribution was 2.39 L/Kg. Following IP administration of LA1, the mean $C_{max}$ was 1284 ng/mL attained at 0.25 h ($t_{max}$). The $t_{1/2}$, was found to be 0.78 h. The absolute IP bioavailability was 82%.

TABLE 22

PK data for PO administration of micronized LA1 free acid

| DMPK<br>PO - 2 mg/kg | LA1 Free Acid<br>(Micronized) |
|---|---|
| Rat Cl (ml/min/kg) | 23.4 |
| Rat F % (AUC in mM*hr) | 23% (0.76) |
| Vss (L/kg) | 2.14 |
| $t_{1/2}$ (hr) | 1.10 |
| MRT (hr) | 2.04 |

Example 15. Characterization of Pharmacokinetic Properties for LA1 Salts in Rats The absolute oral and intraperitoneal bioavailability of LA1 was evaluated in SD rats following a single oral (per os, PO) and intraperitoneal (IP) dose (2 mg/kg) and intravenous (IV) (1 mg/kg) administration of LA1, LA1 choline salt, and LA1 meglumine salt. Studies were conducted with the choline salt Form Q and meglumine salt Form T prepared according to Example 5.

The PK studies were conducted as per internal IAEC approved protocol no. IAEC/JDC/2012/27. The routes of administration were namely PO (gavage), IP (bolus) and IV (bolus through tail vein). A total of four SD male rats were used aged between 5-6 weeks. The feeding regimen included 12 h fasting and the feed was provided 2 hrs after the dosage inoculation and water was provided ad libidum. The blood collection schedule for PO/IP was at 0.25, 0.5, 1, 2, 4, 8, 10 and 24 h, and for IV it was at 0.12, 0.25, 0.5, 1, 2, 4, 8 and 24 h. For PO dosage, tween-80 (0.02%) and 0.5% methyl cellulose prepared in milli-Q water were used as vehicles; for IP and IV dosage 5% DMSO and 95% PEG-200 were used as vehicles.

LA1 Dose Preparation Procedure:

For PO dosage, 2.00 mg of LA1 was wetted with ~30 μL of Tween-80 and triturated in a mortar and pestle, then slowly 0.5% of methyl cellulose was added to make up the final volume to 10.0 mL. For IP dosage, 2.050 mg of LA1 was dissolved in 100 μL of DMSO, vortexed and finally 1.90 mL of PEG-200 was added. For IV dosage, 2.010 mg of LA1 was dissolved in 200 μL of DMSO, vortexed and finally 3.80 mL of PEG-200 was added.

LA1 Choline Dose Preparation Procedure:

For PO dosage, 3.670 mg of LA1 choline salt was wetted with—30 tit of Tween-80 and triturated in a mortar and pestle, then slowly 0.5% of methyl cellulose was added to make up the final volume to 13.90 mL. For IP dosage, 4.286 mg of LA1 choline salt was dissolved in 162 μL of DMSO, vortexed and finally 3.078 mL of PEG-200 was added. For IV dosage, 2.025 mg of LA1 choline salt was dissolved in 153 μL of DMSO, vortexed and finally 2.907 mL of PEG-200 was added.

LA1 Choline Dose Preparation Procedure:

For PO dosage, 3.600 mg of LA1 meglumine salt was wetted with ~30 μL of Tween-80 and triturated in a mortar and pestle, then slowly 0.5% of methyl cellulose was added for a final volume of 11.760 mL. For IP dosage, 4.134 mg of LA1 meglumine salt was dissolved in 135 μL of DMSO, vortexed and 2.565 mL of PEG-200 was added. For IV dosage, 2.066 mg of LA1 meglumine salt was dissolved in 135 of DMSO, vortexed and finally 2.565 mL of PEG-200 was added.

Stock solution (178 μg/mL) in methanol was further diluted using methanol: water (80:20, v/v) to obtain working solutions in the range of 10.4 to 20745 ng/mL.

Methodology for Preparation of CC/QC Samples:

50 μL of sample was aliquoted in to pre-labeled vials. To it was added 200 μL of 10% tetrahydrofuran containing IS (100 ng/mL; tolbutamide) and mixed well, vortexed for 5 min followed by centrifugation for 5 min at 14000 rpm for at 4° C. Supernatant was separated and 5 μL of same was injected on LC-MS/MS.

Data Analysis: Individual concentration-time data were analyzed using WinNonlin (Version 5.3) by non-compartmental analysis (NCA) method.

Results:

Rat PK showed reasonable clearance of 18 ml/min/kg as shown in Table 23. PO dosing yielded 41% bioavailability (1.5 mM*hr). IP dosing yielded 84% bioavailability (3.2 mM*hr). PO (2 mg/kg) dose solution was prepared in Tween-80 (0.02%) and 0.5% methyl cellulose in Milli-Q water. The IP (2 mg/kg) and IV (1 mg/kg) dose solutions were prepared in a 5% DMSO and 95% PEG-200.

Results for the LA1 choline salt are shown in Table 23. Following oral administration of LA1 choline salt, the maximum plasma concentration for LA1 (Cmax: 477 ng/mL) was attained at 0.50 h (tmax). The $t_{1/2}$ was found to be 1.57 h. The absolute oral bioavailability was 41%. Following IP administration of LA1 choline salt, the mean Cmax for LA1 was 1590 ng/mL, which was attained at 0.25 h (tmax). The $t_{1/2}$ was found to be 1.60 h. The absolute IP bioavailability was 84%. Following IV administration of LA1 choline salt, the $t_{1/2}$ and clearance was found to be 1.21 h and 17.6 mL/min/kg, respectively for LA1. The mean volume of distribution was 1.78 lit/kg.

TABLE 23

PK data of LA1 choline salt for PO and IP administration

| | DMPK | LA1 Choline Salt |
|---|---|---|
| PO - 2 mg/kg | Rat Cl (ml/min/kg) | 17.6 |
| | Rat F % (AUC in mM*hr) | 41.0% (1.5) |
| | Vss (L/kg) | 0.73 |
| | $t_{1/2}$ (hr) | 1.57 |
| | MRT (hr) | 1.81 |
| IP - 2 mg/kg | Rat Cl (ml/min/kg) | 17.6 |
| | Rat F % (AUC in mM*hr) | 83.9% (3.2) |
| | Vss (L/kg) | 0.73 |
| | $t_{1/2}$ (hr) | 1.60 |
| | MRT (hr) | 1.02 |

Rat PK showed reasonable clearance of 18 ml/min/kg as shown in Table 24. PO dosing of the LA1 meglumine salt yielded an excellent 37% bioavailability (1.2 mM*hr). The LA1 meglumine salt showed a bioavailability of greater than 100% (167%, 5.3 mM*hr) for intraperitoneal (IP) administration. A possible cause for >100% bioavailability is enterohepatic circulation. Enterohepatic circulation refers to the circulation of biliary acids, bilirubin, drugs, or other substances from the liver to the bile, followed by entry into the small intestine, and reabsorption by the enterocyte and transport back to the blood stream.

Results for the LA1 meglumine salt are shown in Table 24. Following oral administration of LA1 meglumine salt, the mean Cmax (463 ng/mL) for LA1 was attained at 0.50 h (tmax). The $t_{1/2}$ was found to be 1.60 h. The absolute oral bioavailability was 37%. Following IP administration of LA1 meglumine salt, the mean Cmax for LA1 was 2865 ng/mL, which attained at 0.25 h (tmax). The $t_{1/2}$ was found to be 1.95 h. The mean absolute IP bioavailability was >100%. Following IV administration of LA1 meglumine salt, the $t_{1/2}$ and clearance was found to be 1.41 h and 17.5 mL/min/Kg, respectively for LA1. The mean volume of distribution was 1.85 L/Kg.

TABLE 24

PK data of LA1 meglumine salt for PO and IP administration

| | DMPK | LA1 Meglumine Salt |
|---|---|---|
| PO - 2 mg/kg | Rat Cl (ml/min/kg) | 17.5 |
| | Rat F % (AUC in mM*hr) | 37.1% (1.2) |
| | Vss (L/kg) | 0.74 |
| | $t_{1/2}$ (hr) | 1.60 |
| | MRT (hr) | 1.54 |
| IP - 2 mg/kg | Rat Cl (ml/min/kg) | 17.5 |
| | Rat F % (AUC in mM*hr) | 167% (5.3) |
| | Vss (L/kg) | 0.74 |
| | $t_{1/2}$ (hr) | 1.95 |
| | MRT (hr) | 1.54 |

Both the LA1 choline salt and the LA1 meglumine salt showed similar bioavailability following oral administration. IP bioavailability for the LA1 meglumine salt was greater than the IP bioavailability for the LA1 and the LA1 choline salt. LA1, the LA1 choline salt, and the LA1 meglumine salt exhibited similar pharmacokinetic profiles following IV administration.

The pharmacokinetics of LA1, LA1 meglumine and LA1 choline in Sprague Dawley (SD) rats following intravenous, intraperitoneal and oral administration at 1, 2, and 2 mg/kg, respectively, were assessed.

Figure 17:
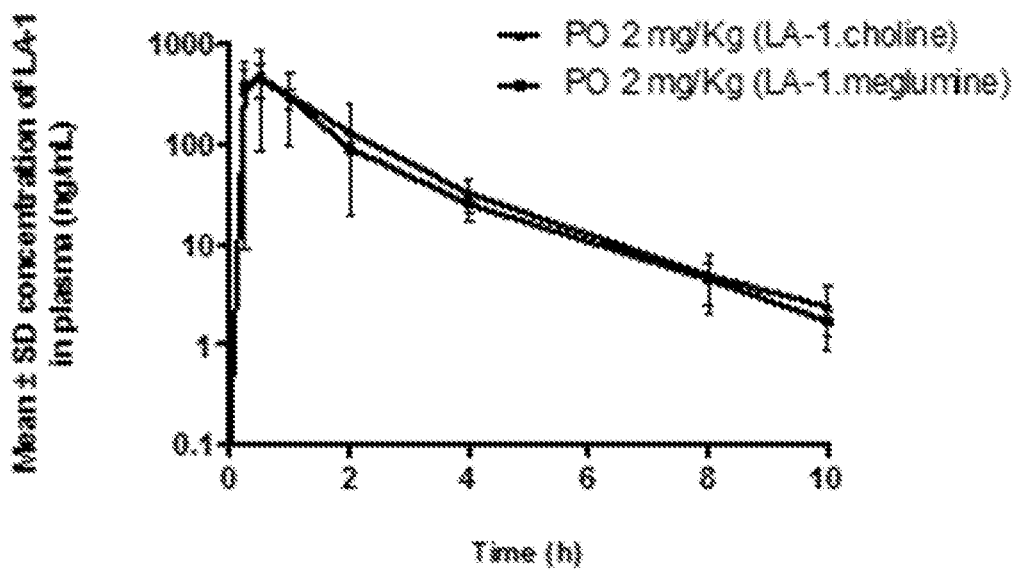
FIG. 17 shows the concentration vs. time profile of LA1 following oral administration of micronized LA1 (2 mg/kg) to Sprague Dawley rats.

Table 25 provides a comparative account of the pharmacokinetic parameters of LA1 in SD rats after an oral dose of LA1, LA1 choline and LA1 meglumine at 2 mg/kg. FIG. 17 shows the concentration vs. time profile of LA1 released following oral administration of LA1 choline salt (2 mg/kg) and LA1 meglumine salt (2 mg/kg) to SD rats.

TABLE 25

Comparison of the PK data for oral administration of various salts

| | | LA1 | | LA1 choline | | LA1 meglumine | |
|---|---|---|---|---|---|---|---|
| PK parameter | | Mean | SD | Mean | SD | Mean | SD |
| $t_{1/2,\beta}$ | (h) | PK | | 1.57 | 0.30 | 1.60 | 0.35 |
| $AUC_{0-t}$ | (ng · h/mL) | parameters | | 808 | 555 | 722 | 109 |
| $AUC_{0-\infty}$ | (ng · h/mL) | could not | | 814 | 560 | 726 | 110 |
| $C_{max}$ | (ng/mL) | be | | 477 | 388 | 463 | 168 |
| $t_{max}$ | (h) | calculated | | 0.50 | 0.00 | 0.50 | 0.00 |
| MRT | (h) | due low | | 1.81 | 0.45 | 1.54 | 0.28 |
| $T_{last}$ | (h) | exposure | | 10.0 | 0.00 | 10.0 | 0.00 |
| F | (%) | NA | | 41.0 | | 37.1 | |

Figure 18:
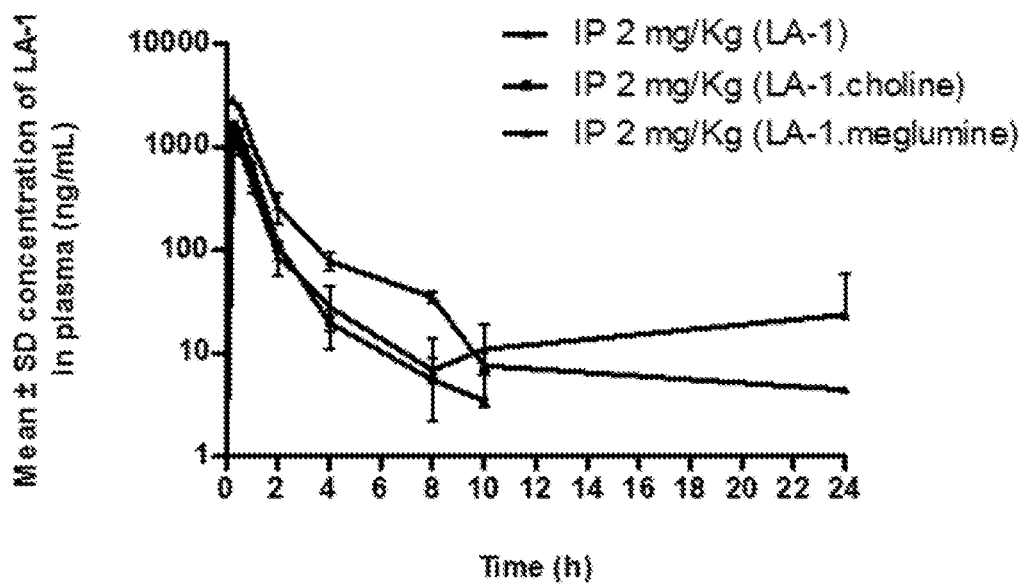
FIG. 18 shows concentration vs. time profiles of LA1 following IP administration of LA1 (2 mg/kg), and LA1 released following IP administration of LA1 choline (2 mg/kg) and LA1 meglumine (2 mg/kg) to Sprague Dawley rats.

Table 26 provides a comparative account of the pharmacokinetic parameters of LA1 in SD rats after an IP dose of LA1, LA1 choline salt and LA1 meglumine salt at 2 mg/kg. FIG. 18 shows concentration vs. time profile of LA1 following intraperitoneal administration of LA1 (2 mg/kg) and LA1 released following intraperitoneal administration of LA1 choline (2 mg/kg) and LA1 meglumine (2 mg/kg) to SD rats.

TABLE 26

Comparison of PK parameters for IP administration of various salts

| | | LA1 | | LA1 choline | | LA1 meglumine | |
|---|---|---|---|---|---|---|---|
| PK parameter | | Mean | SD | Mean | SD | Mean | SD |
| $t_{1/2,\beta}$ | (h) | 0.78 | 0.17 | 1.60 | 0.10 | 1.95 | 0.24 |
| $AUC_{0-t}$ | (ng · h/mL) | 1481 | 255 | 1657 | 115 | 3252 | 191 |
| $AUC_{0-\infty}$ | (ng · h/mL) | 1499 | 268 | 1666 | 122 | 3270 | 183 |

TABLE 26-continued

Comparison of PK parameters for IP administration of various salts

| PK parameter | | LA1 Mean | LA1 SD | LA1 choline Mean | LA1 choline SD | LA1 meglumine Mean | LA1 meglumine SD |
|---|---|---|---|---|---|---|---|
| $C_{max}$ | (ng/mL) | 1284 | 258 | 1590 | 190 | 2865 | 87.2 |
| $t_{max}$ | (h) | 0.25 | 0.00 | 0.25 | 0.00 | 0.25 | 0.00 |
| MRT | (h) | 3.44 | 3.58 | 1.02 | 0.09 | 1.54 | 0.27 |
| $T_{last}$ | (h) | 20.5 | 7.00 | 10.0 | 0.00 | 17.0 | 8.08 |
| % F | | | 81.6 | | 83.9 | | >100 |

Figure 19:
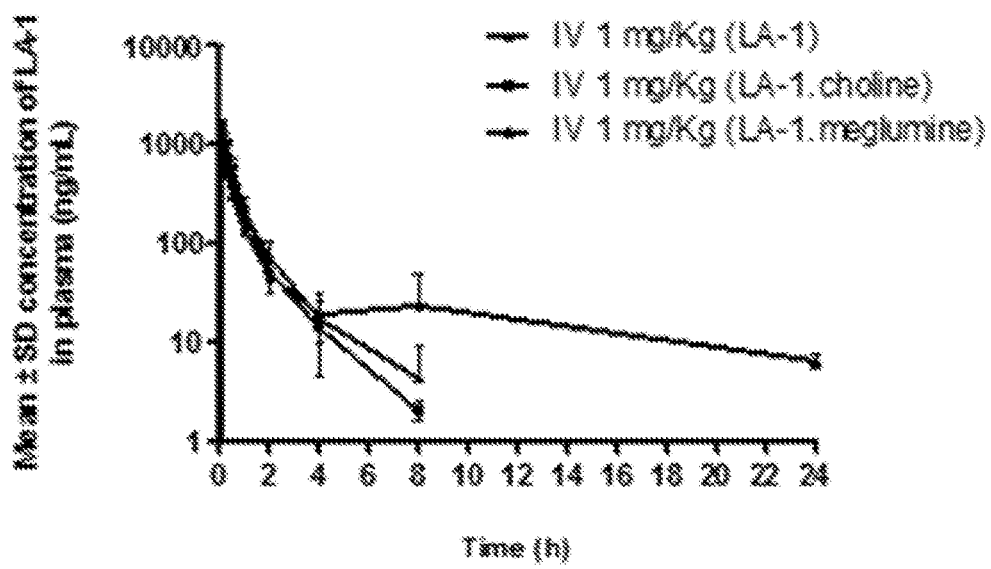
FIG. 19 shows concentration vs. time profiles of LA1 following IV administration of LA1 (1 mg/kg), and LA1 released following IV administration of LA1 choline (1 mg/kg) and LA1 meglumine (1 mg/kg) to Sprague Dawley rats.

Table 27 provides a comparative account of the pharmacokinetic parameters of LA1 in SD rats after an IV dose of LA1, LA1 choline salt and LA1 meglumine salt at 1 mg/kg. FIG. 19 shows the concentration vs. time profile of LA1 following intravenous administration of LA1 (1 mg/kg) and LA1 released following intravenous administration of LA choline (1 mg/kg) and LAI meglumine (1 mg/kg) to SD rats.

TABLE 27

Comparison of the PK parameters for IV administration of various salts

| PK parameter | | LA1 Mean | LA1 SD | LA1 choline Mean | LA1 choline SD | LA1 meglumine Mean | LA1 meglumine SD |
|---|---|---|---|---|---|---|---|
| $t_{1/2,\beta}$ | (h) | 1.16 | 0.34 | 1.21 | 0.20 | 1.41 | 0.33 |
| $C_{max}$ | (ng/mL) | 952 | 143 | 1418 | 266 | 1445 | 314 |
| $C_0$ | (ng/mL) | 1317 | 270 | 1856 | 392 | 2142 | 410 |
| $AUC_{0-t}$ | (ng·h/mL) | 903 | 339 | 985 | 249 | 967 | 168 |
| $AUC_{0-\infty}$ | (ng·h/mL) | 918 | 335 | 993 | 245 | 978 | 173 |
| CL | (mL/min/kg) | 19.7 | 5.90 | 17.6 | 4.30 | 17.5 | 3.08 |
| Vd | (L/kg) | 2.39 | 1.31 | 1.78 | 0.60 | 1.85 | 0.46 |
| Vss | (L/kg) | 4.19 | 1.80 | 0.73 | 0.17 | 0.74 | 0.27 |
| MRT | (h) | 3.38 | 1.45 | 0.72 | 0.03 | 0.91 | 0.39 |
| $T_{last}$ | (h) | 20.0 | 8.00 | 7.00 | 2.00 | 8.00 | 0.00 |

Example 16. Characterization of Pharmacokinetic Properties for LA1 Formulations in Rats The routes of administration were namely PO (gavage) and IV (bolus through tail vein). A total of four SD male rats were used aged between 5-6 weeks. The feeding regimen included 12 h fasting and the feed was provided 2 hrs after the dosage inoculation and water was provided ad libitum. The blood collection schedule for PO was at 0.25, 0.5, 1, 2, 4, 8, 10 and 24 h, and for IV it was at 0.12, 0.25, 0.5, 1, 2, 4, 8 and 24 h. For PO dosage, tween-80 (0.02%) and 0.5% methyl cellulose prepared in milli-Q water were used as vehicles; for IV dosage 10% DMSO and 90% PEG-200 were used as vehicles.

Dose Preparation:

For PO dosage, 2.582 mg of LA1 was wetted with ~30 μL of Tween-80 and triturated in a mortar and pestle, then slowly 0.5% of methyl cellulose was added to make up the final volume to 12.910 mL. For IV dosage, 2.196 mg of LA1 was dissolved in 440 μL of DMSO, vortexed and finally 3.952 mL of PEG-200 was added.

Results:

Table 28 shows a comparative account of pharmacokinetic parameters of micronized LA1 in SD rats after an oral dose of 2 mg/kg w.r.t LA1 choline and LA1 meglumine.

TABLE 28

Comparison of the PK data for oral administration of LA1 formulations

| PK parameter | | *LA1 Mean | *LA1 SD | LA1 (micronized) Mean | LA1 (micronized) SD | LA1 choline salt Mean | LA1 choline salt SD | LA1 meglumine salt Mean | LA1 meglumine salt SD |
|---|---|---|---|---|---|---|---|---|---|
| $t_{1/2,\beta}$ | (h) | | | 1.10 | 0.27 | 1.57 | 0.30 | 1.60 | 0.35 |
| $AUC_{0-t}$ | (ng·h/mL) | | | 319 | 79.0 | 808 | 555 | 722 | 109 |
| $AUC_{0-\infty}$ | (ng·h/mL) | | | 336 | 93.4 | 814 | 560 | 726 | 110 |
| $C_{max}$ | (ng/mL) | | | 123 | 3.40 | 477 | 388 | 463 | 168 |
| $t_{max}$ | (h) | | | 0.88 | 0.75 | 0.50 | 0.00 | 0.50 | 0.00 |
| MRT obs | (h) | | | 2.04 | 3.00 | 1.81 | 0.45 | 1.54 | 0.28 |
| $T_{last}$ | (h) | | | 6.50 | 3.00 | 10.0 | 0.00 | 10.0 | 0.00 |
| F | (%) | NA | | 23.0 | | 41.0 | | 37.1 | |

*PK parameters could not be calculated due to low exposure.

Table 29 shows a comparative account of pharmacokinetic parameters of micronized LA1 in SD rats after an IV dose of 1 mg/kg w.r.t LA1 choline and LA1 meglumine.

TABLE 29

Comparison of the PK data for IV administration of LA1 formulations

| PK parameter | | LA1 Mean | LA1 SD | LA1 (micronized) Mean | LA1 (micronized) SD | LA1 choline salt Mean | LA1 choline salt SD | LA1 meglumine salt Mean | LA1 meglumine salt SD |
|---|---|---|---|---|---|---|---|---|---|
| $t_{1/2,\beta}$ | (h) | 1.16 | 0.34 | 1.36 | 0.57 | 1.21 | 0.20 | 1.41 | 0.33 |
| $C_{max}$ | (ng/mL) | 952 | 143 | 822 | 160 | 1418 | 266 | 1445 | 314 |
| $C_0$ | (ng/mL) | 1317 | 270 | 1025 | 217 | 1856 | 392 | 2142 | 410 |
| $AUC_{0-t}$ | (ng · h/mL) | 903 | 339 | 715 | 126 | 985 | 249 | 967 | 168 |
| $AUC_{0-\infty}$ | (ng · h/mL) | 918 | 335 | 729 | 131 | 993 | 245 | 978 | 173 |
| CL | (mL/min/kg) | 19.7 | 5.90 | 23.4 | 3.96 | 17.6 | 4.30 | 17.5 | 3.08 |
| Vd | (L/kg) | 2.39 | 1.31 | 2.63 | 1.07 | 1.78 | 0.60 | 1.85 | 0.46 |
| Vss | (L/kg) | 4.19 | 1.80 | 2.14 | 0.45 | 0.73 | 0.17 | 0.74 | 0.27 |
| MRT obs | (h) | 3.38 | 1.45 | 1.47 | 0.17 | 0.72 | 0.03 | 0.91 | 0.39 |
| $T_{last}$ | (h) | 20.0 | 8.00 | 12.0 | 8.00 | 7.00 | 2.00 | 8.00 | 0.00 |

The absolute oral and intraperitoneal bioavailability of LA1 was evaluated in SD rats following a single oral and IV (1 mg/kg) administration of micronized LA1. Following oral administration of micronized LA1, maximum plasma concentrations for LA1 ($C_{max}$: 123 ng/mL) was attained at 0.88 h ($t_{max}$). The $t_{1/2}$, was found to be 1.10 h and the absolute oral bioavailability was 23%. Following IV administration of micronized LA1, the $t_{1/2}$, and clearance was found to be 1.36 h and 23.4 mL/min/kg, respectively. Also, the mean volume of distribution was 2.63 lit/kg.

It is concluded that micronized LA1 shows better systemic exposure when compared to LA1 following oral administration. However, LA1 and micronized LA1 have shown similar pharmacokinetic profile following IV administration.

Example 17. Characterization of Pharmacokinetic Properties for LA1 Free Acid in Dogs Dog PK shows great clearance of 2.1 ml/min/kg as shown in Table 30. Oral dosing yielded an excellent 50% bioavailability. (6.1 mM*hr). The PO (2 mg/kg) dose solution of micronized LA1 was prepared in 0.1% Tween-80 0.5% (w/v) and methyl cellulose in water. The IV (0.5 mg/kg) dose solutions were prepared in a 5% DMSO, 90% PEG-200 and 5% ethanol.

TABLE 30

PK data for oral administration of LA1 free acid in dogs

| | DMPK | LA1 Free Acid |
|---|---|---|
| PO - 2 mg/kg | Dog Cl (ml/min/kg) | 2.1 |
| | Dog F % (AUC in mM*hr) | 50 (6.1) |
| | $Vd_{ss}$ (mL) | 0.72 |
| | $t_{1/2}$ (hr) | 2.11 |
| | MRT (hr) | Not Calculated |

The objective of the study was to investigate the preclinical pharmacokinetic profile of LA1 (micronized powder) in Beagle dog. To delineate the plasma concentration vs. time curve and characterize the relevant pharmacokinetic parameters to generate data on the PK properties viz., bioavailability, half-life ($b_{1/2}$), volume of distribution, $C_{max}$, $T_{max}$, AUC and elimination rate constant of LA1 in Beagle dog.

LA1 was a coarse material which was micronized using laboratory scale ball mill. In the processes particle size of LA1 was reduced to ~20 microns. The micronized LA1 was recovered, weighed and stored in glass container at room temperature. For intravenous drug administration, LA1 excipient compatibility assay for dosing in dogs were carried out. From the test results, a clear solution was obtained using the formulation mixture; 5% DMSO+90% Polyethylene glycol 400 (PEG-400)+5% ethanol.

Micronization of test Item LA1: The particle size of LA1 was reduced ~20 microns using laboratory scale ball mill. In brief, a known amount of LA1 was loaded to a cylindrical capped container made of stainless steel followed by addition of stainless steel balls. The ball mills were rotated on their axis for total of 60 minutes (6 cycles X 10 minutes). The micronized LA1 was recovered, weighed and stored in glass bottle at room temperature.

Test system: Healthy Beagle dog weighing 10-12 kg (age 10 months), males were used for the study. Crossover design was adopted for the experiments wherein 02 dogs were used in the study for oral and intravenous administration. Both the animals were housed stainless steel cage provided with a hopper to hold pellet feed and a separate water hopper. Temperature and humidity was maintained at 22±3° C. and 40-70%, respectively. The illumination was controlled to give a sequence of 12 h light and 12 h dark cycle. All the animals were adapted to the experimental conditions for at least 5 days prior to dosing. All animals were provided with Pedigree™ standard pellet feed, except for 10 to 12 h before treatment and 4 h after the drug administration. Water was provided ad libidum.

Formulation and drug administration: Exactly 90 mg of the test item LA1 (micronized powder) was weighed and transferred to a mortar and briefly triturated with pestle. Small volume of vehicle [0.5% (w/v) Carboxy methyl cellulose with 0.1% Tween-80] in water was then added slowly with continuous trituration until a uniform suspension was obtained. The content was then transferred into the measuring cylinder. The mortar was rinsed till the complete transfer of test item into the measuring cylinder was ensured. The final volume was then made up to 225 mL with vehicle to get a uniform suspension with desired concentration of 0.4 mg/mL. Dosing formulations were given by oral gavage at a dose volume not exceeding 5 mL/kg.

Intravenous drug formulation: Hemolysis assay using dog whole blood was employed to assess the damage of red blood cells for selection of excipient for intravenous dosing.

Based on the results obtained, the described procedure was adopted. Exactly 22.5 mg of the test item (micronized powder) was weighed into a graduated tube. 2.25 mL of DMSO was added drop wise and mixed by vortex. Then, 40.50 mL of Polyethylene glycol 400 (PEG-400) was added in two to three fragments and vortex intermittently. Then 2.25 mL Ethanol was added drop wise and vortex to get clear solution. The formulation was subjected to ultra-sonication for 5 minutes. Dose administration was carried out using infusion pump and was infused at the rate 0.33 mL/kg/min Dose volume did not exceeding 1 ml/kg.

Sample collection: Serial method was used for blood sampling. Blood samples were collected as mentioned in the study design section (7). The blood sample (−1.5 mL) was collected from saphenous vein into labeled tubes, containing 2% w/v $K_2$EDTA solution, as an anticoagulant. Whole blood was stored in −20° C. until taken for bio-analysis.

Extraction procedure: The plasma separated from the whole blood was used for bio-analysis. The analyte LA1 was extracted from the plasma by acetonitrile precipitation method. The supernatant from both the layers were mixed and vortexed for 10 minutes. All samples (Including CCs, QCs) were injected into LC-MS/MS system.

Data analysis: From the above plasma concentrations the pharmacokinetics analysis was performed using PK solver.

Results:

The pharmacokinetic data suggested that LA1 absorption was moderate with the peak concentration occurring at 4 hours post dose. The absorption phase showed a steady build-up of LA1 levels to reach its peak concentration. The peak concentration was found to be 685.47 ng/mL. The elimination phase of LA1 showed a steady decline immediately after the peak concentration was achieved. The oral half-life of LA1, is approximately 2 hours and the $AUC_{0-12}$ is 2572.24 h*ng/mL. The volume of distribution of LA1 was 0.72 ml with clearance being 0.39 ml/h. The absolute oral bioavailability of LA1 (micronized powder) was found to be 50.62% (0.5 mg i.v. vs 2 mg oral).

Test item concentrations in the plasma were detected in both treated animals. The pharmacokinetic profile of LA1 has shown a half-life of 2 h, $T_{max}$=4 h, $C_{max}$=685.47 ng/mL and $AUC_{0-12}$=2572.24 h*ng/mL. Table 31 provides the plasma concentrations of LA1 (micronized powder) in ng/mL in i.v. dose

TABLE 31

Plasma concentrations of micronized LA1 for IV administration at different time intervals
IV - 0.5 mg/kg Bwt (n = 03)

| Time (h) | Concentration (ng/ml) Animal No. | | | Mean | ±SD |
|---|---|---|---|---|---|
| | 1 | 2 | 3 | | |
| Pre-dose | 0.00 | 0.00 | 0.00 | 0.00 | 0.00 |
| 0.05 | 1567.58 | 1336.59 | 1083.05 | 1329.07 | 242.35 |
| 0.1 | 897.32 | 830.40 | 949.27 | 892.33 | 59.59 |
| 0.25 | 716.65 | 632.69 | 709.29 | 686.21 | 46.50 |
| 0.5 | 504.90 | 416.91 | 501.66 | 474.49 | 49.89 |
| 1 | 405.11 | 313.73 | 349.30 | 356.05 | 46.06 |
| 2 | 322.73 | 132.37 | 192.17 | 215.76 | 97.35 |
| 3 | 246.29 | 60.85 | 96.99 | 134.71 | 98.31 |
| 4 | 68.79 | 55.50 | 26.76 | 50.35 | 21.48 |
| 6 | 71.62 | 16.42 | 9.53 | 32.52 | 34.03 |
| 8 | 24.37 | 12.59 | 4.17 | 13.71 | 10.14 |
| 12 | 7.93 | 4.80 | 4.78 | 5.84 | 1.81 |

Table 32 provides the plasma concentrations of LA1 (micronized powder) in ng/mL in oral dose.

TABLE 32

Plasma concentrations of micronized LA1 for oral administration at different time intervals
Oral - 0.5 mg/kg Bwt (n = 03)

| Time (h) | Concentration (ng/ml) Animal No. | | | Mean | ±SD |
|---|---|---|---|---|---|
| | 1 | 2 | 3 | | |
| Pre-dose | 0.00 | 0.00 | 0.00 | 0.00 | 0.00 |
| 0.5 | 102.75 | 35.26 | 44.77 | 60.93 | 36.53 |
| 1 | 410.51 | 70.30 | 84.94 | 188.59 | 192.33 |
| 1.5 | 438.29 | 202.64 | 90.83 | 243.92 | 177.37 |
| 2 | 471.76 | 197.65 | 154.03 | 274.48 | 172.24 |
| 3 | 503.29 | 236.15 | 309.30 | 349.58 | 138.05 |
| 4 | 659.92 | 769.83 | 626.66 | 685.47 | 74.93 |
| 6 | 210.79 | 203.53 | 210.23 | 208.19 | 4.04 |
| 8 | 118.18 | 65.17 | 65.10 | 82.82 | 30.63 |
| 12 | 37.49 | 43.15 | 34.94 | 38.52 | 4.21 |

Table 33 provides summarized pharmacokinetic parameters of LA1 (micronized powder) in Beagle dog.

TABLE 33

Comparison of IV and oral PK paramateres in beagle dogs

| Route of administration | Half life (h) | Co/$C_{max}$ (ng/mL) | $Vd_{SS}$ (mL) | Cl (ml/h) | $T_{max}$ (h) | $AUC_{0-12\,h}$ (h * ng/mL) | $AUC_{0\text{-}inf}$ (h * ng/mL) |
|---|---|---|---|---|---|---|---|
| Intravenous (0.5 mg/kg) | 2.15 | 2041.83 | 0.72 | 0.39 | — | 1332.79 | 1350.43 |
| Oral (3 mg/kg) | 2.11 | 685.47 | — | — | 4.0 | 2572.24 | 2689.56 |

Absolute oral bioavailability of LA1 (micronized powder) is 50.62% (0.5 mg i.v vs 2 mg oral).

Figure 20:
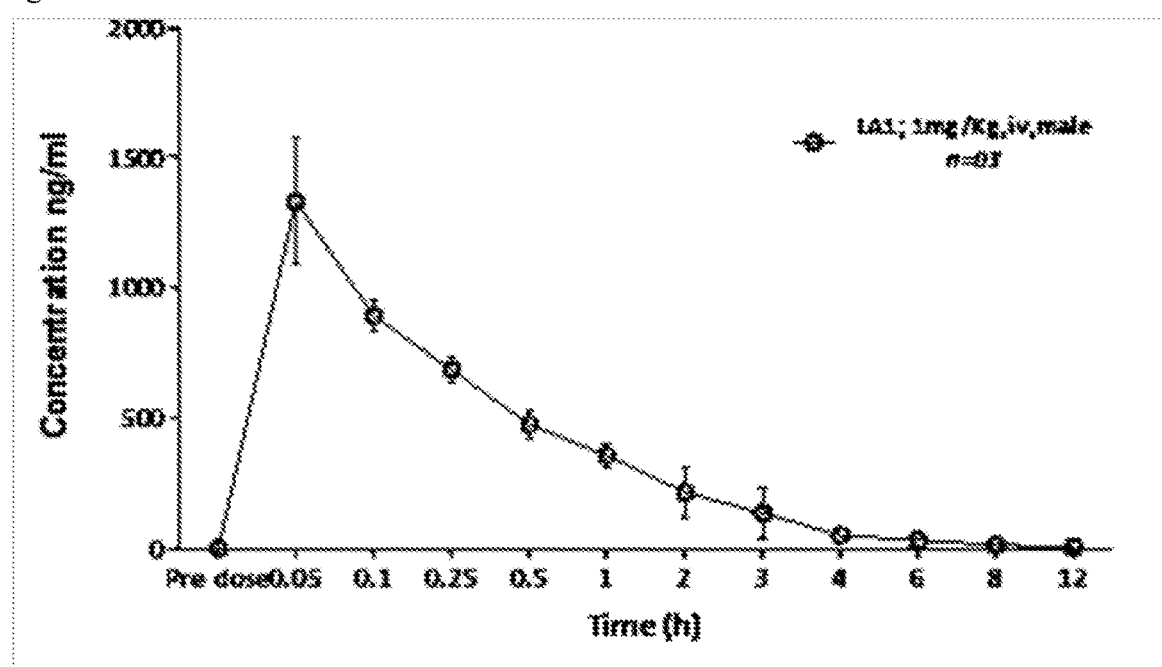
FIG. 20 shows the concentration vs. time profile of micronized LA1 (1 mg/kg) administered intravenously to beagle dogs.

Table 34 provides individual animal pharmacokinetic parameters of LA1 (micronized powder) at 0.5 mg/kg B.wt, intravenous dose in beagle dog. FIG. 20 is a graph of PK profile for LA1 in beagle dogs at an IV dosage of 1 mg/kg.

TABLE 34

Comparison of PK parameters amongst various beagle dogs for IV administration

| Animal No. | $K_{el}$ (1/hr) | Half life (hr) | $C_0$ (ng/ml) | $AUC_{inf}$ (hr * ng/mL) | $AUC_{0-12\,h}$ (hr * ng/mL) | $Vd_{ss}$ (mL) | Cl (mL/h) | Absolute Bioavailability F % |
|---|---|---|---|---|---|---|---|---|
| 1 | 0.38 | 1.82 | 1567.58 | 1798.33 | 1777.48 | 0.65 | 0.28 | 45.93 |
| 2 | 0.21 | 3.30 | 1336.59 | 1101.33 | 1078.51 | 0.88 | 0.45 | 56.88 |
| 3 | 0.52 | 1.34 | 1083.05 | 1151.64 | 1142.39 | 0.64 | 0.43 | 49.03 |
| Mean | 0.37 | 2.15 | 1329.07 | 1350.43 | 1332.79 | 0.72 | 0.39 | 50.62 |
| SD | 0.15 | 1.02 | 242.35 | 388.70 | 386.43 | 0.14 | 0.10 | 5.64 |

Figure 21:
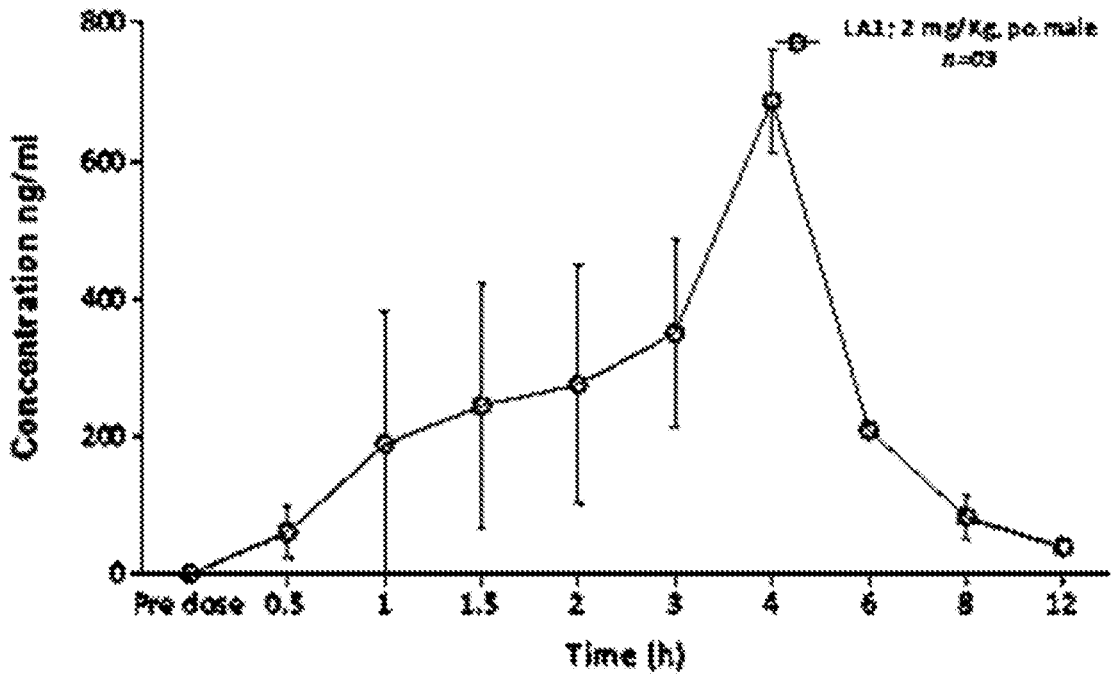
FIG. 21 shows the concentration vs. time profile of micronized LA1 (1 mg/kg) administered orally to beagle dogs.

Table 35 provides individual animal pharmacokinetic parameters of LA1 (micronized powder) 2 mg/kg, B.wt oral treatment in beagle dog. FIG. 21 shows a graph of PK profile for LA1 in beagle dogs at an oral dosage of 2 mg/kg.

TABLE 35

Comparison of PK parameters amongst various beagle dogs for oral administration

| Animal No | Kel (1/hr) | Half life (hr) | Cmax (ng/ml) | $AUC_{inf}$ (hr * ng/mL) | $T_{max}$ (hr) | $AUC_{0-12}$ (hr * ng/mL) |
|---|---|---|---|---|---|---|
| 1 | 0.29 | 2.41 | 659.92 | 3304.18 | 4.00 | 3173.88 |
| 2 | 0.35 | 1.99 | 769.83 | 2505.84 | 4.00 | 2382.10 |
| 3 | 0.36 | 1.94 | 626.66 | 2258.65 | 4.00 | 2160.72 |
| Mean | 0.33 | 2.11 | 685.47 | 2689.56 | 4.00 | 2572.24 |
| SD | 0.04 | 0.26 | 74.93 | 546.44 | 0.00 | 532.67 |

Example 18. Characterization of Pharmacokinetic Properties for LA1 Choline Salt in Dogs Test system: Healthy Beagle dog weighing 10-12 kg (age 10 months), males were used for the study. Crossover design was adopted for the experiments wherein 03 dogs were used in the study for oral and intravenous administration. The animals were housed stainless steel cage provided with a hopper to hold pellet feed and a separate water hopper. Temperature and humidity was maintained at 23±5° C. and 30-70%, respectively. The illumination was controlled to give a sequence of 12 h light and 12 h dark cycle. All the animals were adapted to the experimental conditions for at least 5 days prior to dosing. All animals were provided with Pedigree™ standard pellet feed, except for 10 to 12 h before treatment and 4 h after the drug administration. Water was provided ad libitum.

Formulation and drug administration: 251.02 mg of test item was transferred in to a clean mortar. Test item was ground uniformly using pestle. 1.235 ml of Tween 80 was added and the material was mixed. A small quantity of 0.5% (w/v) methylcellulose in water was added and the mixture was triturated. 0.5% methyl cellulose was added to make a final volume of 190 ml. Finally the above formulation was transferred to a pre-labeled beaker and sonicated for five minutes. Suspension was dosed under stirring conditions by placing on a magnetic stirrer.

The dose formulation of LA-1.choline was administered by oral gavage using a feeding gavage tube. The required volume of dose formulation (5 ml/kg body weight) was draw up into a graduated syringe. The dog was properly restrained with the help of another person so as to restrict movement. The feeding tube was inserted slowly in the mouth through the space between cheek and the teeth towards esophagus to the stomach. Proper placement of tube was confirmed by dipping the outside end of tube in a container with water and looking for air bubbles. Absence of air bubbles confirmed the location of tube in the stomach. The required dose volume of LA-1.choline suspension was slowly administered through the feeding tube. Air was pushed through at the end to ensure empting of the tube. The tube was slowly taken out and discarded.

Intravenous drug formulation: Accurately weighed 27.49 mg of test item was transferred in to the clean tube. A volume of 0.417 mL DMSO was added and mixed until the test dissolves completely. A volume 0.417 mL of Solutol: alcohol (1:1, v/v) was added and mixed, to this, 7.496 mL of normal saline was added and vortexed. Finally, the above formulation was used for dosing.

The required volume of dose formulation (0.2 ml/kg body weight) of LA-1.choline was drawn up into a graduated syringe. Air bubbles were removed from the syringe before dosing. The dog was restrained in the standing position. The upper portion of injection site of cephalic vein was compressed and the needle of the butterfly vein catheter sized 22G was slowly inserted in the vein. Once blood reached the end of the catheter tube, it was connected to the syringe. The dose formulation was immediately injected slowly. At the end of administration, approximately 0.5 mL of normal saline was injected via catheter to ensure the required dose volume was administrated. Last, the needle was removed.

Sample collection: Post-dosing ~1.5 ml of blood sample from each dog for the following time points 0.25, 0.5, 1, 1.5, 2, 3, 5, 8, 10 and 24 h was collected from the jugular vein into $K_2$EDTA containing pre-labeled vacutainer centrifuge tubes. Plasma was obtained by centrifuging blood samples at 2500 g for 10 min. under refrigeration (2-4° C.) within 0.5 h of sampling. The obtained plasma samples were transferred into pre-labeled microcentrifuge tubes (approximately ~300 µl) and stored at or below −70±10° C. The sample labels include details such as study number, test item code and dose group and/or day of sampling, animal number, time point.

Extraction procedure: The plasma separated from the whole blood was used for bio-analysis. The analyte LA1 was extracted from the plasma by acetonitrile precipitation method. The supernatant from both the layers were mixed and vortexed for 10 minutes. All samples (Including CCs, QCs) were injected into LC-MS/MS system.

Data analysis: From the above plasma concentrations the pharmacokinetics analysis was performed using PK solver.

The dog PK data for the choline salt is summarized in Table 36. The pharmacokinetic data show that peak concentration of LA1 choline salt occurred at 1.5 hours post dose.

The absorption phase showed a steady build-up of LA1 levels to reach its peak concentration. The peak concentration was found to be 2068 ng/mL. The elimination phase of LA1 showed a steady decline immediately after the peak concentration was achieved. The oral half-life of LA1, is approximately 3.4 hours and the $AUC_{0-12}$ is 9184 h*ng/mL. The volume of distribution of LA1 was 0.83 L/Kg with clearance being 3.92 ml/min/Kg. The absolute oral bioavailability of LA1.Choline Salt was found to be 43.4% (0.5 mg i.v. vs 5 mg oral).

TABLE 36

PK data for administration of LA1 Choline Salt in male beagle dogs

| | DMPK | LA1 Choline Salt |
|---|---|---|
| P0 - 5 mg/kg | Dog Cl (ml/min/kg) | 3.9 |
| | Dog F % (AUC in mM*hr) | 43.4 (22) |
| | $Vd_{ss}$ (L/kg) | 0.83 |
| | $t_{1/2}$ (hr) | 3.41 |

Table 37 shows the plasma concentrations of LA1.Choline Salt in ng/mL resulting from i.v. administration.

TABLE 37

Plasma concentrations of LA1.Choline Salt for IV administration at different time intervals

| | Time Point (h)/Concentration (ng/mL) | | | | | | | | | |
|---|---|---|---|---|---|---|---|---|---|---|
| Animal no. | 0.25 | 0.5 | 1 | 1.5 | 2 | 3 | 5 | 8 | 10 | 24 |
| 30595 | 987 | 874 | 721 | 571 | 483 | 711 | 182 | 61.9 | 51.1 | 15.8* |
| 4635 | 843 | 548 | 405 | 300 | 206 | 289 | 77.2 | 26.1 | 12.0 | BLQ |
| 30507 | 723 | 501 | 397 | 276 | 203 | 265 | 67.7 | 44.4 | 19.8 | BLQ |
| Mean conc. (ng/mL) | 851 | 641 | 508 | 382 | 297 | 421 | 109 | 44.1 | 27.6 | NA |
| SD | 132 | 203 | 185 | 164 | 161 | 251 | 64 | 17.9 | 20.7 | NA |
| % CV | 15.5 | 31.7 | 36.4 | 42.9 | 54.1 | 59.5 | 58.4 | 40.6 | 74.9 | NA |

Table 38 shows the plasma concentrations of LA1.Choline Salt in ng/mL resulting from oral administration.

TABLE 38

Plasma concentrations of LA1.Choline Salt for oral administration at different time intervals

| | Time Point (h)/Concentration (ng/mL) | | | | | | | | | |
|---|---|---|---|---|---|---|---|---|---|---|
| Animal no. | 0.25 | 0.5 | 1 | 1.5 | 2 | 3 | 5 | 8 | 10 | 24 |
| 30595 | 1003 | 1869 | 1662 | 1199 | 1485 | 1812 | 442 | 240 | 164 | 25.9 |
| 4635 | 1628 | 2776 | 2706 | 2609 | 2055 | 2510 | 429 | 104 | 62.2 | BLQ |
| 30507 | 659 | 999 | 1312 | 1055 | 1015 | 1558 | 370 | 107 | 158 | 7.88 |
| Mean conc. (ng/mL) | 1097 | 1882 | 1894 | 1621 | 1518 | 1960 | 414 | 150 | 128 | 16.9 |
| SD | 491 | 889 | 725 | 859 | 521 | 493 | 38.3 | 77.9 | 57.1 | NA |
| % CV | 44.8 | 47.2 | 38.3 | 53.0 | 34.3 | 25.2 | 9.26 | 51.8 | 44.6 | NA |

Table 33 provides summarized pharmacokinetic parameters of LA1. Choline Salt in Beagle dog.

TABLE 39

Comparison of IV and oral PK parameteres in beagle dogs

| Route of administration | Half life (h) | Co/$C_{max}$ (ng/mL) | $Vd_{SS}$ (mL) | Cl (ml/h) | $T_{max}$ (h) | $AUC_{0-12\,h}$ (h * ng/mL) | $AUC_{0-inf}$ (h * ng/mL) |
|---|---|---|---|---|---|---|---|
| Intravenous (0.5 mg/kg) | 2.15 | 2041.83 | 0.72 | 0.39 | — | 1332.79 | 1350.43 |
| Oral (3 mg/kg) | 2.11 | 685.47 | — | — | 4.0 | 2572.24 | 2689.56 |

Absolute oral bioavailability of LA1.Choline Salt is 50.62% (0.5 mg i.v vs 2 mg oral).

Figure 22:
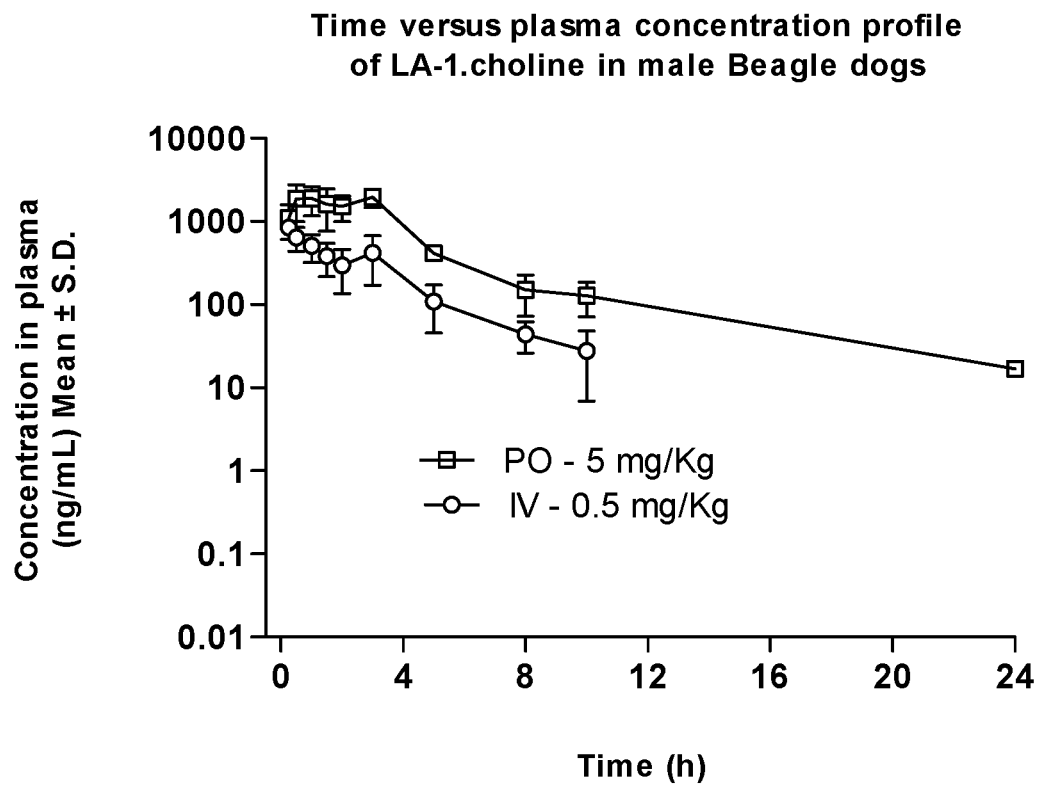
FIG. 22 shows the concentration vs. time profile of LA1 choline salt administered orally (5 mg/kg) and intravenously (0.5 mg/kg) to beagle dogs.

FIG. 22 shows a graph of PK profile for LA1 in beagle dogs at an IV dosage of 0.5 mg/kg and Oral (PO) dosage of 5 mg/kg.

Example 19. Assessment of In Vivo Efficacy of LA1 for Treating Murine Melanoma B16F10 Allograft in C57BL/6 Mice A mouse melanoma tumor cell line, B16-F10, was used for developing a subcutaneous tumor model. $0.1\times10^6$ cells were injected subcutaneously in the right flank region of the animal. When the tumors reached ~45 mm³ the animals were randomized into various groups, each group with 10 animals, so that the average tumor volume of all the groups was similar. Animals were treated from the day of randomization (Day 1). Tumor dimensions (length and diameter) were measured for all animals three times per week, including the termination day of the study. In addition, throughout the study period, mice were monitored daily for clinical conditions. On Day 15, tumor and blood samples were collected from all the mice at $T_{max}$ (0.5 hr) for assessing exposure. Portions of the blood samples were used for blood analysis and clinical chemistry. Lung, heart, liver, spleen, and kidneys were also collected and histopathological analysis was performed.

TUMOR CELLS. B16-F10 cells were cultured in DMEM cell culture medium supplemented with 10% FBS and 1% penicillin-streptomycin. The cells were maintained at 37° C. in the absence of $CO_2$. When the cells reached 75-80% confluence, they were harvested by trypsinization, washed, and counted. The cells were then re-suspended in serum free medium at a concentration of 0.1 million cells/75 µl.

TUMOR CELL INOCULATION. Cells were inoculated subcutaneously on the flank of black mice. Prior to inoculation, hair was trimmed and skin on the injection site (dorsal right flank) was swabbed with alcohol. Cells in serum free medium (0.1 million cells/75 µl) were mixed with Matrigel at a ratio of 3:1 and a total volume of 100 µl was injected into each animal with a 1 mL BD syringe attached to a 26 G needle.

RANDOMIZATION. Tumors were palpable around Day 7 of inoculation. Once the tumor volume reached around 45 mm³, animals were randomized into various groups with 10 animals in all the groups so that the average tumor volume of each group was similar.

| | |
|---|---|
| Vehicle | 5% DMSO + 5% Solutol:Ethanol (1:1) + 20% Tween20 + 70% N-Saline |
| Test Article 1 | LA1 free acid |
| Test Article 2 | LA1 meglumine salt |
| Test Article 3 | Anti-PD1 antibody (RMP1-14; BioXCell) |
| Test Article 4 | Anti-CTLA4 antibody (BioXCell) |

FORMULATION. LA1 was combined with a solution containing 5% DMSO, 5% Solutol:ethanol (1:1), 20% Tween20, and 70% N-saline. LA1 meglumine salt was combined with a solution containing 5% DMSO, 5% Solutol:ethanol (1:1), and 90% N-saline.

STATISTICAL CALCULATIONS. All statistical calculations were performed using Prism 5.0 (GraphPad Software Inc., USA). Comparisons of tumor size measurements during and at the termination of the study were made between the treatment groups and respective vehicle control groups using One Way ANOVA followed by Dunnett's multiple comparison tests. A p-value of less than 0.05 was considered significant.

EXPOSURE OF LA1. At the end of the study, LA1 showed an exposure of 383±450 ng/ml and 24.7±17.6 ng/ml in blood and tumor, respectively. Similarly, LA1 meglumine salt at 3 and 30 mg/kg showed an exposure of 1519±613 ng/ml and 3744±1755 ng/ml in plasma and 1017±510 ng/ml and 1659±611 ng/ml in tumor, respectively.

HISTOPATHOLOGY. Histopathological examination was conducted using liver, kidney, lung, spleen, heart, and stomach samples. Microscopic examination of liver tissues revealed minimal to moderate hepatocellular necrosis in one animal in each of the control group, the LA1 salt group, the α-PD1 group, the α-CTLA4 group, and the α-CTLA4/LA1 salt group. Tumor metastasis was observed in lung tissue from one animal in each of the control group, the LA1 salt group, and the α-PD1 group.

Figure 23:
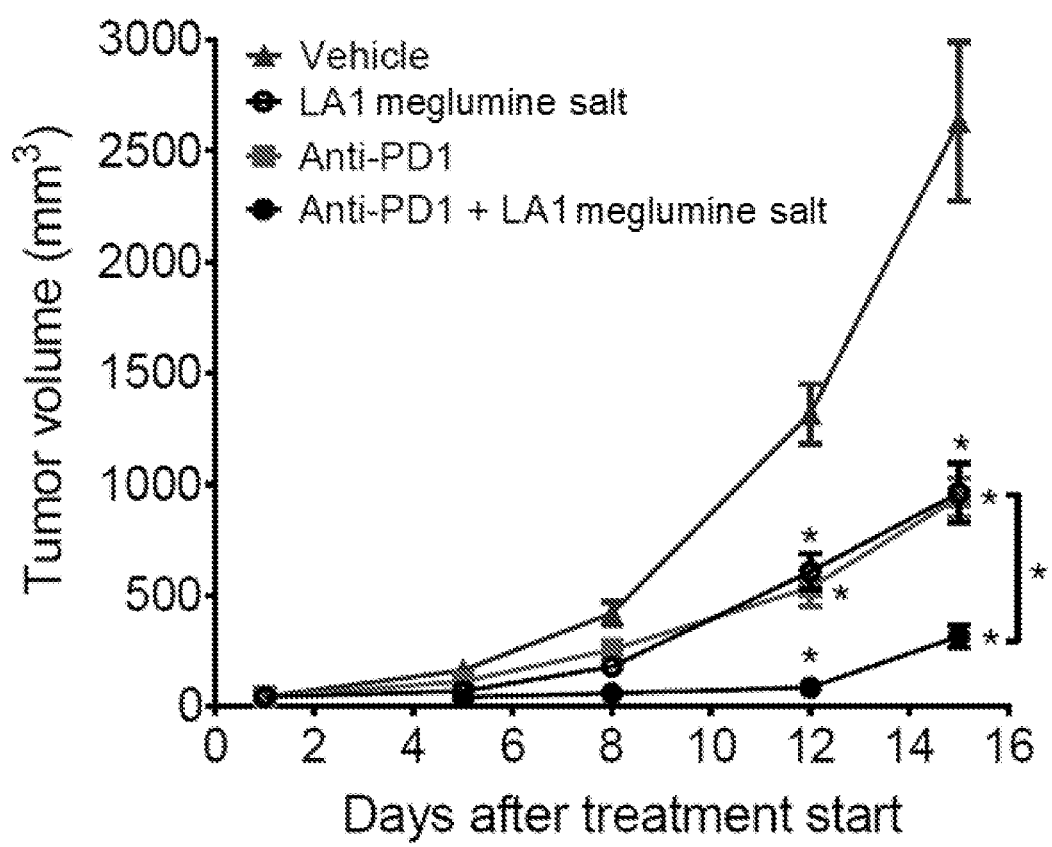
FIG. 23 shows melanoma progression in mice treated with vehicle, LA1 meglumine salt, α-PD1 antibody, or LA1 meglumine salt+α-PD1 antibody.

When dosed at 3 or 30 mg/kg daily for 15 days, treatment with LA1 meglumine salt resulted in about 58-66% growth inhibition of murine melanoma B16-F10 tumors as compared to vehicle control. Treatment with a first immune checkpoint inhibitor (α-CTLA4 antibody, 100 µg/mouse every third day) alone resulted in about 42% growth inhibition. Combination treatment using α-CTLA4 antibody and LA1 resulted in further tumor growth inhibition, as compared to α-CTLA4 alone. However, combination treatment using a second immune checkpoint inhibitor (α-PD1 antibody) and LA1 or LA1 meglumine salt resulted in stronger tumor growth inhibition than either agent used alone. See, FIG. 23. Treatment with α-PD1 antibody showed approximately 64% tumor inhibition, but the combination resulted in approx. 81% tumor inhibition in these assays.

Example 20. Assessment of In Vivo Efficacy of LA1 for Treating Murine Melanoma B16F10 allograft in C57BL/6 mice Mice were inoculated with B16F10 tumors as described above. Once the tumor volume reached around 45 mm³, animals were randomized into various groups with 10 animals in all the groups so that the average tumor volume of each group was similar.

| | |
|---|---|
| Vehicle | 5% DMSO + 5% Solutol:Ethanol (1:1) + 20% Tween20 + 70% N-Saline |
| Test Article 1 | LA1 |
| Test Article 2 | LA1 Choline salt |
| Test Article 3 | Anti-PD1 antibody (RMP1-14; BioXCell) |
| Test Article 4 | Anti-CTLA4 antibody (BioXCell) |

FORMULATION. LA1 was combined with a solution containing 5% DMSO, 5% Solutol:ethanol (1:1), 20% Tween20, and 70% N-saline. LA1 choline salt (recrystallized from n-butanol; Form R) was combined with a solution containing 5% DMSO, 5% Solutol:ethanol (1:1), and 90% N-saline.

ADMINISTRATION. LA1 choline salt, anti-PD1 antibody, and anti-CTLA4 antibody were administered as shown below.

| Group | Treatment | Route | Dosing schedule | Dose (mg/kg) | n/group |
|---|---|---|---|---|---|
| 1 | Vehicle control | | | — | 10 |
| 2 | LA1 choline salt | p.o. | b.i.d | 3 | 10 |
| 3 | LA1 choline salt | | | 10 | 10 |
| 4 | LA1 choline salt | | | 30 | 10 |
| 5 | LA1 choline salt | | | 100 | 10 |
| 6 | Anti PD1 antibody | i.p. | every 4$^{th}$ day | 0.1 mg/mouse | 10 |
| 7 | Anti CTLA4 antibody | i.p. | every 4$^{th}$ day | 0.1 mg/mouse | 10 |
| 8 | LA1 choline salt | p.o. | b.i.d | 3 mg/kg | 10 |
| | Anti-PD-1 antibody | i.p. | every 4$^{th}$ day | 0.1 mg/mouse | |
| 9 | LA1 choline salt | p.o. | b.i.d | 10 mg/kg | 10 |
| | Anti-PD-1 antibody | i.p. | every 4$^{th}$ day | 0.1 mg/mouse | |
| 10 | LA1 choline salt | p.o. | b.i.d | 3 mg/kg BID | 10 |
| | Anti-CTLA4 antibody | i.p. | every 4$^{th}$ day | 0.1 mg/mouse | |
| 11 | LA1 choline salt | p.o. | b.i.d | 10 mg/kg BID | 10 |
| | Anti-CTLA4 antibody | i.p. | every 4$^{th}$ day | 0.1 mg/mouse | |

EXPOSURE OF LA1. At the end of the study, oral administration of LA1 free acid resulted in an exposure below the limit of quantitation in blood and tumor. LA1 choline salt dosed at 3, 10, 30, and 100 mg/kg orally resulted in an exposure of 314±77.7 ng/ml, 996±401 ng/ml, 3518±1483 ng/ml and 21,827±5628 ng/ml in plasma. Administration of the choline salt orally at the 3, 10, 30, and 100 mg/kg doses resulted tumor concentrations of 118±83.1 ng/ml, 254±146 ng/ml, 855±312 ng/ml and 2093±1997 ng/ml in tumor tissue, respectively.

Figure 24:
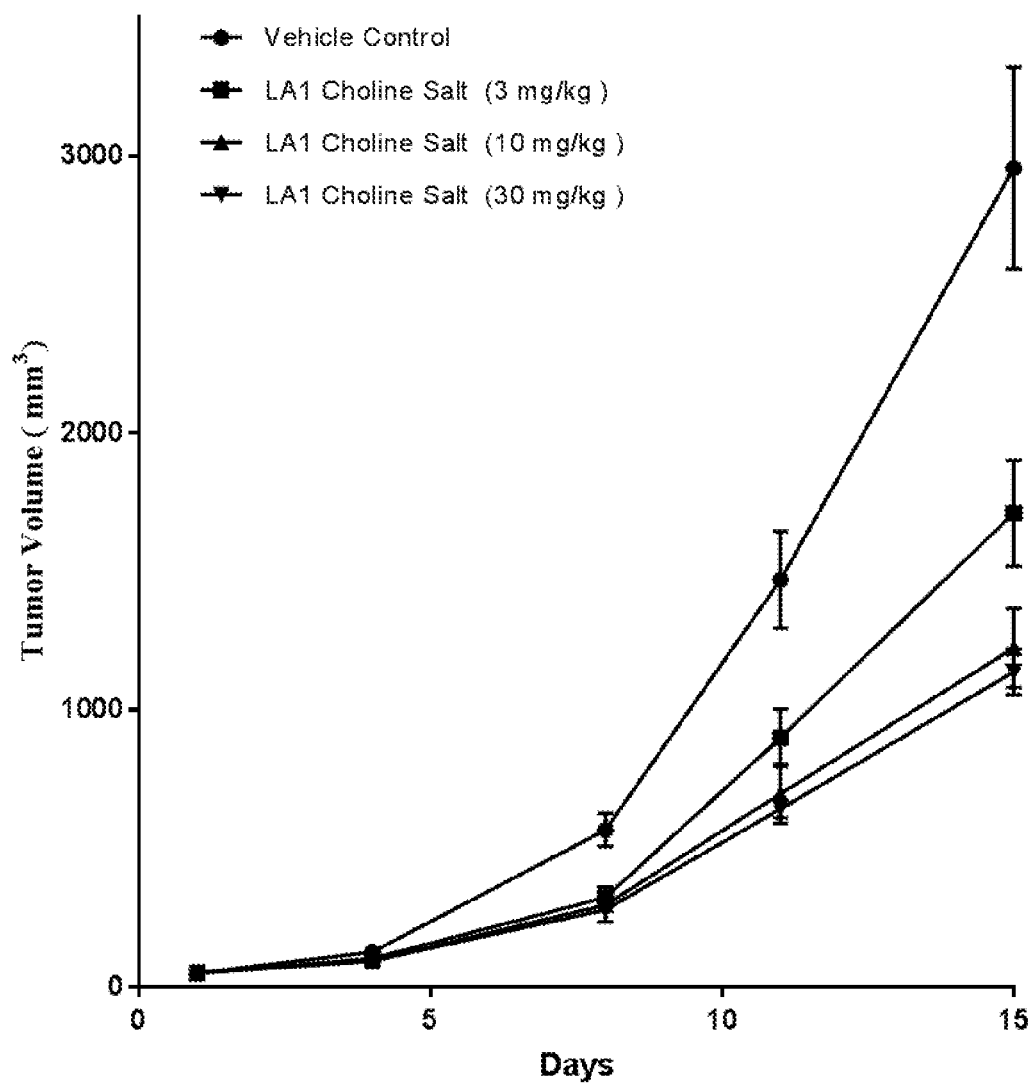
FIG. 24 shows melanoma progression in mice treated with varying amounts of LA1 choline salt.
Figure 25:
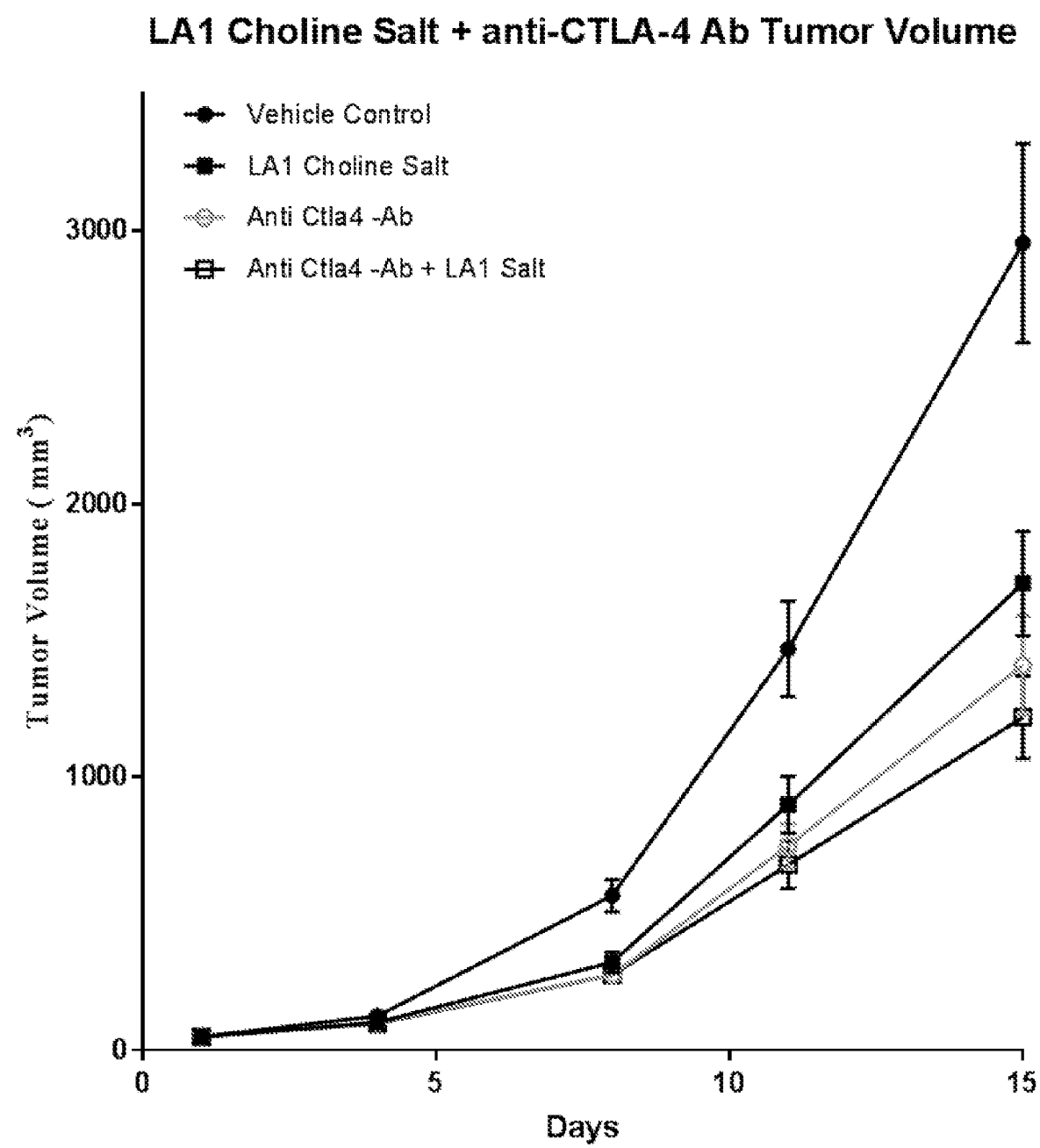
FIG. 25 shows melanoma progression in mice treated with vehicle, LA1 choline salt (3 mg/kg, p.o., b.i.d.), α-PD1 antibody (100 μg/mouse, i.p., every fourth day), or LA1 choline salt+α-PD1 antibody.

The LA1 choline salt decreased tumor volume in a dose dependent manner. See, FIG. 24. Treatment with LA1 choline salt, when dosed at 3-100 mg/kg, resulted in about 43-68% growth inhibition of murine melanoma B16-F10 tumors as compared to vehicle control. Treatment with a first immune checkpoint inhibitor (α-CTLA4 antibody) alone resulted in about 53% growth inhibition. Combination treatment using α-CTLA4 antibody and LA1 choline salt (3 mg/kg and 10 mg/kg) resulted in further tumor growth inhibition, 60% and 67%, respectively, as compared to α-CTLA4 alone. See, FIG. 25.

Figure 26:
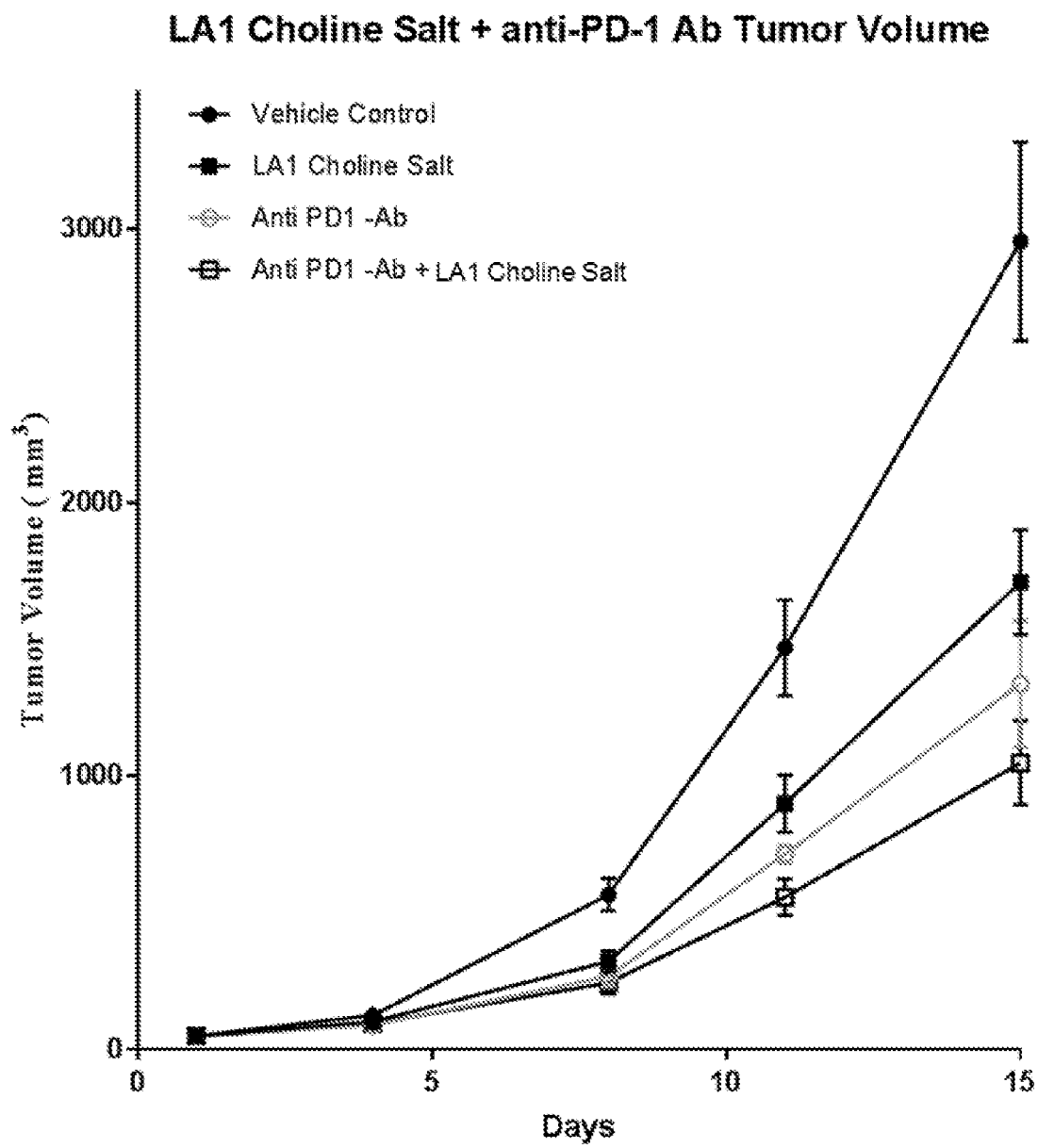
FIG. 26 shows melanoma progression in mice treated with vehicle, LA1 choline salt (3 mg/kg, p.o., b.i.d.), α-CTLA-4 antibody (100 μg/mouse, i.p., every fourth day), or LA1 choline salt+α-CTLA-4 antibody.

Treatment using a second immune checkpoint inhibitor (α-PD1 antibody) resulted in approximately 56% tumor inhibition. Combination treatment of α-PD1 antibody and LA1 choline salt (3 mg/kg and 10 mg/kg) resulted in further tumor growth inhibition, 66% and 68%, respectively, as compared to α-PD1 antibody alone. See, FIG. 26.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications, websites, and databases cited herein are hereby incorporated by reference in their entireties for all purposes.

What is claimed is:

1. A crystalline form of a choline salt of a compound of Formula (I):

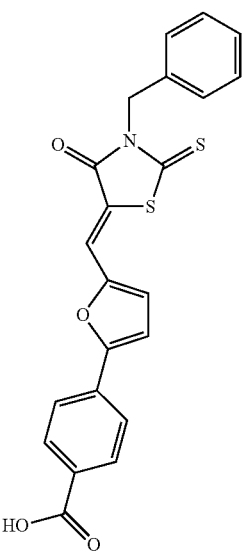

(I)

which is crystalline form G characterized by an X-ray powder diffraction (XRPD) pattern comprising at least three peaks selected from the group consisting of 5.6, 7.9, 11.2, 13.3, 15.0, 15.7, 16.1, 16.2, 16.5, 16.6, 17.8, 18.1, 18.5, 19.1, 19.8, 20.0, 21.1, 23.0, 24.6, 25.0, 25.6, 26.6, 26.8, 26.9, 29.3, 29.7, 30.6, 30.7, and 34.4 °2θ, ±0.2 °2θ, as determined on a diffractometer using Cu-Kα radiation.

2. A crystalline form of a choline salt of a compound of Formula (I):

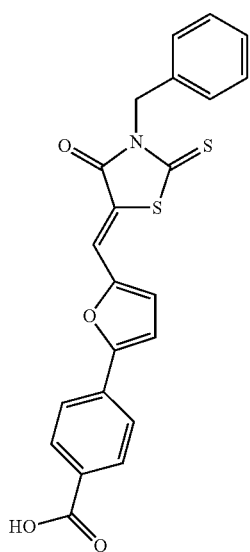

(I)

which is crystalline form O characterized by an X-ray powder diffraction (XRPD) pattern comprising at least three peaks selected from the group consisting of 8.4, 8.8, 9.3, 13.3, 14.3, 16.7, 17.0, 18.1, 19.4, 19.6, 19.9, 20.7, 20.9, 21.4, 21.7, 22.5, 23.4, 24.1, and 25.5 °2θ, ±0.2 °2θ, as determined on a diffractometer using Cu-Kα radiation.

3. A crystalline form of a choline salt of a compound of Formula (I):

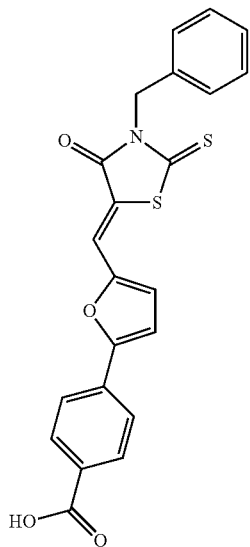

(I)

which is crystalline form Q characterized by an X-ray powder diffraction (XRPD) pattern comprising at least three peaks selected from the group consisting of 5.0, 5.2, 8.4, 9.6, 9.9, 11.5, 12.6, 12.8, 13.3, 14.4, 15.8, 16.1, 16.6, 17.5, 18.0, 19.3, 20.6, 20.7, 21.5, 21.7, 22.9, 23.7, 24.8, 25.1, 25.3, 25.3, 25.5, 26.3, 26.9, 27.0, 28.1, 28.8, 30.4, 31.2, 32.0, 35.7, and 37.4 °2θ, ±0.2 °2θ, as determined on a diffractometer using Cu-Kα radiation.

4. A crystalline form of a choline salt of a compound of Formula (I):

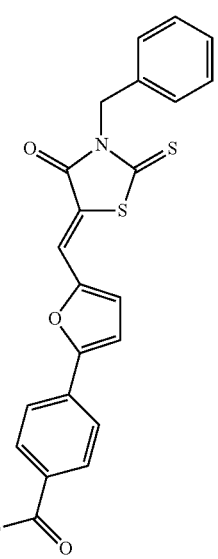

(I)

which is crystalline form R characterized by an X-ray powder diffraction (XRPD) pattern comprising at least three peaks selected from the group consisting of 5.1, 5.6, 8.0, 8.2, 8.4, 9.8, 11.2, 12.7, 13.4, 14.6, 15.1, 15.7, 16.1, 16.3, 16.7, 17.1, 17.8, 18.2, 18.5, 19.1, 19.9, 20.1, 21.1, 22.6, 23.0, 23.4, 24.0, 24.5, 24.7, 25.0, 25.6, 26.0, 26.6, 26.8, 27.1, 27.4, 27.7, 28.1, 29.3, 29.7, 30.6, 31.1, 31.7, 32.2, 32.8, 33.2, 33.5, 34.5, 34.8, 35.1, 35.4, 36.5, 37.6, 38.5, 39.5, 40.4, 41.3, 42.7, and 44.4 °2θ, ±0.2 °2θ, as determined on a diffractometer using Cu-Kα radiation.

5. A crystalline form of a choline salt of a compound of Formula (I):

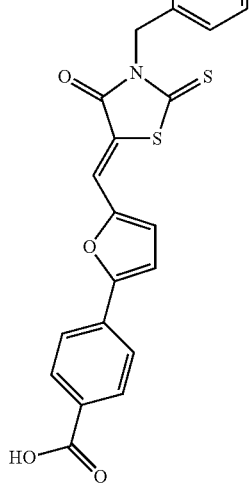

(I)

which is crystalline form S characterized by an X-ray powder diffraction (XRPD) pattern including at least three peaks selected from 5.1, 8.4, 9.6, 10.0, 11.6, 12.9, 13.3, 14.4, 14.9, 15.8, 16.6, 17.4, 18.0, 19.2, 19.3, 20.6, 21.4, 21.7, 22.7, 23.7, 24.8, 25.4, 26.3, 26.8, 28.1, 28.7, 29.6, 30.3, 31.0, 31.9, 33.0, 34.0, 35.7, 37.4, 39.2, 40.5, and 41.7 °2θ, ±0.2 °2θ, as determined on a diffractometer using Cu-Kα radiation.

6. The crystalline form of claim 4, which is crystalline form R characterized by an X-ray powder diffraction (XRPD) pattern including at least six peaks selected from 5.6, 11.2, 15.1, 16.3, 16.7, 19.1, 20.1, 21.1, 23.0, 24.5, 25.0, 25.6, 26.0, 31.1, 32.8, and 33.5±0.2 °2θ, as determined on a diffractometer using Cu-Kα radiation.

7. The crystalline form of claim 4, which is crystalline form R characterized by an X-ray powder diffraction (XRPD) pattern including at least nine peaks selected from 5.6, 11.2, 15.1, 16.3, 16.7, 19.1, 20.1, 21.1, 23.0, 24.5, 25.0, 25.6, 26.0, 31.1, 32.8, and 33.5±0.2 °2θ, as determined on a diffractometer using Cu-Kα radiation.

8. The crystalline form of claim 4, which is crystalline form R characterized by an X-ray powder diffraction (XRPD) pattern in accordance with FIG. 7, as determined on a diffractometer using Cu-Kα radiation.

9. A crystalline form of a meglumine salt of a compound of Formula (I):

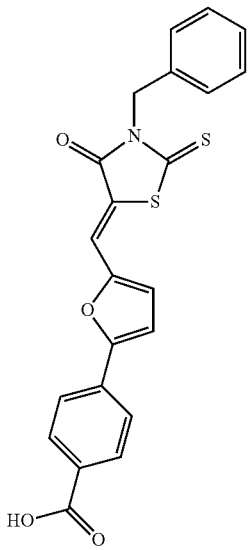

(I)

which is crystalline form H characterized by an X-ray powder diffraction (XRPD) pattern comprising at least three peaks selected from the group consisting of 5.3, 7.1, 10.7, 10.9, 16.1, 16.5, 17.7, 18.5, 20.3, 23.6, 24.9, and 27.2 °2θ, ±0.2 °2θ, as determined on a diffractometer using Cu-Kα radiation.

10. A crystalline form of a meglumine salt of a compound of Formula (I):

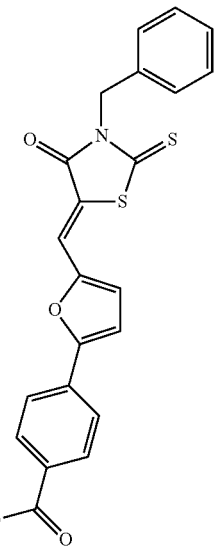

(I)

which is crystalline form L characterized by an X-ray powder diffraction (XRPD) pattern including at least three peaks selected from 5.3, 7.9, 8.5, 9.0, 9.9, 10.6, 10.9, 11.6, 12.0, 12.6, 13.1, 14.5, 14.8, 15.0, 15.3, 15.9, 16.2, 16.9, 17.4, 17.8, 18.0, 18.4, 18.8, 19.2, 20.2, 20.8, 21.3, 21.7, 22.1, 23.2, 23.8, 24.5, 25.2, 25.5, 26.3, 26.9, 27.3, 27.9, 28.4, 28.9, 29.2, 29.8, 30.3, 30.6, 31.1, 32.1, 32.8, 34.1, 34.5, 34.9, 35.1, 36.0, 36.5, 37.5, 38.0, 38.9, 39.6, 40.7, 41.7, 42.5, and 42.9 °2θ, ±0.2 °2θ, as determined on a diffractometer using Cu-Kα radiation.

11. A crystalline form of a meglumine salt of a compound of Formula (I):

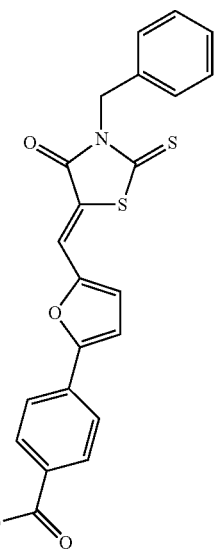

(I)

which is crystalline form M characterized by an X-ray powder diffraction (XRPD) pattern including at least three peaks selected from 6.5, 8.5, 9.0, 9.9, 10.6, 11.6, 14.4, 14.8, 15.0, 15.3, 15.9, 16.1, 16.9, 17.8, 18.0, 19.0, 20.4, 20.8, 21.3, 21.7, 23.6, 24.5, 25.2, 26.3, 26.9, 27.5, 27.9, 28.5, 28.9, 29.8, 30.6, 32.1, 32.8, 33.8, 34.5, 36.0, 36.4, 37.1, 38.0, 39.7, 40.7, 41.7, 43.0, and 44.0 °2θ, ±0.2 °2θ, as determined on a diffractometer using Cu-Kα radiation.

12. A crystalline form of a meglumine salt of a compound of Formula (I):

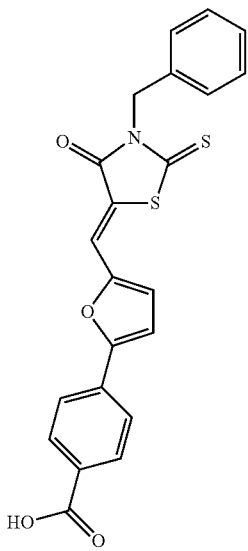

(I)

which is crystalline form N characterized by an X-ray powder diffraction (XRPD) pattern including at least three peaks selected from 4.3, 5.0, 5.4, 6.1, 7.5, 7.9, 8.9, 9.5, 10.0, 10.8, 11.4, 12.1, 12.5, 13.8, 14.3, 14.8, 15.6, 16.1, 16.7, 17.4, 18.1, 19.2, 19.5, 20.1, 20.9, 21.4, 21.5, 22.1, 22.5, 23.9, 24.6, 25.3, 26.3, 26.7, 27.1, 27.6, 28.2, 29.0, 30.4, 30.9, 32.0, 32.9, 33.9, 34.7, 36.9, 38.3, 39.1, 39.6, 40.2, and 41.4 °2θ, ±0.2 °2θ, as determined on a diffractometer using Cu-Kα radiation.

13. A crystalline form of a meglumine salt of a compound of Formula (I):

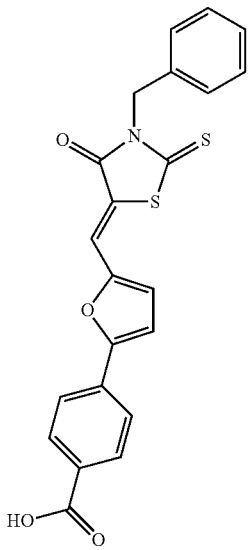

(I)

which is crystalline form T characterized by an X-ray powder diffraction (XRPD) pattern comprising at least three peaks selected from the group consisting of 6.9, 8.2, 8.4, 9.4, 11.6, 15.0, 15.1, 15.5, 17.2, 17.8, 18.1, 20.5, 21.3, 21.9, 22.3, 23.5, 25.0, and 26.7 °2θ, ±0.2 °2θ, as determined on a diffractometer using Cu-Kα radiation.

14. The crystalline form of claim 9, which is crystalline form H characterized by an X-ray powder diffraction (XRPD) pattern comprising at least six peaks selected from the group consisting of 5.3, 7.1, 10.7, 10.9, 16.1, 16.5, 17.7, 18.5, 20.3, 23.6, 24.9, and 27.2±0.2 °2θ, as determined on a diffractometer using Cu-Kα radiation.

15. The crystalline form of claim 9, which is crystalline form H characterized by an X-ray powder diffraction (XRPD) pattern comprising at least ten peaks selected from the group consisting of 5.3, 7.1, 10.7, 10.9, 16.1, 16.5, 17.7, 18.5, 20.3, 23.6, 24.9, and 27.2±0.2 °2θ, as determined on a diffractometer using Cu-Kα radiation.

16. The crystalline form of claim 9, which is crystalline form H characterized by an X-ray powder diffraction (XRPD) pattern substantially in accordance with FIG. 6B, as determined on a diffractometer using Cu-Kα radiation.

17. A crystalline form of a tromethamine salt of a compound of Formula (I):

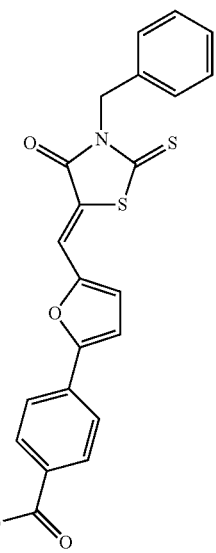

(I)

which is characterized by an X-ray powder diffraction (XRPD) pattern substantially in accordance with FIG. 6C, as determined on a diffractometer using Cu-Kα radiation.

18. A crystalline form of a tromethamine salt of a compound of Formula (I):

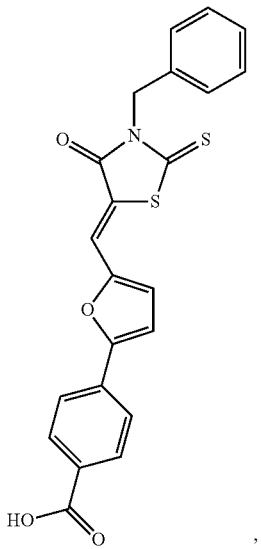

(I)

, which is characterized by an X-ray powder diffraction (XRPD) pattern substantially in accordance with FIG. 6D, as determined on a diffractometer using Cu-Kα radiation.

19. A pharmaceutical formulation comprising a pharmaceutically acceptable excipient and a crystalline form of a choline salt of a compound of Formula (I) as recited in any one of claims 1, 2, 3, 4, 5, 6, 7 or 8.

20. A pharmaceutical formulation comprising a pharmaceutically acceptable excipient and a crystalline form of a meglumine salt of a compound of Formula (I) as recited in any one of claim 9, 10, 11, 12, 13, 14, 15 or 16.

21. A method for treating a β2 integrin-mediated condition comprising administering to a patient having said condition a pharmaceutical formulation 19.

22. A method for treating a β2 integrin-mediated condition comprising administering to a patient having said condition a pharmaceutical composition of claim 20.

23. The method of claim 21, wherein the β2 integrin-mediated condition is selected from the group consisting of acute inflammation, chronic inflammation, chronic kidney disease, neointimal thickening associated with vascular injury, tissue injury, peritonitis, diabetic nephropathy, an autoimmune disease, cancer, glaucoma, graft versus host disease, macular degeneration, and uveitis.

24. The method of claim 21, wherein the β2 integrin-mediated condition is cancer.

25. The method of claim 22, wherein the β2 integrin-mediated condition is selected from the group consisting of acute inflammation, chronic inflammation, chronic kidney disease, neointimal thickening associated with vascular injury, tissue injury, peritonitis, diabetic nephropathy, an autoimmune disease, cancer, glaucoma, graft versus host disease, macular degeneration, and uveitis.

26. The method of claim 22, wherein the β2 integrin-mediated condition is cancer.

* * * * *